United States Patent [19]

Horii et al.

[11] Patent Number: 4,595,678
[45] Date of Patent: Jun. 17, 1986

[54] N-SUBSTITUTED PSEUDO-AMINOSUGARS AND PHARMACEUTICAL COMPOSITIONS CONTAINING SAME

[75] Inventors: Satoshi Horii, Sakai; Yukihiko Kameda, Kanazawa; Hiroshi Fukase, Osaka, all of Japan

[73] Assignee: Takeda Chemical Industries, Ltd., Osaka, Japan

[21] Appl. No.: 475,615

[22] Filed: Mar. 15, 1983

[30] Foreign Application Priority Data

Mar. 19, 1982 [JP] Japan .................................. 57-45345
Jun. 10, 1982 [JP] Japan ................................. 57-100325
Oct. 19, 1982 [JP] Japan ................................. 57-183433
Nov. 22, 1982 [JP] Japan ................................. 57-204936

[51] Int. Cl.$^4$ .......................... A61K 31/73; C07H 5/06
[52] U.S. Cl. ........................................ 514/53; 514/23; 514/54; 536/17.2; 536/18.7; 536/123; 564/300; 564/462
[58] Field of Search .................... 536/17.2, 17.9, 18.7; 514/53, 54, 23; 564/300, 462

[56] References Cited

U.S. PATENT DOCUMENTS 4,062,950 12/1977 Frommer et al. .
4,254,256  3/1981 Otani et al. ............... 536/17.2
4,316,894  2/1982 Omoto et al. .............. 536/18.7

FOREIGN PATENT DOCUMENTS 49981  4/1982 European Pat. Off. .
56194  7/1982 European Pat. Off. .
0089812 9/1983 European Pat. Off. .......... 536/18.7
2905649 8/1979 Fed. Rep. of Germany .
57-24397 2/1982 Japan ........................... 536/17.9

Primary Examiner—Johnnie R. Brown
Attorney, Agent, or Firm—Wegner & Bretschneider

[57] ABSTRACT

A compound of the general formula:

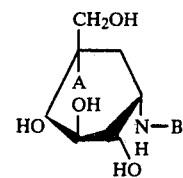

wherein A is hydrogen or a hydroxyl group; B is (1) a group of the formula;

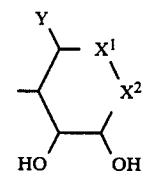

(2) a group of the formula;

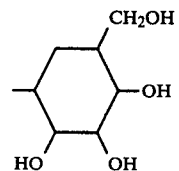

or (3) a group of the formula;

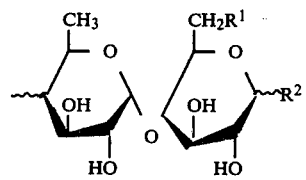

or a pharmaceutically acceptable salt thereof is novel and possesses excellent inhibitory activity against α-glucoside hydrolase and are useful for hyperglycemic symptoms and various disorders caused by hyperglycemia.

24 Claims, No Drawings

N-SUBSTITUTED PSEUDO-AMINOSUGARS AND PHARMACEUTICAL COMPOSITIONS CONTAINING SAME

The present invention relates to N-substituted pseudo-aminosugars having an inhibitory activity against α-glucoside hydrolase, to processes for producing the same, and to α-glucosidase inhibitors containing the abovementioned derivatives.

The present inventors previously isolated as a constituent of validamycin, an antibiotic, the compound of the formula:

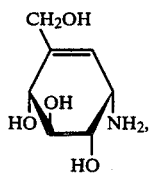

which was named "valienamine" (Y. Kameda and S. Horii; Journal of the Chemical Society; Chemical Communications, 1972, 746 to 747), and reported that valienamine possesses an action of suppressing the function of α-glucoside hydrolase (Y. Kameda et al., Journal of Antibiotics 33, 1575 to 1576 (1980)). In recent years, various compounds having valienamine moiety, which exhibit α-glucosidase inhibitory activity, are reported e.g. "Acarbose" in U.S. Pat. No. 4,062,950, "Trestatin A, B and C" in German laid open patent application No. 2,905,649, but their actions to suppress the function of α-glucoside hydrolase are far from being satisfactory.

The present inventors investigated an α-glucosidase inhibitory activity of various compounds which are similar to valienamine in chemical structure and, after much research, found that validamine [Horii et al., Journal of Antibiotics 24, pp. 59 to 63 (1971)] possesses a highly valuable action of suppressing the function of α-glucoside hydrolase or the action as an α-glucosidase inhibitor. The present inventors also found that valiolamine of the formula:

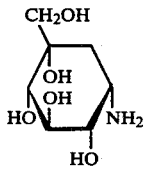

which was discovered and isolated from a culture broth of the genus streptomyces, possesses α-glucosidase inhibitory activity (European laid open patent application No. 63456).

Further, the present inventors have succeeded in preparing new below-mentioned compounds [I] as well as a pharmaceutically acceptable salt thereof, and found that these compounds possesses an excellent activity of suppressing the function of α-glucoside hydrolase.

These findings were followed by continued studies on various novel derivatives of validamine or valiolamine, which have culminated in the present invention.

Thus the present invention relates to: a compound of the general formula:

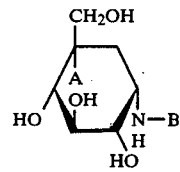

wherein A is hydrogen or a hydroxyl group; B is (1) a group of the formula:

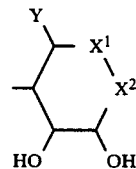

where $X^1$ and $X^2$ are each a group represented by

either of $X^1$ and $X^2$ is oxygen while the other is a group represented by

or $X^1$ and $X^2$ combine to be oxygen; Y is ① a lower alkyl group of 1 to 4 carbon atoms which may have a hydroxyl substituent, ② a hydroxyl group or ③ an amino group; and Z is hydrogen, a hydroxyl group, a hydroxymethyl group or an amino group; (2) a group of the formula:

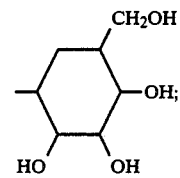

or (3) a group of the formula:

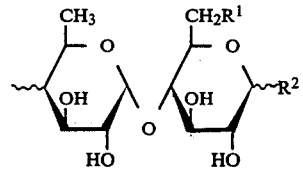

where $R^1$ and $R^2$ are each a hydroxyl group or combine to be oxygen, the chemical bond ⁓ designates either the R- or/and S-configurations; and the amino group or hydroxyl group may be protected, or a pharmaceutically acceptable salt thereof.

When the terms, valienamine, validamine and valiolamine, are employed as the common or trivial names in the naming of the compounds as described herein, the position number for each of the carbon atoms are assigned to the respective compounds as illustrated in the following:

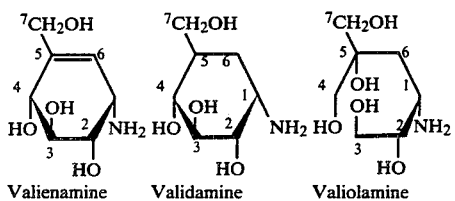

Valienamine    Validamine    Valiolamine

The position number for each of the carbon atoms in 2,3,4-trihydroxy-5-hydroxymethylcyclohexyl group and 4-substituted-2,3-dihydroxy-6-methylcyclohexyl group (the N-substituted moiety represented by B in the general formula [I]) is assigned as shown in the following formulae:

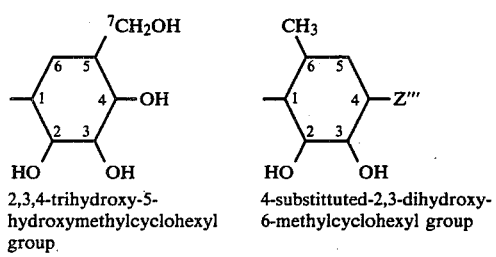

2,3,4-trihydroxy-5-hydroxymethylcyclohexyl group    4-substittuted-2,3-dihydroxy-6-methylcyclohexyl group

[wherein $Z'''$ is an amino group or an hydroxyl group]. Referring to the above general formula [I], examples of the group represented by the formula:

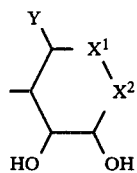

in the substituent represented by B include the groups having the above formula wherein ① Y is a lower alkyl group of 1 to 4 carbon atoms which may have a hydroxyl substituent, $X^1$ is oxygen and $X^2$ is

(where Z is a protected hydroxyl group, e.g. a lower alkoxy group of 1 to 4 carbon atoms such as methoxy, ethoxy, propoxy and butoxy); ② Y is a hydroxyl group, $X^1$ is

(where X is a hydroxymethyl group) and $X^2$ is oxygen; ③ Y is a lower alkyl group of 1 to 4 carbon atoms which may have a hydroxyl substituent, $X^1$ is

(where Z is hydrogen) and $X^2$ is

(where Z is an amino group which may be protected); ④ Y is an amino group which may be protected, $X^1$ is

(where Z is hydrogen) and $X^2$ is

(where Z is an amino group which may be protected); and ⑤ Y is a lower alkyl group of 1 to 4 carbon atoms which may have a hydroxyl substituent, and $X^1$ and $X^2$ combine to be oxygen. The lower alkyl group of 1 to 4 carbon atoms in the lower alkyl group of 1 to 4 carbon atoms which may have a hydroxyl substituent represented by Y includes a straight-chain or branched alkyl group of 1 to 4 carbon atoms such as methyl, ethyl, propyl, isopropyl, butyl, isobutyl, sec-butyl and tert-butyl, preferably, methyl and ethyl, and specific examples of the lower alkyl group of 1 to 4 carbon atoms which has a hydroxyl substituent include such as hydroxymethyl, 1-hydroxyethyl, 2-hydroxyethyl (the D- and L-glycero-configurations), 1,2-dihydroxyethyl (the D- and L-glycero-configurations), etc., and with reference to the amino group, hydroxyl group, hydroxymethyl group and lower alkyl group of 1 to 4 carbon atoms which have a hydroxyl substituent, all or a part of such amino and hydroxyl groups may be protected. The compound [I] can occur in various kinds of stereoisomers which depend upon (1) diferences in configuration of the amino group, hydroxyl group, hydroxymethyl group and lower alkyl group of 1 to 4 carbon atoms which may have a hydroxyl substituent in the substituent represented by B and (2) differences in configuration at the position where the amino group of validamine or valiolamine moiety of the compound [I] is bonded to the group of the formula:

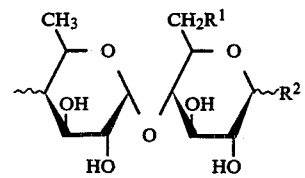

(wherein the symbols are as defined above) in the substituent B.

Examples of the group represented by the formula,

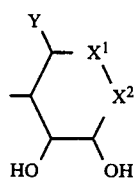

(wherein the symbols are as defined above) include the group represented by the formula

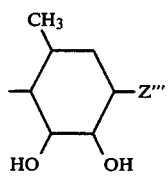

(where Z''' is an amino group or hydroxyl group), such as (1R)-(2,4,6/3)-, (1R)-(2,3,6/4)-, (1R)-(2,3,4/6)-, (1R)-(2,3/4,6)-, (1R)-(2,4/3,6)-, (1R)-(2,6/3,4)-, (1R)-(2/3,4,6)- or (1R)-(2,3,4,6/0)-2,3,4-trihydroxy-6-methylcyclohexyl group;

(1R)-(2,4,6/3)-, (1R)-(2,3,6/4)-, (1R)-(2,3,4/6)-, (1R)-(2,3/4,6)-, (1R)-(2,4/3,6)-, (1R)-(2,6/3,4)-, (1R)-(2/3,4,6)- or (1R)-(2,3,4,6/0)-4-amino-2,3-dihydroxy-6-methylcyclohexyl group;

(1S)-(2,4,6/3)-, (1S)-(2,3,6/4)-, (1S)-(2,3,4/6)-, (1S)-(2,3/4,6)-, (1S)-(2,4/3,6)-, (1S)-(2,6/3,4)-, (1S)-(2/3,4,6)- or (1S)-(2,3,4,6/0)-2,3,4-trihydroxy-6-methylcyclohexyl group;

(1S)-(2,4,6/3)-, (1S)-(2,3,6/4)-, (1S)-(2,3,4/6)-, (1S)-(2,3/4,6)-, (1S)-(2,4/3,6)-, (1S)-(2,6/3,4)-, (1S)-(2/3,4,6)- or (1S)-(2,3,4,6/0)-4-amino-2,3-dihydroxy-6-methylcyclohexyl group etc.

Among these, examples of the group represented by the formula

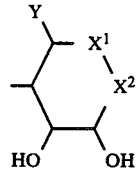

[wherein the symbols are as defined above] are shown below:

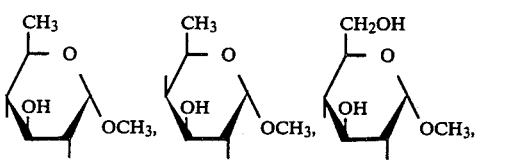

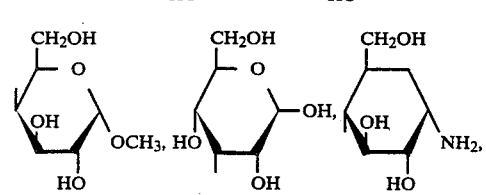

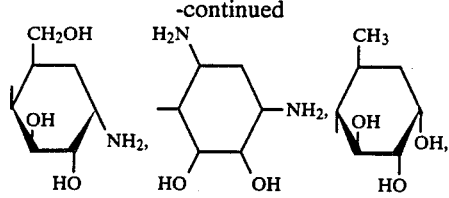

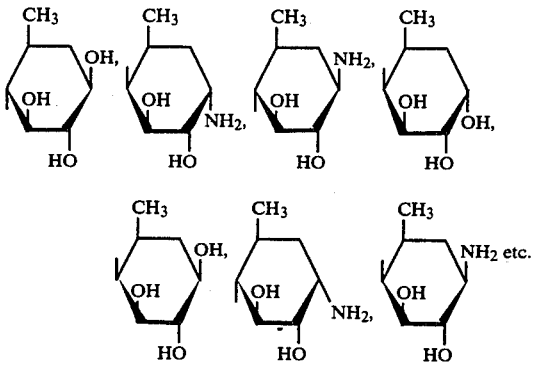

Examples of the group represented by the formula

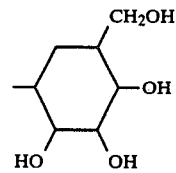

include:

(1R)-(2,4/3,5)-, (1R)-(2,3,4/5)-, (1R)-(2/3,4,5)-, (1R)-(2,3,5/4)- or (1R)-(2,4,5/3)-2,3,4-trihydroxy-5-hydroxymethylcyclohexyl group, (1S)-(2,4/3,5)-, (1S)-(2,3,4/5)-, (1S)-(2/3,4,5)-, (1S)-(2,3,5/4)- or (1S)-(2,4,5/3)-2,3,4-trihydroxy-5-hydroxymethylcyclohexyl group etc.

Further, specific examples of the above group are shown below:

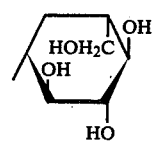

[(1R,2S)-(2,4/3,5)-2,3,4-trihydroxy-5-hydroxymethylcyclohexyl group],

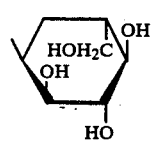

[(1S,2S)-(2,4/3,5)-2,3,4-trihydroxy-5-hydroxymethylcyclohexyl group] etc.

This nomenclature for such configuration, follows the IUPAC-IUB 1973 Recommendation for Cyclitol; Pure and Applied Chemistry, 37, 285 to 297 (1975).

Examples of the group represented by the formula,

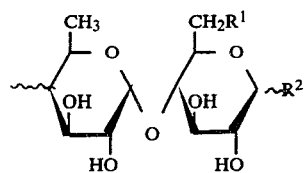

(wherein the symbols are as defined above) include:

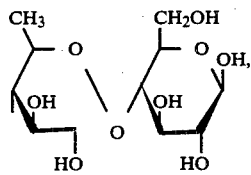

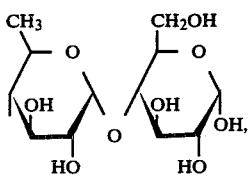

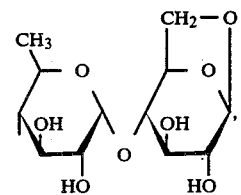

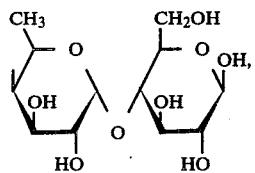

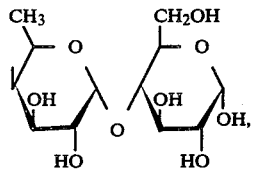

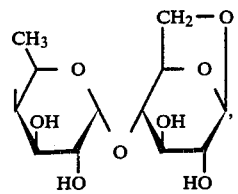

Among these, preferred examples of the substituent B include a group of the formula:

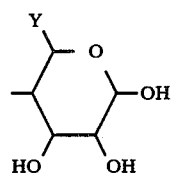

where Y is a lower alkyl group of 1 to 4 carbon atoms which may have a hydroxyl substituent (the hydroxyl group may be protected) or a group of the formula:

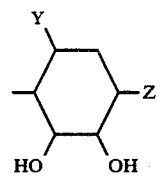

where Y is a lower alkyl group of 1 to 4 carbon atoms; and Z is a hydroxyl group or an amino group (the hydroxyl or amino group may be protected). More concretely, preferred examples of the substituent B include 2-methoxy-3,4-dihydroxy-6-hydroxymethyltetrahydropyran-5-yl, 2-methoxy-3,4-dihydroxy-6-methyltetrahydropyran-5-yl, 4-amino-2,3-dihydroxy-6-methylcyclohexan-1-yl and 2,3,4-trihydroxy-6-methylcyclohexan-1-yl.

Specific examples of the compound [I] are;

Methyl 4-[(1S,2S)-(2,4/3,5)-2,3,4-trihydroxy-5-hydroxymethylcyclohexyl]amino-4,6-dideoxy-α-D-glucopyranoside, Methyl 4-[(1S,2S)-(2,4/3,5)-2,3,4-trihydroxy-5-hydroxymethylcyclohexyl]amino-4,6-dideoxy-α-D-galactopyranoside, Methyl 4-[(1S,2S)-(2,4,5(OH)/3,5(CH₂OH))-2,3,4,5-tetrahydroxy-5-hydroxymethylcyclohexyl]amino-4,6-dideoxy-α-D-glucopyranoside, Methyl 4-[(1S,2S)-(2,4,5(OH)/3,5(CH₂OH))-2,3,4,5-tetrahydroxy-5-hydroxymethylcyclohexyl]amino-4,6-dideoxy-α-D-galactopyranoside, Methyl 4-[(1S,2S)-(2,4/3,5)-2,3,4-trihydroxy-5-hydroxymethylcyclohexyl]amino-4-deoxy-α-D-glucopyranoside, Methyl 4-[(1S,2S)-(2,4/3,5)-2,3,4-trihydroxy-5-hydroxymethylcyclohexyl]amino-4-deoxy-α-D-galactopyranoside, Methyl 4-[(1S,2S)-(2,4,5(OH)/3,5(CH₂OH))-2,3,4,5-tetrahydroxy-5-hydroxymethylcyclohexyl)amino-4-deoxy-α-D-glucopyranoside, Methyl 4-[(1S,2S)-(2,4,5(OH)/3,5-(CH₂OH))-2,3,4,5-tetrahydroxy-5-hydroxymethylcyclohexyl]amino-4-deoxy-α-D-galactopyranoside,

[(1S,2S)-(2,4/3,5)-2,3,4-trihydroxy-5-hydroxymethylcyclohexyl][(2S)-(2,6/3,4)-4-benzyloxycarbonylamino-2,3-dihydroxy-6-hydroxymethylcyclohexyl]amine,

[(1S,2S)-(2,4/3,5)-2,3,4-trihydroxy-5-hydroxymethylcyclohexyl][(1R,2S)-(2,6/3,4)-4-amino-2,3-dihydroxy-6-hydroxymethyl]amine,

[(1S,2S)-(2,4/3,5)-2,3,4-trihydroxy-5-hydroxymethylcyclohexyl][(1S,2S)-(2,6/3,4)-4-amino-2,3-dihydroxy-6-hydroxymethyl)amine,

[(1S,2S)-(2,4,5(OH)/3,5(CH₂OH))-2,3,4,5-tetrahydroxy-5-hydroxymethylcyclohexyl][(1R,2S)-(2,6/3,4)-4-benzyloxycarbonylamino-2,3-dihydroxy-6-hydroxymethylcyclohexyl]amine,

[(1S,2S)-(2,4,5(OH)/3,5(CH₂OH))-2,3,4,5-tetrahydroxy-5-hydroxymethylcyclohexyl][(1S,2S)-(2,6/3,4)-4-benzyloxycarbonylamino-2,3-dihydroxy-6-hydroxymethylcyclohexyl]amine,

[(1S,2S)-(2,4,5(OH)/3,5(CH₂OH))-2,3,4,5-tetrahydroxy-5-hydroxymethylcyclohexyl][(1R,2S)-(2,6/3,4)-4-amino-2,3-dihydroxy-6-hydroxymethylcyclohexyl]amine,

[(1S,2S)-(2,4,5(OH)/3,5(CH₂OH))-2,3,4,5-tetrahydroxy-5-hydroxymethylcyclohexyl][(1S,2S)-(2,6/3,4)-4-amino-2,3-dihydroxy-6-hydroxymethylcyclohexyl]amine,
N-(2,3,5-trihydroxy-6-hydroxymethyltetrahydropyran-4-yl)valiolamine,
N-(2,3-O-isopropylidene-2,3-dihydroxy-5-(1,2-dihydroxyethyl)tetrahydrofuran-4-yl]valiolamine,
N-(2,4-diethoxycarbonylamino-5,6-dihydroxycyclohexyl)valiolamine,
N-(2,4-diamino-5,6-dihydroxycyclohexyl]valiolamine,
N-(2,4-diethoxycarbonylamino-5,6-dihydroxycyclohexyl)valiolamine,
N-(2,4-diamino-5,6-dihydroxycyclohexyl)validamine,
Methyl 4-[(1S,6S)-(4,6/5)-4,5,6-trihydroxy-3-hydroxymethyl-2-cyclohexen-1-yl]amino-4,6-dideoxy-α-D-galactopyranoside,
N-(2,3,5-trihydroxy-6-hydroxymethyltetrahydropyran-4-yl)valienamine,
N-[2,3-O-isopropylidene-2,3-dihydroxy-5-(1,2-dihydroxyethyl)tetrahydrofuran-4-yl]valienamine,
Methyl 4-[(1S,6S)-(4,6/5)-4,5,6-trihydroxy-3-hydroxymethyl-2-cyclohexen-1-yl]amino-4-deoxy-α-D-glucopyranoside,
Methyl 4-[(1S,6S)-(4,6/5)-4,5,6-trihydroxy-3-hydroxymethyl-2-cyclohexen-1-yl]amino-4-deoxy-α-D-galactopyranoside,
N-[(1R,2S)-(2,4/3,5)-2,3,4-trihydroxy-5-hydroxymethylcyclohexyl]valiolamine,
N-[(1R,2S)-(2,4/3,5)-2,3,4-trihydroxy-5-hydroxymethylcyclohexyl]validamine,
N-[(1S,2S)-(2,4/3,5)-2,3,4-trihydroxy-5-hydroxymethylcyclohexyl]valiolamine,
N-[(1S,2S)-(2,4/3,5)-2,3,4-trihydroxy-5-hydroxymethylcyclohexyl]validamine,
N-[(1R,2S)-(2,4/3,5)-2,3,4-trihydroxy-5-hydroxymethylcyclohexyl]valiolamine sulfate,
N-[(1S,2S)-(2,4/3,5)-2,3,4-trihydroxy-5-hydroxymethylcyclohexyl]valiolamine hydrochloride.
N-[(1R,2S)-(2,4/3,5)-2,3,4-tribenzyloxy-5-benzyloxymethylcyclohexyl]valiolamine,
N-[(1R,2S)-(2,4/3,5)-2,3:4,7-di-O-isopropylidene-2,3,4-trihydroxy-5-hydroxymethylcyclohexyl]valiolamine,
N-[(1R,2S)-(2,4/3,5)-4,7-O-cyclohexylidene-2,3,4-trihydroxy-5-hydroxymethylcyclohexyl]validamine,
N-[(1S,2S)-(2,4/3,5)-2,3,4-triacetoxy-5-acetoxymethylcyclohexyl]valiolamine,
N-[(1S,2S)-(2,4/3,5)-2,3,4-trihydroxy-5-trityloxymethylcyclohexyl]validamine,
N-[(1R,2S)-(2,6/3,4)-4-amino-2,3-dihydroxy-6-methylcyclohexyl]valiolamine,
N-[(1R,2S)-(2,6/3,4)-2,3,4-trihydroxy-6-methylcyclohexyl]valiolamine,
N-[(1R,2S)-(2,4/6,3)-2,3,4-trihydroxy-6-methylcyclohexyl]valiolamine,
N-[(1S,2S)-(2,6/3,4)-4-amino-2,3-dihydroxy-6-methylcyclohexyl]valiolamine,
N-[(1S,2S)-(2,6/3,4)-2,3,4-trihydroxy-6-methylcyclohexyl]valiolamine,
N-[(1S,2S)-(2,4,6/3)-2,3,4-trihydroxy-6-methylcyclohexyl]valiolamine.
4-O-α-[4-[(1S)-(1,2,4,5(OH)/3,5(CH₂OH)-(2,3,4,5-tetrahydroxy-5-(hydroxymethyl)cyclohexyl]amino]-4,6-dideoxy-D-glucopyranosyl]-D-glucopyranose,
1,6-anhydro-4-O-α-[4-[(1S)-(1,2,4,5(OH)/3,5(CH₂OH))-2,3,4,5-tetrahydroxy-5-(hydroxymethyl)cyclohexyl)amino]-4,6-dideoxy-D-glucopyranosyl]-β-D-glucopyranose,
4-O-α-[4-[(1S)-(1,2,4,5(OH)/3,5(CH₂OH)-(2,3,4,5-tetrahydroxy-5-(hydroxymethyl)cyclohexyl)amino]-4,6-dideoxy-D-galactopyranosyl]-D-glucopyranose, and
1,6-anhydro-4-O-α-[4-[(1S)-(1,2,4,5(OH)/3,5(CH₂OH)-(2,3,4,5-tetrahydroxy-5-(hydroxymethyl)cyclohexyl)amino]-4,6-dideoxy-D-galactopyranosyl]-β-D-glucopyranose, etc., [as to a nomenclature for these configurations, c.f. IUPAC-IUB 1973 Recommendation for cyclitol, Pure Appl. Chem., 37, 285 to 297 (1975).

Referring to the above-mentioned compounds the (1R,2S)-isomer generally exhibits stronger α-glucosidase inhibitory activity than the corresponding (1S,2S)-isomer.

As the protective group for the amino group in the above formulae, use is made of protective groups which are employed as amino protective groups in the chemistry of the aminosugars, aminocyclitols or peptides, such as an alkanoyl group of 1 to 5 carbon atoms which may be substituted by a halogen, exemplified by formyl, acetyl, propionyl, butyryl, trifluoroacetyl, trichloroacetyl, etc.; an aroyl group which may be substituted by nitro group, a lower alkoxy group of 1 to 4 carbon atoms or a halogen, exemplified by benzoyl, p-chlorobenzoyl, p-nitrobenzoyl, p-methoxybenzoyl, etc.; an alkoxycarbonyl group of 2 to 6 carbon atoms, exemplified by methoxycarbonyl, ethoxycarbonyl, 1-propoxycarbonyl, tert-butoxycarbonyl, etc.; an aralkyloxycarbonyl group which may be substituted by nitro group, an lower alkoxy group of 1 to 4 carbon atoms or a halogen, exemplified by benzyloxycarbonyl, p-nitrobenzyloxycarbonyl, p-methoxybenzyloxycarbonyl, 2,4-dichlorobenzyloxycarbonyl, etc.; a nitro-substituted phenyl group, exemplified by 2,4-dinitrophenyl group; phthaloyl group etc.

As the hydroxyl protective group in the above formulae, use is made of protective groups, such as acyl type protective groups, ether type protective groups, acetal type protective groups, ketal type protective groups and orthoester type protective groups, which are used in carbohydrate chemistry as the hydroxyl protective group.

As the acyl type protective groups, use is for example made of ① an alkanoyl group of 1 to 5 carbon atoms which may be substituted by a halogen, a lower alkoxy group of 1 to 4 carbon atoms or a phenoxy group which may have a halogen; ② a benzoyl group which may be substituted by nitro or phenyl group; ③ an alkoxycarbonyl group of 2 to 6 carbon atoms which may be substituted by a halogen; ④ an alkenyloxycarbonyl group of 3 to 5 carbon atoms; ⑤ a benzyloxycarbonyl group which may be substituted by alkoxy group of 1 to 4 carbon atoms or nitro group; ⑥ a nitro-substituted phenoxycarbonyl groups etc.

As the halogen mentioned above, use is made of fluorine, chlorine, bromine and iodine.

As the lower alkoxy group of 1 to 4 carbon atoms mentioned above, use is for example made of methoxyl, ethoxyl, propoxyl, butoxyl groups etc., which may be substituted by the above halogen.

As the alkanoyl group of 1 to 5 carbon atoms mentioned above, use is for example made of formyl, acetyl, propionyl, butyryl, isobutyryl, valeryl, isovaleryl, pivaloyl groups etc.

As the alkoxy group in the alkoxycarbonyl group of 2 to 6 carbon atoms mentioned above, use is for example made of an alkoxyl group of 1 to 5 carbon atoms such as methoxyl, ethoxyl, propoxyl, butoxyl, pentyloxyl, vinyloxyl, allyloxyl groups etc. which may be substituted by the above halogen.

As the alkenyl group in the alkenyloxycarbonyl group of 3 to 5 carbon atoms mentioned above, use is made of an alkenyl group of 2 to 4 carbon atoms such as vinyl, allyl, isopropenyl, 1-propenyl, 1-butenyl, 2-butenyl, 3-butenyl, etc.

More concretely, examples of the acyl type protective groups include formyl, acetyl, chloroacetyl, dichloroacetyl, trichloroacetyl, trifluoroacetyl, methoxyacetyl, triphenylmethoxyacetyl, phenoxyacetyl, p-chlorophenoxyacetyl, propionyl, isopropionyl, 3-phenylpropionyl, isobutyryl, pivaloyl; benzoyl, p-nitrobenzoyl, p-phenylbenzoyl; methoxycarbonyl, ethoxycarbonyl, 2,2,2-trichloroethoxycarbonyl, isobutyloxycarbonyl; vinyloxycarbonyl, allyloxycarbonyl; benzyloxycarbonyl, p-methoxybenzyloxycarbonyl, 3,4-dimethoxybenzyloxycarbonyl, p-nitrobenzyloxycarbonyl; p-nitrophenoxycarbonyl, etc.

As the ether type protective groups, use is for example made of ① a lower alkyl group of 1 to 5 carbon atoms which may be substituted by a halogen a lower alkoxyl group of 1 to 4 carbon atoms, benzyloxyl or phenyl group; ② an alkenyl group of 2 to 4 carbon atoms; ③ a trisubstituted silyl group which have as a substituent a lower alkyl group of 1 to 5 carbon atoms, phenyl group, benzyl group, etc; ④ a benzyl group which may be substituted by a lower alkoxyl group of 1 to 4 carbon atoms or nitro group; ⑤ a tetrahydropyranyl or tetrahydrofuranyl group which may be substituted by a lower alkoxyl group of 1 to 4 carbon atoms or a halogen, etc.

As the lower alkyl group of 1 to 5 carbon atoms mentioned above, use is for example made of methyl, ethyl, propyl, isopropyl, butyl, isobutyl, sec-butyl, tert-butyl, pentyl, isopentyl, neopentyl, etc. As the halogen, lower alkoxyl group of 1 to 4 carbon atoms and alkenyl group of 2 to 4 carbon atoms, use is made of the same as described in the case of the acyl type protective groups.

More concretely, examples of the ether type protective groups include methyl, methoxymethyl, benzyloxymethyl, tert-butoxymethyl, 2-methoxyethoxymethyl, 2,2,2-trichloromethoxymethyl, ethyl, 1-ethoxyethyl, 1-methyl-1-methoxyethyl, 2,2,2-trichloroethyl, propyl, isopropyl, butyl, isobutyl, sec-butyl, tert-butyl, ethoxyethyl, triphenylmethyl, p-methoxyphenyldiphenylmethyl; allyl; trimethylsilyl, tert-butylsilyl, tert-butyldiphenylsilyl; benzyl, p-methoxybenzyl, p-nitrobenzyl, p-chlorobenzyl; tetrahydropyranyl, 3-bromotetrahydropyranyl, 4-methoxytetrahydropyranyl, tetrahydrofuranyl, etc.

The acetal type, ketal type and orthoester type protective groups have preferably 1 to 10 carbon atoms. Specifically, their examples include methylene, ethylidene, 1-tert-butylethylidene, 1-phenylethylidene, 2,2,2-trichloroethylidene; isopropylidene, butylidene, cyclopentylidene, cyclohexylidene, cycloheptylidene; benzylidene, p-methoxybenzylidene, 2,4-dimethoxybenzylidene, p-dimethylaminobenzylidene, O-nitrobenzylidene; methoxymethylene, ethoxymethylene, dimethoxymethylene, 1-methoxyethylidene, 1,2-dimethoxyethylidene, etc.

In addition, the stannoxane type protective groups, cyclic carbonate type protective groups, cyclic boronate type protective groups, etc. are likewise employed.

As the salts of the compound [I] which fall into the scope of the present invention, use is made of a pharmaceutically acceptable addition salt of the compound [I] with acid. As the acid, use is made of an inorganic acid such as hydrochloric acid, hydrobromic acid, sulfuric acid, phosphoric acid, nitric acid etc., or an organic acid such as acetic acid, malic acid, citric acid, ascorbic acid, mandelic acid, methanesulfonic acid etc., and others.

The compound [I] or a pharmaceutically acceptable salt thereof is found to be stable crystals or powder and almost free from toxicity ($LD_{50}$ in rats, not less than 500 mg/kg).

The compound [I] or a pharmaceutically acceptable salt thereof, which possesses $\alpha$-glucosidase inhibitory activity and suppresses the metabolism of carbohydrates in man and other animals, exhibits for example the blood-sugar elevation suppressing function and is useful for hyperglycemic symptoms and various disorders caused by hyperglycemia such as obesity, adiposity, hyperlipemia (arteriosclerosis), diabetes and prediabetes as well as prophylaxis of diseases attributable to sugar metabolism by microorganisms in oral cavity such as dental caries.

The compound [I] or a pharmaceutically acceptable salt thereof can be diluted with non-toxic carriers, such as liquid carriers e.g. water, ethanol, ethylene glycol and polyethylene glycol, or solid carriers e.g. starch, cellulose and polyamide powder, and prepared into ampoules, granules, tablets, pills, capsules, syrups, etc. by a conventional manner per se known to utilize in the above-mentioned, various application fields. In addition, they can be used in combination with sweetenings, preservatives, dispersing agents and coloring agents.

The compound [I] or a pharmaceutically acceptable salt thereof, solely or as mixtures with non-toxic carriers and together with food every meals, or before or after meals, are administered orally or parenterally, preferably orally.

Specifically, preparations containing for example about 10 to 200 mg per adult human of the compound [I] or a pharmaceutically acceptable salt thereof, when given together with food every meals, or before or after meals, can suppress elevation of postprandial blood glucose level, and are therefore effective for the prophylaxis and treatment of the above-mentioned diseases. The compound [I] or a pharmaceutically acceptable salt thereof, as an $\alpha$-glucosidase inhibitor, is of value not only as medicines but also additives for livestock feed which serve to make edible animal meat low-fat, high-quality one.

The compound [I] or a pharmaceutically acceptable salt thereof may be used by adding to food products. That is to say, it may be employed with liquid or solid foods such as coffee, beverages, fruit juice, beer, milk, jam, sweet bean jam (strained or mashed bean paste boiled down with sugar) and jelly, seasoning agents or a variety of the principal and subsidiary foods.

The foods prepared by adding the compound [I] or a pharmaceutically acceptable salt thereof are suitable as food for a patient affected with metabolic abnormality and also suited for a healthy person as prophylactic food against metabolic abnormality. With reference to their amount to be added, the compound [I] or a pharmaceutically acceptable salt thereof may be added to various foods for example in the proportion within the range of 0.0001 to 1% relative to the carbohydrate content of food. In the case of blending into livestock feed, it is desirable to add it in the proportion of 0.0001 to 1% relative to the carbohydrate content of livestock feed.

The compound of the general formula [I], or a pharmaceutically acceptable salt thereof can be produced by reacting a compound of the general formula:

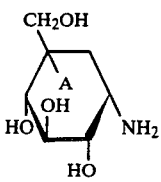 (II)

wherein A is as defined above; the hydroxyl group may be protected, with a cyclic ketone of the general formula:

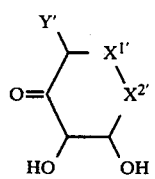 (III)

or

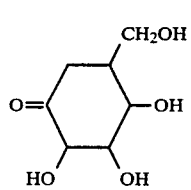 (III')

or

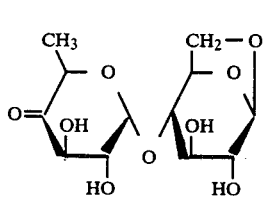 (III'')

wherein $X^{1'}$ and $X^{2'}$ are each a group represented by

, either of $X^{1'}$ and $X^{2'}$ is oxygen while the other is a group represented by

, or $X^{1'}$ and $X^{2'}$ combine to be oxygen, Y' is 1 a lower alkyl group of 1 to 4 carbon atoms which may have a hydroxyl substituent, 2 a hydroxyl group or 3 a protected amino group, and Z' is hydrogen, a hydroxyl group, a hydroxymethyl group, or a protected amino group; and the hydroxyl group may be protected, and then subjecting the resulting compound to reduction reaction, followed by cleavage of the anhydro ring bond or (and) removal of the protective group, if desired.

Referring to the above formulae, the lower alkyl group of 1 to 4 carbon atoms in the lower alkyl group of 1 to 4 carbon atoms which may have a hydroxyl substituent represented by Y' include a straight-chain or branched alkyl group of 1 to 4 carbon atoms as defined above.

As the protective group for amino group, use is made of the protective group for amino group as defined above. As the protective group for hydroxyl group, use is also made of the protective group for hydroxyl group as defined above.

As the cyclic ketone represented by the general formula [III], use is for example made of cyclic ketones having the general formula [III] where 1 Y' is a lower alkyl group of 1 to 4 carbon atoms which may have a hydroxyl substituent, $X^{1'}$ is oxygen, and $X^{2'}$ is

(Z' is a protected hydroxyl group, e.g. a lower alkoxy group of 1 to 4 carbon atoms such as methoxy, ethoxy, propoxy, butoxy etc.); 2 Y' is a lower alkyl group of 1 to 4 carbon atoms which may have a hydroxyl substituent, $X^{1'}$ is

(Z' is hydrogen), and $X^{2'}$ is

(Z' is a protected amino group); 3 Y' is a protected amino group, $X^{1'}$ is

(Z' is hydrogen), and $X^{2'}$ is

(Z' is a protected amino group); and 4 Y' is a lower alkyl group which may have a hydroxyl substituent, and $X^{1'}$ and $X^{2'}$ combine to be oxygen. Among these, more concretely, preferred exmaples are shown below (where —NH—R is a protected amino group and —OR is a protected hydroxyl group as defined above):

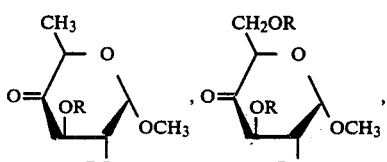

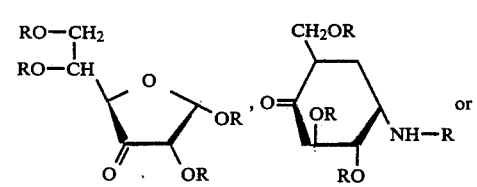

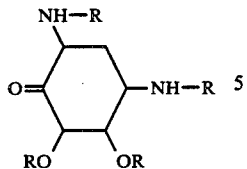

The condensation reaction of the amino group of the compound [II] with a cyclic ketone [III], [III'] or [III''] (i.e. the formation reaction of Schiff base) and the subsequent reduction reaction may be conducted in a suitable solvent. These reactions may be consecutively conducted in the same reaction vessel or may be carried out separately in two steps.

The cyclic ketone [III], [III'] or [III''] can be used normally in about 1 to 2 moles per mole of the starting compound [II] in the condensation reaction.

As the solvent in the condensation reaction of the compound [II] with a cyclic ketone [III], [III'] or [III''] and in the subsequent reduction reaction, for example, use can be made of a polar solvent such as water, alcohols e.g. methanol, propanol, butanol etc., dimethylsulfoxide, dimethylformamide, N-methylacetamide, glymes e.g. methyl cellosolve, dimethyl cellosolve, diethylene glycol dimethyl ether etc., ethers e.g. dioxane, tetrahydrofuran etc., acetonitrile, or a mixed solvent thereof or a mixture of the polar solvent with a non-polar solvent such as chloroform, dichloromethane etc.

The reaction temperature in the condensation reaction is not particularly limited, and the reaction is normally conducted at room temperature or by heating up to temperature in the neighborhood of 100° C. The reaction time varies with the reaction temperature, and the object can be normally achieved by allowing the reaction to proceed for a period of time in the range of several minutes to 24 hours.

For the reduction reaction of the Schiff base formed by the condensation reaction, use is advantageously made of a variety of metal hydride complex reducing agents, for example, borohydrides of alkali metals such as sodium borohydride, potassium borohydride, lithium borohydride, sodium trimethoxyborohydride etc., cyanoborohydrides of alkali metals such as sodium cyanoborohydride, aluminum hydrides of alkali metals such as lithium aluminum hydride, dialkylamine boranes such as dimethylamine borane, etc. In cases in which cyanoborohydrides of alkali metals such as sodium cyanoborohydride is used, it is preferable to conduct the reaction under acid conditions, for example, in the presence of hydrochloric acid, acetic acid, etc.

The reaction temperature in the reduction reaction is not particularly limited, and the reaction is conducted normally at room temperature, under ice-cooling especially in the initial stage of the reaction as the case may be, or by heating up to temperature in the neighborhood of 100° C. when occasion demands which varies depending upon the types of the Schiff bases to be reduced and reducing agents to be used.

The reaction time in the reduction reaction also varies with the reaction temperature as well as the types of the Schiff bases to be reduced and reducing agents to be used, and the object can be normally achieved by allowing the reaction to proceed for a period of time in the range of several minutes to 24 hours.

To reduce the Schiff base, use can be made of a means of catalytic reduction, as well. Namely, the reduction reaction is conducted by shaking or stirring the Schiff base in an appropriate solvent in the stream of hydrogen in the presence of a catalyst for catalytic reduction. As the catalyst for catalytic reduction, use is made for example of platinum black, platinum dioxide, palladium black, palladium carbon, Raney nickel, etc., and examples of the solvent which is normally used include water, alcohols such as methanol, ethanol etc., ethers such as dioxane, tetrahydrofuran etc., dimethylformamide or a mixed solvent thereof. The reaction is conducted normally at room temperature and at atmospheric pressure, but also may be carried out under pressure or under heating.

In cases in which the compound (I) has the protected hydroxyl groups or the protected amino group, the reaction of elimination of the hydroxyl or amino protective group can be conducted by use of per se known procedures. For example, O-cyclohexylidene, O-isopropylidene, O-benzylidene and O-trityl groups, etc. can be eliminated by hydrolysis with acids such as hydrochloric acid, acetic acid and sulfonic acid type ion exchange resins, while O-acetyl, N-ethoxycarbonyl, N-benzyloxycarbonyl and N-phthalyl groups etc. can be removed by hydrolysis with alkalis such as aqueous ammonia, barium hydroxide and hydrazine hydrate, and N-benzyloxycarbonyl groups can also be eliminated by hydrogenolysis by means of catalytic reduction.

In cases in which the compound [I] wherein B is a group of the formula:

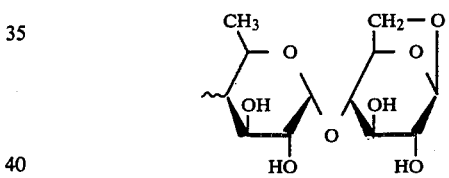

is obtained, it can be derived into the compound [I] wherein B is a group of the formula:

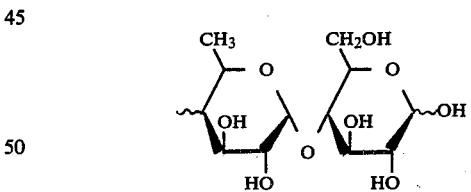

by the cleavage reaction of 1,6-anhydro ring bond as shown in following reaction equation.

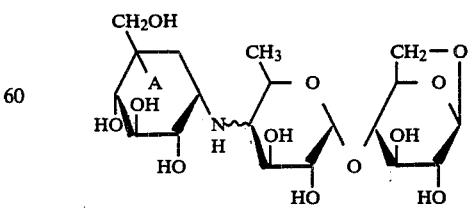

Cleavage reaction of 1,6-anhydro ring bond

-continued

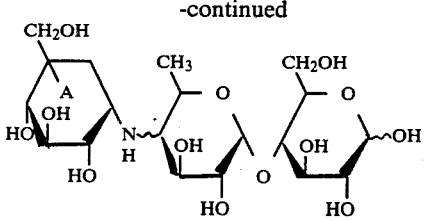

(wherein the symbols are as defined above)

The cleavage reaction of 1,6-anhydro ring bond can be carried out by acting for example a mixture of sulfuric acid, acetic anhydride and acetic acid on the compound [I] (wherein B is a group of the formula:

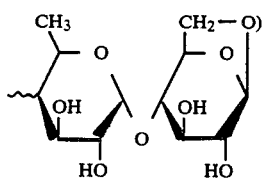

[refer to C. G. S. Dutton, et al.: Can. J. Chem., 44, 1069–1074 (1966); Mori, et al.: Chem. Pharm. Bull., 23, 1480–1487 (1975), etc.].

As the amount of sufluric acid to be used in this reaction, it is sufficient to employ the quantity in the range of the catalytic amount to twice (by weight) as much as the amount of the above starting compound. Acetic anhydride or acetic acid is normally added in large excess against the above starting compound.

This reaction is normally carried out at room temperature but may be conducted under cooling, for example under ice-cooling, as well.

The reaction time varies with the reaction temperature, but a length of time in the neighborhood of 2 hours is adequate for the reaction time. As the solvent, the above-mentioned acetic anhydride and acetic acid as the reaction agent may be added in large excess to allow them to serve as solvent at the same time, and furthermore, halogenated carbons such as dichloromethane, chloroform and carbon tetrachloride may be added. The cleavage reaction of said 1,6-anhydro ring bond can also be conducted consecutively in the same vessel together with the above condensation reaction of the compound [II] with the compound [III"] and subsequent reduction reaction. In cases in which the compound [I] is obtained in the form of a free base, a pharmaceutically acceptable salt of the compound [I] can be produced by the use of an inorganic acid such as hydrochloric acid, hydrobromic acid, sulfuric acid, phosphoric acid, nitric acid etc., or an organic acid such as acetic acid, malic acid, citric acid, ascorbic acid, mandelic acid, methanesulfonic acid, etc., in a suitable solvent in accordance with a per se known procedure.

A compound of the general formula:

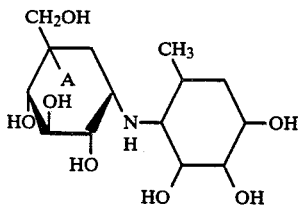

(Ia)

wherein A is hydrogen or a hydroxyl group; and the hydroxyl group may be protected, or a pharmaceutically acceptable salt thereof can be produced by reacting the compound [II] with a compound of the general formula:

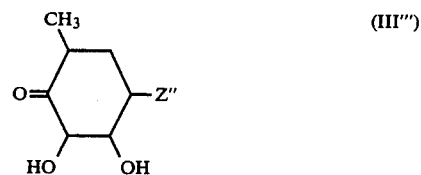

(III''')

wherein Z" is an amino group which is protected; and the hydroxyl group may be protected; and then subjecting the resulting compound to reduction reaction, followed by removal of the amino protective group, then reacting the resulting compound of the general formula:

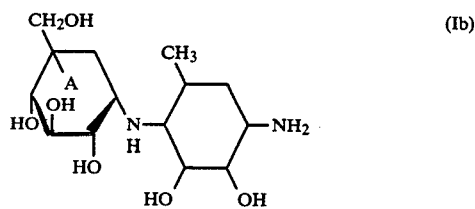

(Ib)

wherein A is as defined above; and the hydroxyl group may be protected, with an oxidative deaminating agent, and then subjecting the resulting compound of the formula:

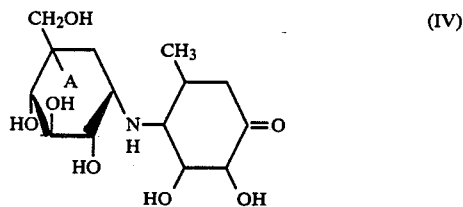

(IV)

wherein A is as defined above; and the hydroxyl group may be protected, to reduction reaction, followed by removal of the protective group, if desired. That is to say, the compound [Ia] can be produced by converting the primary amine moiety of the compound [Ib] obtained in accordance with the procedure as mentioned above, into the compound [IV] with use of an oxidative deaminating agent and then reducing the ketone moiety of the compound [IV] into the secondary hydroxyl group.

Examples of the oxidative deaminating agent include 3,5-di-tert-butyl-1,2-benzoquinone, mesitylglyoxal, 3-nitromesitylglyoxal, 3-nitromesitylglyoxal, 3,5-dinitromesitylglyoxal, etc., preferably 3,5-di-tert-butyl-1,2-benzoquinone [refer to Corey, Achiwa; Journal of The American Chemical Society, 91, 1429 to 1432 (1969)].

The above oxidative deaminating agent may be used in proportions within the range of 1 to 5 moles, preferably 1 to 3 moles, per mole of the starting compound [Ib]. The reaction is conducted normally in a suitable solvent inert to the oxidative deaminating agent.

In cases in which the hydroxyl groups are protected with protective groups, the reaction solvent varies depending upon the type of protective groups, and normally, use is made of lower alcohols of 1 to 4 carbon atoms such as methanol, ethanol etc., ethers such as tetrahydrofuran, dioxane etc., water, dimethylsulfoxide, halogenated hydrocarbons such as dichloromethane, chloroform etc., and esters of lower fatty acids such as methyl acetate, ethyl acetate etc., solely or as suitable mixtures thereof.

The reaction temperature is within the range of about $-30°$ to $80°$ C., preferably $-10°$ to $40°$ C. The reaction temperature varies with the type of reaction solvents, reaction temperature, type of oxidative deaminating agents, etc., and is normally in the range of 1 to 25 hours.

In cases in which 3,5-di-tert-butyl-1,2-benzoquinone is used as the oxidative deaminating agent, the reaction mixture is adjusted to the range of pH 1 to 5 with an aqueous solution of an inorganic acid (sulfuric acid, hydrochloric acid, etc.) or an aqueous solution of an organic acid (acetic acid, oxalic acid, etc.) in order to allow an imine intermediate (Schiff base) obtained by reaction of 3,5-di-tert-butyl-1,2-benzoquinone with the amino group of the compound [I b] to undergo prototropic isomerization and hydrolysis. Depending upon the types of oxidizing agents used, it is in some instances advantageous to employ 0.1 to 1.0 equivalent of a base such as triethylamine, sodium methoxide, potassium tert-butoxide and DBN (1,5-diazabicyclo-[4.3.0]non-5-ene) for prototropic isomerization.

The compound [Ia] can be produced by reducing the compound [IV] thus obtained with use of metal hydride complex compounds, diboranes or substituted diboranes. As the reducing agents such as metal hydride complex compounds, diboranes, substituted diboranes etc., which are used in this reaction, use is made of the same compounds as employed in the reduction reaction for the Schiff base obtained by the reaction of the compound [II] with the compound [III], [III'], [III''] or [III'''] as mentioned above. The reducing agents are used in proportions of about 1 to 10 moles, normally about 2 to 5 moles, per mole of the starting compound [IV]. The reaction is normally conducted in a suitable solvent.

As the solvent, use is for example made of a polar solvent such as water, alcohols e.g. methanol, ethanol, propanol, butanol etc., dimethylsulfoxide, dimethylformamide, N-methylacetamide, glymes e.g. methyl cellosolve, dimethyl cellosolve, diethylene glycol dimethyl ether etc., ethers e.g. dioxane, tetrahydrofuran etc., acetonitrile or a mixed solvent thereof, or a mixture of the polar solvent with a non-polar solvent such as chloroform, dichloromethane etc.

As to the temperature of this reduction reaction, the reaction is conducted normally at room temperature, under ice-cooling especially in the initial stage of the reaction as the case may be, or by heating up to temperature in the neighborhood of $100°$ C. when occasion demands, which varies depending upon the types of reducing agents and reaction solvents. The reaction temperature also varies with the reaction temperature and types of reducing agents, and is normally in the range of several minutes to 24 hours.

Furthermore, the reduction reaction of the compound [IV] into the compound [Ia] can be conducted with use of the means of catalytic reduction employed in the reduction reaction of the Schiff base obtained by the reaction of the compound [II] with the compound [III], [III'], [III''] or [III'''] as well. In cases in which the resultant compound [Ia] has the protected hydroxyl groups, the elimination reaction of the protective group can be conducted in the same manner as the above-mentioned procedure. In cases in which the compound [Ia] is obtained in the form of a free base, it can be converted into salts of the compound [Ia] with the above-mentioned inorganic or organic acid in accordance with the per se known procedures, as is the case with the compound [I].

The compound of the general formula:

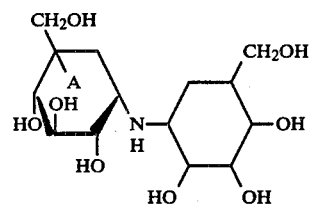

wherein A is as defined above or a pharmaceutically acceptable salt thereof can also be synthesized by the following procedure:

Namely, it can be produced by reacting the compound [II] with a cyclic alkyl halide of the general formula:

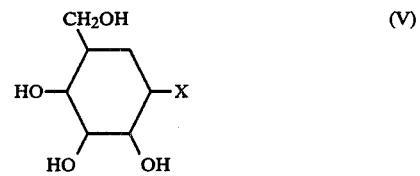

[wherein X is a halogen such as chlorine, bromine, iodine etc.; the hydroxyl group may be protected] in an appropriate solvent.

As the solvent, use is made for example of a polar solvent such as water, lower alkanols e.g. methanol, ethanol, propanol, butanol etc., ketones e.g. acetone, methyl ethyl ketone, methyl isobutyl ketone etc., dimethylsulfoxide, dimethylformamide, N-methylacetamide, glymes e.g. methyl cellosolve, ethylene glycol dimethyl ether, diethylene glycol dimethyl ether etc., ethers e.g. dioxane, tetrahydrofuran etc., acetonitrile or a mixed solvent thereof, or a mixed solvent thereof with a non-polar solvent such as benzene, hexane, chloroform, dichloromethane, ethyl acetate etc., and so forth, and when a mixed solvent does not constitute a homogeneous phase, the reaction may be conducted in the presence of a phase-transfer catalyst.

In order to accelerate the reaction, use can also be made of an inorganic base such as alkali-metal hydrogen carbonates, (e.g., sodium hydrogen carbonate), alkali-metal carbonates (e.g., sodium carbonate), alkali-metal hydroxides, etc., or an organic base such as trimethylamine, triethylamine, tributylamine, N-methylmorpholine, N-methylpiperidine, N,N-dimethylaniline, pyridine, picoline, lutidine etc.

The reaction temperature is not particularly limited, and the reaction is conducted normally at room temperature or by heating to temperature in the neighborhood of $100°$ C. The reaction time varies with the reaction temperature, and the object can be normally achieved by allowing the reaction to proceed for a period of time in the range of several minutes to 24 hours.

The compounds thus obtained and intermediates for synthesis thereof thus obtained can be isolated and purified by the means known per se such as filtration, centrifugation, concentration, concentration under reduced pressure, drying, lyophilization, adsorption, desorption, procedures utilizing the difference in solubility in a variety of solvents (e.g., solvent extraction, phasic transfer, precipitation, crystallization, recrystallization, etc.), chromatography (e.g., chromatography employing ion exchange resins, activated carbon, high-porous polymers, sephadex, sephadex ion exchange resin, cellulose, ion exchange cellulose, silica gel, alumina, etc.), and others.

The present invention provides likewise the invention relating to a compound represented by the general formula:

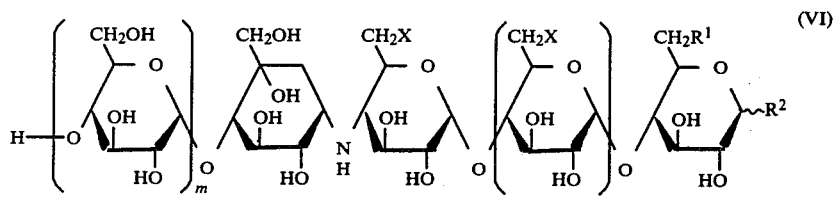

(VI)

[wherein $R^1$ and $R^2$ each represent a hydroxyl group or combine to be oxygen; n is 0 or an integer of 1 to 4; m is 0 or an integer of 1 to 3; X is hydrogen or a hydroxyl group; the chemical bond ∿ designates either the R- or/and S-configurations; the hydroxyl group may be protected], or a salt thereof. The compound of the above general formula (VI) can be produced by reacting a compound of the general formula:

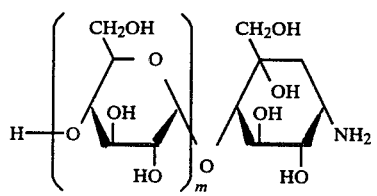

[VII]

[wherein m is 0 or an integer of 1 to 3; the hydroxyl group each may be protected] with a compound of the general formula:

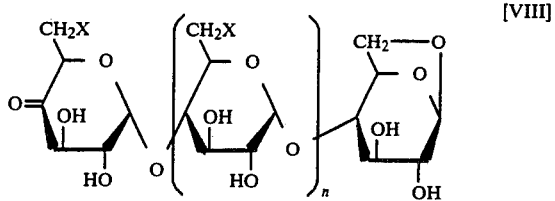

[VIII]

[wherein n is 0 or an integer of 1 to 4; X is hydrogen or a hydroxyl group; the hydroxyl group each may be protected] and reducing the resultant Schiff base, followed by cleavage of the anhydro ring bond or (and) removal of the protective group, if desired. The formation reaction of the Schiff base, reduction reaction, elimination reaction of the protective group, etc. can be carried out in the same manner as described above. Also, it is likewise produced for example by acting glucose transferases such as bacterial-saccharifing type amylase or cyclodextrin glycosyltransferase on the compound of the general formula [VI] where m is 0 and n is 0 or an integer of 1 to 4 in aqueous medium in the presence of poly-glucosides consisting of α-1,4-linked glucose units such as starch, soluble starch, dextrin, cyclodextrin and oligo-saccharides.

More concretely, examples of the compound of the general formula [VI] include:

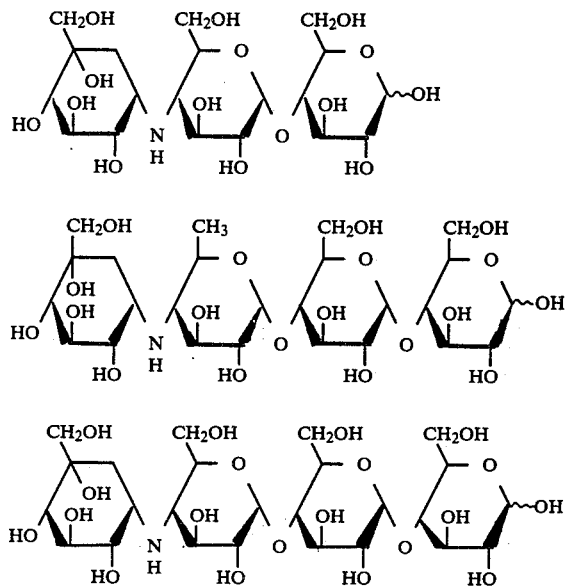

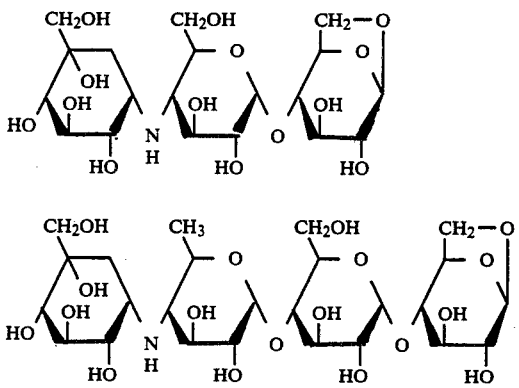

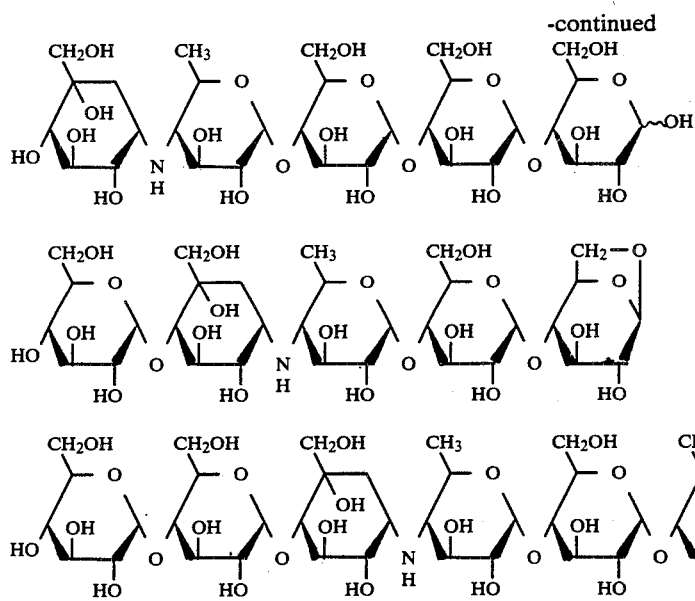

Valiolamine (the compound of the general formula [II] where A is a hydroxyl group), one of the starting compounds to be used herein, can be produced for example by the method which comprises cultivating a microorganism belonging to the genus Streptomyces as described in the Japanese Patent Application No. 55907/1981, or by the organic synthetic method with the use of valienamine or validamine as a starting material as described in the Japanese Patent Application Nos. 64370/1981 and 144309/1981. Validamine (the compound of the general formula [II] where A is hydrogen), a starting compound, is known and can be produced for example in accordance with the procedure as described in The Journal of Antibiotics, 33, 1575 to 1576 (1980).

Also, the compound of the general formula [III] can be produced for example by the procedures as illustrated in charts 1, 2 and 3.

It should be added that the N-substituted derivatives of valienamine which are synthesized by use of valienamine in place of the starting compound [II], which correspond to the compound [I], also exhibit strong α-glucosidase inhibitory activity.

chart 1

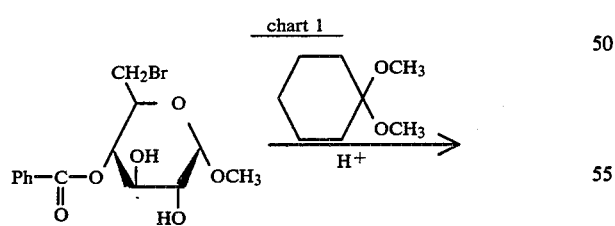

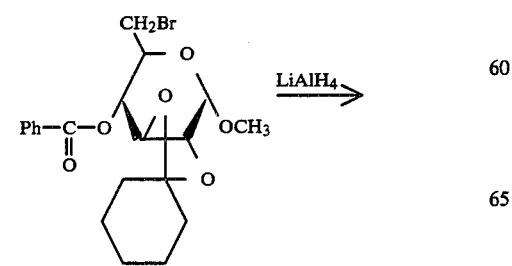

-continued

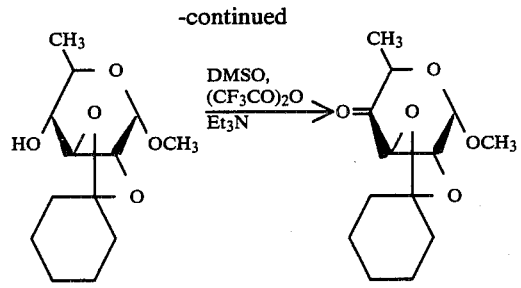

chart 2

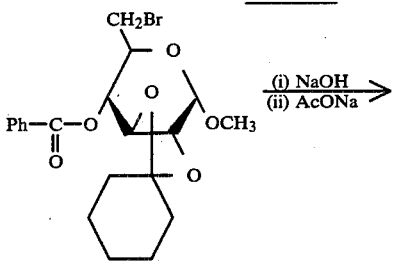

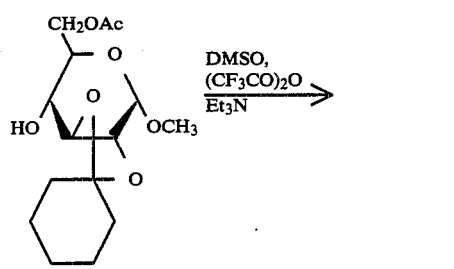

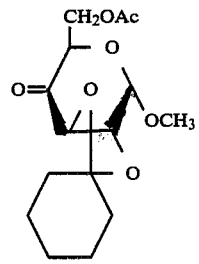

chart 3 -continued

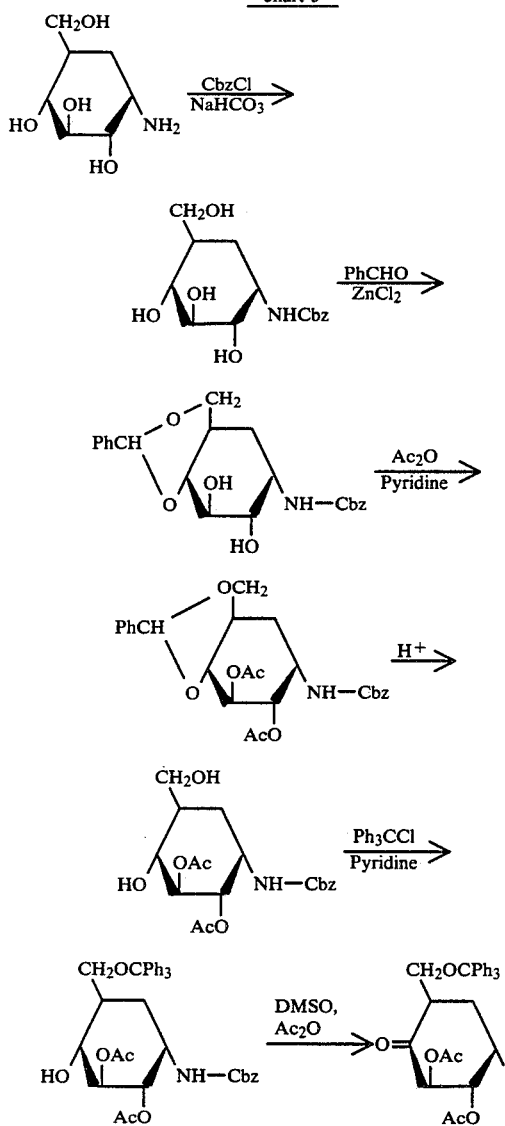

The cyclic ketone of the formula [III'], one of the starting compounds to be used in this invention, can be produced for example by oxidizing the primary amine moiety in validamine with an oxidizing agent. For example, the cyclic ketone can be produced by oxidizing the primary amine moiety in validamine with 3,5-di-tert-butyl-1,2-benzoquinone [Corey, Archiwa; Journal of The American Chemical Society, 91, 1429 to 1432 (1969] to covert into the ketone.

The cyclic ketone of the general formula [III'''] can be produced for example by the procedure as shown in chart 4 where validamine is used as a starting material. As the protective group for the amino or hydroxyl group in the formulae, besides those as shown in the below chart 4, can likewise be made of the amino protective groups (protective groups used as the amino protective groups in the chemistry of aminosugars, aminocyclitols or peptides,) and hydroxyl protective groups (e.g., acyl-type, ether-type, acetal-type and ketal-type protective groups, etc.) as mentioned above.

chart 4

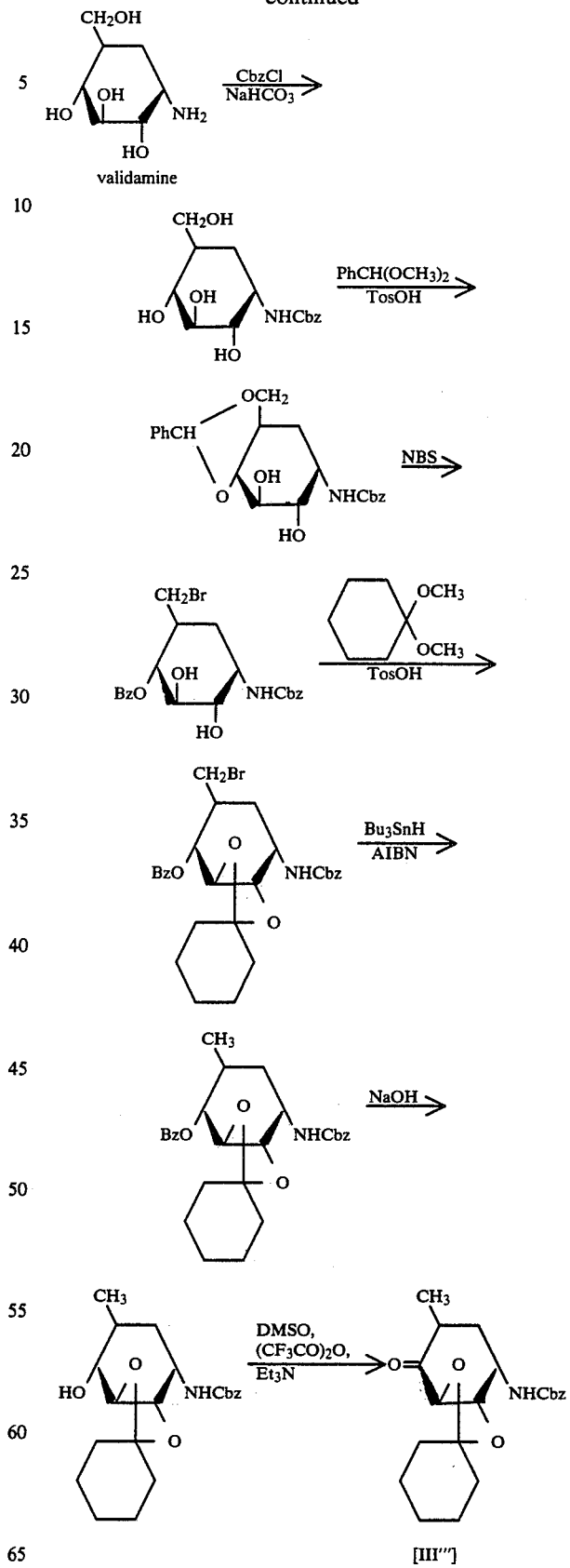

The starting compound [III''] can be produced by employing maltose as a starting material for example in accordance with the following method. For example, 2,3-di-O-benzyl-1,6-anhydro-O-(2,3-di-O-benzyl-6-deoxy-α-D-xylo-4-hexopyranoseurosyl)-β-D-glucopyranose can be produced by the method which comprises preparing 2,3-di-O-benzyl-1,6-anhydro-4-O-(2,3-di-O-benzyl-6-deoxy-α-D-glucopyranosyl)-β-D-glucopyranose from maltose by the known procedure and oxidizing the compound under acid conditions in preparing the urose by oxidation of second hydroxyl groups in sugars for example by use of dimethylsulfoxide-trifluoroacetic anhydride, in the presence of triethylamine (refer to the following scheme).

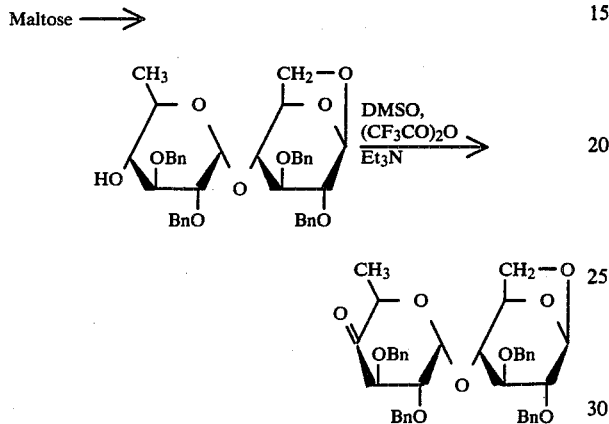

In the above formulae, the following abbreviations are used: Ac, acetyl; Ph, phenyl; Cbz, benzyloxycarbonyl; Bn, benzyl group; DMSO, dimethylsulfoxide; Tos, tosyl; NBS, N-bromosuccinimide; Bz, benzoyl; AIBN, α,α'-azoisobutyronitrile; Et, ethyl; Bu; butyl.

As the protective group of hydroxyl group in the formulae, the other group than benzyl group can be used.

Further, the cyclic alkyl halide of the general formula [V] can be produced from a cyclic alkyl compound by a per se known procedure (for example, refer to Ogawa et al.; Bulletin of The Chemical Society of Japan, 52, 1174 to 1176 (1979)). The compounds obtained can be isolated and purified by the means known per se such as filtration, centrifugation, concentration, concentration under reduced pressure, drying, lyophilization, adsorption, desorption, procedures utilizing the difference in solubility in a variety of solvents (e.g., solvent extraction, phasic transfer, precipitation, crystallization, recrystallization, etc.), chromatography (e.g., chromatography employing ion exchange resins, activated carbon, high-porous polymers, sephadex, sephadex ion exchange materials, cellulose, ion exchange cellulose, silica gel, alumina, etc.), and others.

The following Test Example, Reference Examples and Examples are intended to illustrate this invention in further detail and should by no means be construed to delimit the scope of the invention.

The mixing ratio of a mixed solvent as used in Reference Examples and Examples is indicated in volume ratio (V/V), unless otherwise indicated. In Examples 25, 26, 28, 29 and 31, the position numbers for carbon atoms of each compound in the assignment of chemical shifts of nuclear magnetic resonance spectra are utilized in accordance with the position numbers as shown in the following formula:

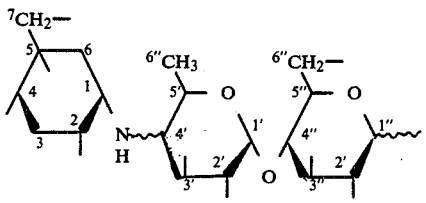

TEST EXAMPLE

The method of assaying the glucosidase inhibitory activity.

The inhibitory activities against maltase or saccharase prepared from porcine intestinal mucosa [prepared in accordance with the procedure as described by B. Borgström and A. Dahlqvist in Acta Chem. Scand., 12, 1997–2006, (1958)], when maltose or sucrose is used as a substrate, were determined by adding, to 0.25 ml of a solution of an enzyme prepared by diluting suitably with 0.02M phosphate buffer (pH 6.8), 0.5 ml of an inhibitory substance to be tested (compound [I] or a pharmaceutically acceptable salt thereof) in the same buffer and 0.25 ml of 0.05M maltose or 0.05M sucrose as the substrate in the same buffer, allowing the mixture to react at 37° C. for 10 minutes, then adding 3 ml of Glucose B-Test Reagent (a glucose oxidase reagent for measurement of glucose, produced by Wako Pure Chemical Co., Japan), further warming the mixture at 37° C. for 20 minutes and measuring the absorbance of the colored reaction solution at 505 nm.

The 50% inhibition concentration of the compound [I] or a pharmaceutically acceptable salt thereof against maltase (porcine intestinal mucose) [hereinafter referred to briefly as "$IC_{50}$ (maltase)"] or the 50% inhibition concentration thereof against saccharase (porcine intestinal mucosa) [hereinafter referred to briefly as "$IC_{50}$ (saccharase)"] were calculated from the inhibition rates (%) which were determined with respective inhibitory substance of three to five concentrations by the above-mentioned procedure.

The eluates of column chromatography in the purification step for each of the compounds as described in Reference Examples and Examples were normally subjected to analysis by thin-layer chromatography for determination of the components contained, and the eluates containing the component required to be separated were collected and subjected to the following step. Unless otherwise instructed, the Rf value by TLC for each of the compounds as described in Examples was determined by employing Precoated TLC Plate.-Silica Gel 60F$_{254}$ (produced by Merck Co., West Germany) as the thin-layer plate and n-propyl alcohol-acetic acid-water (4:1:1) as the developing solvent (the Rf values of the pseudo-aminosugar determined by the above procedure as the reference sample: Rf of valienamine=0.42, Rf of validamine=0.35 and Rf of valiolamine=0.30).

The abbreviations, as used in the Reference Examples and Examples, signify the following: s, singlet; d, doublet, dd, double doublet; t, triplet; q, quarter; dt, double triplet; m, multiplet; J, coupling constant.

REFERENCE EXAMPLE 1

N-Benzyloxycarbonylvalienamine

Valienamine (100 g) and sodium hydrogen carbonate (100 g) are dissolved in water (1 l), and a solution of benzyloxycarbonyl chloride (170 ml) in toluene (500 ml) is added dropwise to the solution under ice-cooling at 5° to 10° C., followed by stirring at the same temperature for 1 hour and then at room temperature for 3 hours. After the reaction mixture is cooled and allowed to stand at 10° C. or below, precipitated crystals of N-benzyloxycarbonylvalienamine are recovered by filtration, washed with water and toluene successively, and dried. The filtrate and washings are combined, and the water layer is separated, washed with toluene, then adjusted to pH 5 to 5.5 with 2N hydrochloric acid and concentrated to approximately 400 ml. The concentrate is allowed to stand overnight in a refrigerator, and the precipitated crystals of N-benzyloxycarbonylvalienamine are recovered by filtration, washed with cold water and then dried. Total yield of 146 g.

$[\alpha]_D^{24}$ +121.7° (c=1, $H_2O$).

Elemental analysis, for $C_{15}H_{19}NO_6$: Calcd. (%): C, 58.24; H, 6.19; N, 4.53. Found (%): C, 58.31; H, 6.17; N, 4.49.

NMR (DMSO-$d_6$) δ: 5.02 (2H, s), 5.46 (1H, d, J=5 Hz), 6.67 (1H, d, J=8.5 Hz), 7.33 (5H, s).

REFERENCE EXAMPLE 2

N-tert-Butoxycarbonylvalienamine

Valienamine (10 g) is dissolved in water (50 ml), and after addition of dioxane (50 ml), tert-butyl 4,6-dimethylpyrimidin-2-ylthiocarbonate (16.8 g) is added to the mixture, followed by stirring at room temperature for 18 hours. The reaction mixture is concentrated under reduced pressure, and the residue is dissolved in water (200 ml). The solution is washed with ethyl acetate and concentrated under reduced pressure to approximately 50 ml, and the concentrate is allowed to stand overnight in a refrigerator. The precipitated crystals are filtered out and washed with cold water. The filtrate and washings are combined and chromatographed on a column of MCI Gel CHP20P (produced by Mitsubishi Chemical Industries, Ltd., Japan) (400 ml). After the column is washed with water, elution is performed with water-80% aqueous methanol gradient. The eluate is concentrated under reduced pressure, and the concentrate is chromatographed on a column of Amberlite CG-50 (H+ type, produced by Rohm and Haas Co., U.S.A.) (550 ml), followed by elution with water. The eluate is concentrated under reduced pressure, and the concentrate is lyophilized to produce white powder (12.5 g) of N-tert-butoxycarbonylvalienamine.

$[\alpha]_D^{23}$ +128.2° (c=1, $H_2O$).

Elemental analysis, for $C_{12}H_{21}NO_6$: Calcd. (%): C, 52.35; H, 7.69; N, 5.09. Found (%): C, 52.09; H, 7.93; N, 5.02.

NMR ($D_2O$)δ: 1.58(9H, s).

REFERENCE EXAMPLE 3

9-Bromo-6,7,8-trihydroxy-1-hydroxy-1-hydroxymethyl-3-oxo-2-oxa-4-azabicyclo[3.3.1]nonane N-Benzyloxycarbonylvalienamine (146 g) is dissolved in methanol (1.2 l), to which is added dropwise a solution of bromine (75 g) in methanol (450 ml) under cooling to 0° to 5° C. The reaction mixture is stirred at the same temperature for 1 hour, and concentrated under reduced pressure. Ethanol-ethyl acetate (1:10) (2.2 l) is added to the residue, which is allowed to stand overnight in a refrigerator. The precipitated crystals are recovered by filtration, washed with ethyl acetate and petroleum ether by filtration, washed with ethyl acetate and petroleum ether successively, and dried to produce 9-bromo-6,7,8-trihydroxy-1-hydroxymethyl-3-oxo-4-azabicyclo[3.3.1]nonane (136 g). The compound is recrystallized from water.

$[\alpha]_D^{24}$ +42.1° (c−1, $H_2O$).

Elemental analysis, for $C_8H_{12}NO_6Br \cdot H_2O$: Calcd. (%): C, 30.39; H, 4.46; N, 4.43; Br, 25.28. Found (%): C, 30.31; H, 4.52; N, 4.40; Br, 25.38.

IR$\nu_{max}^{KBr}$ cm$^{-1}$: 1700 (C=O).

NMR ($D_2O$)δ: 3.66 (1H, t, J=9.3 Hz), 3.93 (1H, t, J=3.2 Hz), 3.95 (1H, d, J=13 Hz), 4.14 (1H, d, J=13 Hz), 4.18 (1H, d, J=9.3 Hz), 4.34 (1H, dd, J=3 Hz, 9.3 Hz), ~4.75 (1H).

REFERENCE EXAMPLE 4

9-Bromo-6,7,8-trihydroxy-1-hydroxymethyl-3-oxo-2-oxa-4-azabicyclo[3.3.1]nonane N-tert-Butoxycarbonylvalienamine (2.8 g) is dissolved in methanol (30 ml), to which is added dropwise a solution of bromine (1.8 g) in methanol (200 ml) under cooling in ice-water bath, followed by stirring for 1 hour. The reaction mixture is concentrated under reduced pressure, and the residue is chromatographed on a column of MCI Gel CHP 20P (produced by Mitsubishi Chemical Industries, Ltd., Japan, 250 ml), followed by elution with water. The eluate is concentrated under reduced pressure, and the concentrate is lyophilized to produce white powder (2.5 g). The white powder is added to acetic acid (40 ml), and the mixture is heated at 80° to 90° C. for 30 minutes and allowed to stand overnight at room temperature to give crystals (2.1 g) of 9-bromo-6,7,8-trihydroxy-1-hydroxymethyl-3-oxo-2-oxa-4-azabicyclo[3.3.1]nonane.

Elemental analysis, for $C_8H_{12}NO_6Br$: Calcd. (%): C, 32.23; H, 4.06; N, 4.70; Br, 26.81. Found (%): C, 32.11; H, 4.19; N, 4.87; Br, 26.67.

REFERENCE EXAMPLE 5

6,7,8-Trihydroxy-1-hydroxymethyl-3-oxo-2-oxa-4-azabicyclo[3.3.1]nonane

9-Bromo-6,7,8-trihydroxy-1-hydroxymethyl-3-oxo-2-oxa-4-azabicyclo[3.3.1]nonane (100 g) is dissolved in water (1.3 l), and sodium borohydride (55 g) is added by portions to the solution while maintaining the temperature at 25° to 30° C. The reaction mixture is stirred at the same temperature for 2 hours, then adjusted to pH 6 to 7 by adding acetic acid, and concentrated under reduced pressure to approximately 800 ml. The concentrate is chromatographed on a column of activated carbon (4.8 l), and the column is washed with water, followed by elution with 50% aqueous methanol. The eluate is concentrated under reduced pressure, and methanol (350 ml) is added to the residue, which is then refluxed for 10 to 20 minutes and allowed to stand overnight in a refrigerator. The precipitated crystals are recovered by filtration, washed with cold methanol and dried to produce 6,7,8-trihydroxy-1-hydroxymethyl-3-oxo-2-4-azabicyclo[3.3.1]nonane (64 g).

$[\alpha]_D^{24}$+35.0° (c=1, $H_2O$).

Elemental analysis, for $C_8H_{13}NO_6$: Calcd. (%): C, 43.83; H, 5.98; N, 6.39. Found (%): C, 43.80; H, 5.96; N, 6.52.

IR $\nu_{max}^{KBr}$ cm$^{-1}$: 1670 (C=O).
NMR (D$_2$O)δ: 2.07(1H, dd, J=2 Hz, 15 Hz), 2.34(1H, dd, J=5 Hz, 15 Hz), 3.45–4.1(6H).
m.p. 254°–255° C. (decomp.).

REFERENCE EXAMPLE 6

9-Iodo-1-hydroxymethyl-6,7,8-trihydroxy-3-oxo-2-oxa-4-azabicyclo[3.3.1]nonane (a) A 50 ml portion of a methanol solution of 3.1 g of N-benzyloxycarbonylvalienamine and 20 ml of a methanol solution of 2.6 g of iodine are simultaneously added dropwise to 20 ml of methanol cooled to 5° to 10° C. The reaction mixture is stirred at room temperature for 25 hours, and concentrated under reduced pressure. The residue is added to a mixture of ethyl acetate and water to allow the distribution, and the water layer is separated. The water extract is washed with ethyl acetate and concentrated under reduced pressure, and the residue is chromatographed on a column of MCI Gel CHP20P (250 ml, produced by Mitsubishi Chemical Industries, Ltd., Japan), followed by elution with water. The eluate is concentrated under reduced pressure and lyophilized to give 1.1 g of 9-iodo-1-hydroxymethyl-6,7,8-trihydroxy-3-oxo-2-oxa-4-azabicyclo[3.3.1]nonane.

(b) A 20 ml portion of an acetonitrile solution of 1.7 g of iodine monochloride is added dropwise to 50 ml of a methanol solution of 3.1 g of N-benzyloxycarbonylvalienamine cooled to 0° to 5° C., and the solution is stirred at 0° to 5° C. for 5 hours and further at room temperature for 15 hours. The reaction mixture is concentrated under reduced pressure, and the residue is added to a mixture of ethyl acetate and water to allow the distribution. The water layer is separated, then washed with ethyl acetate, adjusted to pH 5 with saturated aqueous sodium hydrogen carbonate, and concentrated under reduced pressure. The residue is chromatographed on a column of MCI Gel CHP20P (25 ml, produced by Mitsubishi Chemical Industries, Ltd., Japan), and elution is performed with water. The eluate is concentrated under reduced pressure, and the residue is dissolved under heating in a small amount of water. The solution is allowed to stand overnight in a refrigerator to give crystalline 9-iodo-1-hydroxymethyl-6,7,8-trihydroxy-3-oxo-2-oxa-4-azabicyclo[3.3.1]nonane (3.1 g).
$[\alpha]_D^{24}+37.5°$ (c=1, H$_2$O).
Elemental analysis, for C$_8$H$_{12}$NO$_6$I.H$_2$O: Calcd. (%): C, 26.46; H, 3.89; N, 3.86. Found (%): C, 26.57; H, 3.97; N, 3.96.
IR $\nu_{max}^{KBr}$ cm$^{-1}$: 1680 (C=O).
NMR (D$_2$O)δ: 3.70(1H, t, J=9.5 Hz), 3.92(1H, t, J=3.5 Hz), 4.02 and 4.28(each, 1H, d, J−15 Hz), 4.33(1H, d, J=9.5 Hz), 4.53(1H, dd, J=3.5 Hz, 9 Hz), 4.79(1H, d, J=3.5 Hz).

REFERENCE EXAMPLE 7

1L(1S)-(1(OH),2,4,5/1,3)-5-amino-1-hydroxymethyl-1,2,3,4-cyclohexanetetraol (valiolamine)

6,7,8-Trihydroxy-1-hydroxymethyl-3-oxo-2-oxa-4-azabicyclo[3.3.1]nonane (50 g) is dissolved in water (1.5 l), and barium hydroxide (200 g) is added to the solution, followed by stirring under heating at 70° to 80° C. for 3 hours. After the reaction mixture is cooled to 20° C., carbon dioxide gas is introduced into the reaction mixture for 30 minutes and the resultant precipitates are filtered out and washed with water. The filtrate and washings are combined and chromatographed on a column of Amberlite CG-50 (NH$_4$$^+$ type, produced by Rohm & Haas Co., U.S.A., 1.6 l). The column is washed with water (1 l), and elution is performed with 0.2N aqueous ammonia. The eluate is concentrated under reduced pressure to approximately 200 ml, and the concentrate is chromatographed on a column of Dowex 1×2 (OH$^-$ type, produced by Dow Chemical Co., U.S.A., 1.6 l), followed by elution with water. The eluate is concentrated under reduced pressure and lyophilized to give white powdery valiolamine (42.7 g).
$[\alpha]_D^{25}+19.6°$ (c=1, H$_2$O).
Elemental analysis, for C$_7$H$_{15}$NO$_5$.H$_2$O: Calcd. (%): C, 39.80; H, 8.11; N, 6.63. Found (%): C, 39.87; H, 8.13; N, 6.68.
NMR (D$_2$O)δ: 1.80(1H, dd, J=3.3 Hz, 15.5 Hz), 2.07(1H, dd, J=3 Hz, 15.5 Hz), 3.4–3.6(1H), 3.55(1H, d, J=10 Hz), 3.63(2H), 3.72(1H, dd, J=4.2 Hz, 10 Hz), 3.99(1H, t, J=10 Hz).

REFERENCE EXAMPLE 8

Methyl 4-O-benzoyl-2,3-O-cyclohexylidene-6-bromo-6-deoxy-α-D-glucopyranoside

Methyl 4-O-benzoyl-6-bromo-6-deoxy-α-D-glucopyranoside (25 g) is dissolved in dimethylformamide (50 ml), and 1,1-dimethoxycyclohexane (50 ml) and p-toluenesulfonic acid (1.0 g) are added to the solution, followed by stirring at 55° C. for 5 hours under reduced pressure (40 mmHg) with suction through an aspirator. The reaction mixture is concentrated under reduced pressure (18 to 20 mmHg) at the same temperature for 30 minutes. The residue is added to a mixture of ethyl acetate and water to allow the distribution. The ethyl acetate layer is separated, washed with saturated aqueous sodium hydrogen carbonate, dried over sodium sulfate and concentrated under reduced pressure. The residue is chromatographed on a column of silica gel (600 ml), and the column is washed with toluene, followed by elution with toluene-ethyl acetate (9:1). The eluate is concentrated under reduced pressure and dried overnight in a desiccator under reduced pressure to give syrupy methyl 4-O-benzoyl-2,3-O-cyclohexylidene-6-bromo-6-deoxy-α-D-glucopyranoside (26 g).
Elemental analysis, for C$_{20}$H$_{25}$O$_6$Br: Calcd. (%): C, 54.43; H, 5.71; Br, 18.11. Found (%): C, 54.99; H, 5.96; Br, 18.56.

REFERENCE EXAMPLE 9

Methyl 2,3-O-cyclohexylidene-6-deoxy-α-D-glucopyranoside

Methyl 4-O-benzoyl-2,3-O-cyclohexylidene-6-bromo-6-deoxy-α-D-glycopyranoside (5.0 g) is dissolved in tetrahydrofuran (50 ml), and lithium aluminum hydride (1.0 g) is added to the solution under cooling in ice-water bath, followed by stirring for 30 minutes, and further stirring under reflux for 2 hours. The reaction mixture is again cooled with ice-water bath, and water is added to the mixture, followed by concentrating under reduced pressure. The residue is added to a mixture of ethyl acetate and water, which is adjusted under stirring to pH 2 or less with 2N hydrochloric acid. The ethyl acetate layer is separated, washed with saturated aqueous sodium hydrogen carbonate, dried over sodium sulfate and concentrated under reduced pressure. The residue is chromatographed on a column of silica gel (250 ml), and elution is performed with toluene-ethyl acetate (3:1). The eluate is concentrated under reduced pressure and dried overnight in a desiccator under reduced pressure to give syrupy methyl 2,3-O-cyclohexylidene-6-deoxy-α-D-glycopyranoside (2.8 g).

$[\alpha]_D^{24}$ +88.6° (c−1, CH$_3$OH).

Elemental analysis, for C$_{13}$H$_{22}$O$_5$: Calcd. (%): C, 60.44; H, 8.59. Found (%): C, 60.25; H, 8.52.

NMR (CDCl$_3$)δ: 1.30(3H, d, J=6 Hz), 1.25–1.9(10H, m), 2.98(1H, d, J=3 Hz), 3.43(3H, s), 3.3–3.65(3H, m), 3.93(1H, t, J=9.5 Hz), 4.96(1H, d, J=3 Hz).

REFERENCE EXAMPLE 10

Methyl 2,3-O-cyclohexylidene-6-deoxy-α-D-xylo-hexopyranoside-4-urose(methyl 2,3-O-cyclohexylidene-6-deoxy-α-D-xylo-4-hexopyranoseuroside)

A solution of trifluoroacetic anhydride (11.1 ml) in dichloromethane (20 ml) is added dropwise to a solution of dimethylsulfoxide (7.5 ml) in dichloromethane (20 ml) under cooling at −65° C. or below, and the solution is stirred at the same temperature for 10 minutes. A solution of methyl 2,3-O-cyclohexylidene-6-deoxy-α-D-glucopyranoside (6.8 g) in dichloromethane (30 ml) is added dropwise to the reaction mixture under cooling at −70° C. or below, followed by stirring at the same temperature for 1 hour. After triethylamine (22.2 ml) is added to the reaction mixture under cooling at −65° C. or below, the cooling bath is removed, and stirring is continued until the reaction temperature reaches 20° C. The reaction mixture is poured into a mixture of ice-water and dichloromethane, and the dichloromethane layer is separated, washed with 2N hydrochloric acid and saturated aqueous sodium hydrogen carbonate successively, dried over sodium sulfate and freed of the solvent. The residue is chromatographed on a column of silica gel (400 ml), and the elution is performed with toluene-ethyl acetate (17:3). The eluate is concentrated under reduced pressure, and the residue is dried overnight in a desiccator under reduced pressure to produce crystalline methyl 2,3-O-cyclohexylidene-6-deoxy-α-D-xylo-hexopyranoside-4-urose (5.3 g).

$[\alpha_D^{24}$ +143.3° (c=1, CH$_3$OH).

Elemental analysis, for C$_{13}$H$_{20}$NO$_5$: Calcd. (%): C, 60.92; H, 7.87. Found (%): C, 60.82; H, 8.09.

NMR (CDCl$_3$)δ: 1.31 (3H, d, J=7 Hz), 1.2–2.0 (10H, m), 3.57 (3H, s), 3.78 (1H, dd, J=3 Hz, 11 Hz), 4.16 (1H, q, J=7 Hz), 4.79 (1H, d, J=11 Hz), 5.19 (1H, d, J=3 Hz).

IR $\nu_{max}^{Nujol}$ cm$^{-1}$: 1760 (C=O).

REFERENCE EXAMPLE 11

Methyl 6-O-acetyl-2,3-O-cyclohexylidene-α-D-glucopyranoside

Methyl 4-O-benzoyl-6-bromo-6-deoxy-α-D-glucopyranoside (27 g) is dissolved in dimethylformamide (50 ml), and 1,1-dimethoxycyclohexane (40 ml) and p-toluenesulfonic acid (1.4 g) are added to the solution, followed by stirring, under reduced pressure (40 to 45 mmHg) with suction through an aspirator, at 55° C. for 3 hours. The reaction mixture is poured into a mixture of ethyl acetate (600 ml) and water (300 ml), and the ethyl acetate layer is separated, washed with saturated aqueous sodium hydrogen carbonate, dried over sodium sulfate and concentrated under reduced pressure. The residue is dissolved in a solution consisting of a mixture of tetrahydrofuran (350 ml), methanol (200 ml) and 1N sodium hydroxide (100 ml), and after stirring at room temperature for 1 hour, the reaction mixture is concentrated under reduced pressure. Water (250 ml) is added to the residue, and the oily resultant substance is extracted with ethyl acetate. The ethyl acetate extract is washed with water, dried over sodium sulfate and concentrated under reduced pressure to produce syrupy methyl 2,3-O-cyclohexylidene-6-bromo-6-deoxy-α-D-glucopyranoside (20 g). The syrupy substance (20 g) thus obtained is dissolved in dimethylformamide (250 ml), and sodium acetate (14 g) is added to the solution, followed by stirring at 80° to 85° C. for 40 hours. The reaction mixture is concentrated under reduced pressure, and the residue is added to a mixture of ethyl acetate (600 ml) and water (300 ml). The ethyl acetate layer is separated, washed with 1N hydrochloric acid and saturated aqueous sodium hydrogen carbonate successively, dried over sodium sulfate and concentrated under reduced pressure. The residue is chromatographed on a column of silica gel (500 ml), and the column is subjected to elution with toluene-ethyl acetate (5:1). The eluate is concentrated under reduced pressure and dried overnight in a desiccator under reduced pressure to produce syrupy methyl 6-O-acetyl-2,3-O-cyclohexylidene-α-D-glucopyranoside (10.5 g).

$[\alpha]_D^{24}$ +97.2° (c=1, CH$_3$OH).

Elemental analysis, for C$_{15}$H$_{24}$O$_7$: Calcd.(%): C, 56.95; H, 7.65. Found (%): C, 57.34; H, 7.87.

NMR (CDCl$_3$)δ: 1.2–1.9 (10H, m), 2.11 (3H, s), 3.14 (1H, d, J=3.3 Hz), 3.46 (3H, s), 3.4–4.65 (6H, m), 5.06 (1H, d, J=3 Hz).

REFERENCE EXAMPLE 12

Methyl 6-O-acetyl-2,3-O-cyclohexylidene-α-D-xylohexopyranoside-4-urose (methyl 6-O-acetyl-2,3-O-cyclohexylidene-α-D-xylo-4-hexopyranoseuroside)

A solution of trifluoroacetic anhydride (13.9 ml) in dichloromethane (50 ml) is added dropwise to a solution of dimethylsulfoxide (9.3 ml) in dichloromethane (50 ml) under cooling at −65° C. or below, followed by stirring at the same temperature for 10 minutes. A solution of methyl 6-O-acetyl-2,3-O-cyclohexylidene-α-D-glucopyranoside (10.4 g) in dichloromethane (70 ml) is added dropwise to the reaction mixture under cooling at −70° C. or below, and after stirring at the same temperature for 1 hour, a solution of triethylamine (27.6 ml) in dichloromethane (40 ml) is added dropwise to the reaction mixture. After the cooling bath is removed and stirring is continued until the reaction temperature reaches 20° C., ice-cold water is added to the reaction mixture. The dichloromethane layer is separated, and the water layer is extracted with dichloromethane. The dichloromethane extracts are collected, washed with 2N hydrochloric acid and saturated aqueous sodium hydrogen carbonate successively, dried over sodium sulfate and concentrated under reduced pressure. The residue is chromatographed on a column of silica gel (400 ml), and elution is performed with toluene-ethyl acetate (5:1). The eluate is concentrated under reduced pressure, and the residue is dried overnight in a desiccator under reduced pressure to produce syrupy methyl 6-acetyl-2,3-O-cyclohexylidene-α-D-xylo-hexopyranoside-4-urose.

$[\alpha]_D^{24}$ +120.4° (c=1, CH$_3$OH).

Elemental analysis, for $C_{15}H_{22}O_7$: Calcd.(%): C, 57.31; H, 7.06. Found (%): C, 57.60; H, 7.32.

NMR (CDCl$_3$)δ: 1.2–1.85 (10H, m), 2.04 (3H, s), 3.56 (3H, s), 3.82 (1H, dd, J=3 Hz, 11 Hz), 4.15–4.7 (3H, m), 4.78 (1H, d, J=11 Hz), 5.27 (1H, d, J=3 Hz).

IR $\nu_{max}^{Nujol}$ cm$^{-1}$: 1765, 1750.

REFERENCE EXAMPLE 13

4,7-O-Benzylidene-N-benzyloxycarbonylvalidamine

N-Benzyloxycarbonylvalidamine (as described in Reference Example 1 of the Japanese Patent Application No. 144309/1981, pp. 30) (20 g) is suspended in benzaldehyde (50 ml), and zinc chloride (10 g) is added to the suspension, followed by stirring at room temperature for 5 hours. The reaction mixture is added to a mixture of ethyl acetate and water, and the ethyl acetate layer is separated, washed with saturated aqueous sodium hydrogen carbonate, dried over sodium sulfate and concentrated under reduced pressure. Petroleum ether (800 ml) is added to the residue, which is allowed to stand overnight at room temperature. The oily resultant substance is separated and chromatographed on a column of silica gel (550 ml), followed by elution with toluene-acetone (2:1). The eluate is concentrated under reduced pressure, and the residue is treated with petroleum ether to produce 4,7-O-benzylidene-N-benzyloxycarbonylvalidamine (21.1 g).

$[\alpha]_D^{24}$+54.1° (c=1, CH$_3$OH).

Elemental analysis, for $C_{22}H_{25}NO_6$: Calcd. (%): C, 66.15; H, 6.31; N, 3.51. Found (%): C, 66.09; H, 6.16; N, 3.28.

NMR (DMSO-d$_6$)δ: 0.8–2.2 (3H, m), 3.1–4.2 (6H, m), 4.70 (1H, d, J=5 Hz), 4.78 (1H, d, J=4.5 Hz), 5.02 (2H, s), 5.47 (1H, s), 6.98 (1H, d, J=7.5 Hz), 7.2–7.6 (10H, m).

REFERENCE EXAMPLE 14

2,3-Di-O-acetyl-4,7-O-benzylidene-N-benzyloxycarbonylvalidamine 4,7-O-Benzylidene-N-benzyloxycarbonylvalidamine (15 g) is dissolved in a mixture of pyridine (150 ml) and acetic anhydride (75 ml), and the solution is stirred overnight at room temperature. The reaction mixture is concentrated under reduced pressure, and the residue is added to a mixture of ethyl acetate and water. The ethyl acetate layer is separated, washed with 2N hydrochloric acid and saturated aqueous sodium hydrogen carbonate successively, dried over sodium sulfate and concentrated under reduced pressure. The residue is treated with petroleum ether to produce 2,3-di-O-acetyl-4,7-O-benzylidene-N-benzyloxycarbonylvalidamine (18.5 g).

$[\alpha]_D^{24}$+18.5° (c=1, CH$_3$OH).

Elemental analysis, for $C_{26}H_{29}NO_8$: Calcd.(%): C, 64.58; H, 6.05; N, 2.90. Found (%): C, 64.56; H, 6.13; N, 2.81.

NMR (CDCl$_3$)δ: 1.94 (3H, s), 2.02 (3H, s), 3.44 (1H, dd, J=3 Hz, 10Hz), 3.58 (1H, dd, J=4.5 Hz, 10 Hz), 4.12 (1H, dd, J=4.5 Hz, 11 Hz), 4.35 (1H), 4.95 (1H, dd, J=4 Hz, 10 Hz), 5.10 (2H, s), 5.37 (1H, t, J=10 Hz), 5.47 (1H, s), 7.37 (10H, s).

REFERENCE EXAMPLE 15

2,3-Di-O-acetyl-N-benzyloxycarbonylvalidamine 2,3-Di-O-acetyl-4,7-O-benzylidene-N-benzyloxycarbonylvalidamine (18 g) is dissolved in methanol (440 ml), and 0.5N hydrochloric acid (130 ml) is added to the solution, followed by stirring under reflux for 30 minutes. The reaction mixture is cooled to room temperature, adjusted to pH 5.0 with saturated aqueous sodium hydrogen carbonate, and concentrated under reduced pressure. The residue is added to a mixture of ethyl acetate and water to allow the distribution, and the ethyl acetate layer is separated, washed with water, dried over sodium sulfate and concentrated under reduced pressure. The residue is treated with ethyl ether-petroleum ether (1:5) (approximately 1 l) to produce 2,3-di-O-acetyl-N-benzyloxycarbonylvalidamine (11.0 g).

$[\alpha]_D^{24}$+54.8° (c=1, CH$_3$OH).

Elemental analysis, for $C_{19}H_{25}NO_8$: Calcd.(%): C, 57.71; H, 6.37; N, 3.54. Found (%): C, 57.67; H, 6.49; N, 3.67.

NMR (CDCl$_3$)δ: 5.09 (2H, s), 7.36 (5H, s).

REFERENCE EXAMPLE 16

2,3-Di-O-acetyl-N-benzyloxycarbonyl-7-O-tritylvalidamine 2,3-Di-O-acetyl-N-benzyloxycarbonylvalidamine (11.0 g) is dissolved in pyridine (180 ml), and trityl chloride (15 g) is added to the solution, followed by stirring overnight at room temperature. The reaction mixture is added to a mixture of ethyl acetate and water, and the ethyl acetate layer is separated, washed with 5% aqueous phosphoric acid and 5% aqueous sodium hydrogen carbonate successively, dried over sodium sulfate and concentrated under reduced pressure. The residue is chromatographed on a column of silica gel (450 ml), and elution is performed with toluene-ethyl acetate (3:1). The eluate is concentrated under reduced pressure, and the residue is treated with ethyl ether-petroleum ether (1:2), which is allowed to stand overnight in a refrigerator to produce crystalline 2,3-di-O-acetyl-N-benzyloxycarbonyl-7-O-tritylvalidamine (11.4 g).

$[\alpha]_D^{25}$+57.6° (c=1, DMF).

Elemental analysis, for $C_{38}H_{39}NO_8$: Calcd.(%): C, 71.57; H, 6.16; N, 2.20. Found (%): C, 71.74; H, 6.22; N, 2.12.

NMR (CDCl$_3$)δ: 1.87 (3H, s), 2.03 (3H, s), 2.98 (1H, d, J=5 Hz), 3.0–3.8 (3H, m), 4.15–4.5 (1H, m), 4.82 (1H, dd, J=4 Hz, 10 Hz), 5.07 (2H, s), 5.17 (1H, t, J=10 Hz), 7.15–7.55 (20H, m).

REFERENCE EXAMPLE 17

(2R)-(2,6/3,4)-2,3-Diacetoxy-4-benzyloxycarbonylamino-6-trityloxymethylcyclohexanone 2,3-Di-O-acetyl-N-benzyloxycarbonyl-7-O-tritylvalidamine (6.4 g) is dissolved in a mixture of dimethylsulfoxide (40 ml) and acetic anhydride (20 ml), followed by stirring at room temperature for 15 hours. The reaction mixture is added to a mixture of ice-cold water and ethyl acetate, and the ethyl acetate layer is separated, while the water layer is extracted with ethyl acetate. The ethyl acetate extracts are collected, washed with 5% aqueous phosphoric acid and 5% aqueous sodium hydrogen carbonate successively, dried over sodium sulfate and freed of the solvent under reduced pressure. The residue is treated with ethyl ether-petroleum ether (1:20) (315 ml) to produce (2R)-(2,6/3,4)-2,3-diacetoxy-4-benzyloxycarbonylamino-6-trityloxymethylcyclohexanone (5.7 g).

$[\alpha]_D^{25}$+56.4° (c=1, DMF).

Elemental analysis, for $C_{38}H_{37}NO_8$: Calcd. (%): C, 71.39; H, 5.87; N, 2.20. Found (%): C, 71.71; H, 5.66; N, 2.08.

NMR (CDCl$_3$)δ: 1.4–2.8 (3H, m), 1.94 (3H, s), 2.08 (3H, s), 3.1–3.6 (2H, m), 4.4–4.7 (1H, m), 5.05 (1H, dd, J=4 Hz, 12 Hz), 5.12 (2H, s), 5.43 (1H, d, J=12 Hz), 5.77 (1H, d, J=8 Hz), 7.15–7.55 (20H, m).

REFERENCE EXAMPLE 18

Mixture of N,N'-diethoxycarbonyl-4,5-O-isopropylidene-6-oxo-2-deoxystreptamine and N,N'-diethoxycarbonyl-5,6-O-isopropylidene-4-oxo-2-deoxystreptamine A mixture (11.0 g) of N,N'-diethoxycarbonyl-4,5-O-isopropylidene-2-deoxystreptamine and N,N'-diethoxycarbonyl-5,6-O-isopropylidene-2-deoxystreptamine is dissolved in chloroform (100 ml), and water (90 ml) is added to the solution. Potassium periodate (15.0 g) and potassium carbonate (15.0 g), and then ruthenium dioxide (400 mg) are added to the mixture, which is stirred at room temperature for 15 hours. 2-Propanol (10 ml) is added to the reaction mixture, which is stirred at room temperature for 30 minutes.

The reaction mixture is subjected to filtration to remove an insoluble matter, which is washed with chloroform. The filtrate and washings are combined, and the chloroform layer is separated, while the water layer is extracted with dichloromethane. The organic layers are combined, dried over magnesium sulfate and freed of the solvent under reduced pressure. Ethyl ether (30 ml) and petroleum ether (100 ml) are added to the residue, which is allowed to stand overnight in a refrigerator to give crystals (8.0 g) of the titled oxo-derivative.

m.p.: 184° C. (decomp.).

Elemental analysis, for $C_{15}H_{24}N_2O_7$: Calcd.(%): C, 52.32; H, 7.03; N, 8.14. Found: (%): C, 52.08; H, 7.13; N, 7.82.

NMR (CDCl$_3$)δ: 1.23 (6H, t, J=7 Hz), 1.47 (6H, s), 2.75–3.15 (1H, m), 3.64 (1H, t, J=10 Hz), 4.01 (2H, q, J=7 Hz), 4.03 (2H, q, J=7 Hz), 4.37 (1H, dd, J=1 Hz, 10 Hz), 5.05 (1H, d, J=7.5 Hz), 5.56 (1H, d, J=7.5 Hz).

REFERENCE EXAMPLE 19

(1R)-(1(CH$_2$OH),2,4,5/1(OH),3)-5-Amino-1-hydroxymethyl-1,2,3,4-cyclohexanetetrol (the 5-epimer of valiolamine)

(1R)-(1,3,4/2)-Tri-O-acetyl-4-benzyloxycarbonylamino-6-exomethylene-1,2,3-cyclohexanetriol (as described in Reference Example 5 of the Japanese Patent Application No. 144309/1981, pp. 35) (3.8 g) is dissolved in ethyl ether (50 ml), and after addition of pyridine (3 ml), a solution of osmium tetroxide (2.4 g) in ethyl ether (20 ml) is added dropwise to the mixture under cooling in an ice-cold water bath. The reaction mixture is stirred at room temperature for 4 hours and then allowed to stand overnight at room temperature. After the reaction mixture is cooled by ice-cold water for 2 hours, the resultant precipitates are recovered by filtration, washed with cold ethyl ether and dried. The precipitate (2.8 g) thus obtained is dissolved in ethanol (50 ml), and water (100 ml) and then sodium sulfite (14 g) is added to the solution, followed by stirring at room temperature for 20 hours. The resulting black precipitates are filtered out and washed with ethanol, and the filtrate and washings are combined and freed of the solvent under reduced pressure. The residue is added to a mixture of ethyl acetate and water to allow the distribution, and the ethyl acetate layer is separated, while the water layer is extracted three times with ethyl acetate. The ethyl acetate layers are combined, washed with water, dried over sodium sulfate and concentrated under reduced pressure to produce (1R)-(1(CH$_2$OH),2,4,5/1(OH),3)-2,3,4-tri-O-acetyl-5-benzyloxycarbonylamino-1-hydroxymethyl-1,2,3,4-cyclohexanetetrol as an oily substance (2.0 g). The oily substance is dissolved in methanol-water-acetic acid (1:1:0.2) (70 ml), and palladium black (500 mg) is added to the solution, followed by stirring under a stream of hydrogen at room temperature for 2.5 hours. The catalyst is filtered out and washed with 50% aqueous methanol, and the filtrate and washings are combined and concentrated under reduced pressure to dryness. The residue is dissolved in 1N aqueous sodium hydroxide (100 ml), and the solution is stirred at room temperature for 3 hours. The reaction mixture is adjusted to pH 5 with 2N hydrochloric acid and chromatographed on a column of Amberlite CG-50 (NH$_4^+$ type, produced by Rohm & Haas Co., U.S.A.) (250 ml), and the column is washed with water, followed by elution with 0.2N aqueous ammonia. The eluate is concentrated under reduced pressure and lyophilized to produce white powdery (1R)-(1(CH$_2$OH),2,4,5/1(OH),3)-5-amino-1-hydroxymethyl-1,2,3,4-cyclohexanetetrol (400 mg).

$[\alpha]_D^{23}$ +17.5° (c=1, H$_2$O).

Elemental analysis, for $C_7H_{15}NO_5 \cdot H_2O$: Calcd.(%): C, 39.80; H, 8.11; N, 6.63. Found (%): C, 40.11; H, 8.04; N, 6.92.

NMR (D$_2$O)δ: 1.88 (1H, dd, J=4.5 Hz, 14.5 Hz), 2.14 (1H, dd, J=7 Hz, 14.5 Hz), 3.5–4.1 (5H, m), 4.17 (1H, t, J=6.5 Hz).

TLC: Rf=0.42

REFERENCE EXAMPLE 20

3-O-Benzyloxycarbonyl-4,7-O-isopropylidenevalienamine 1,2-carbamate (a) N-Benzyloxycarbonylvalienamine (20 g) is dissolved in 1N aqueous sodium hydroxide (200 ml), and the solution is stirred at room temperature for 2 hours. The reaction mixture is adjusted to pH 5.5 with 2N hydrochloric acid, washed with ethyl ether and concentrated under reduced pressure. The residue is chromatographed on a column of activated carbon (400 ml), and the column is washed with water, followed by elution with 50% aqueous methanol. The eluate is concentrated under reduced pressure and lyophilized to produce valienamine 1,2-carbamate (12 g).

(b) Valienamine 1,2-carbamate (10 g) is dissolved in dimethylformamide (150 ml), and 2,2-dimethoxypropane (20 ml) and p-toluenesulfonic acid (250 mg) are added to the solution, followed by stirring at 100° C. for 2 hours. The reaction mixture is cooled to room temperature, and Dowex 1×2 (OH$^-$ type, produced by Dow Chemical Co., U.S.A.) (approximately 50 ml) is added, followed by stirring for 30 minutes. The Dowex 1×2 is filtered out and washed with ethanol. The filtrate and washings are combined and concentrated under reduced pressure. Toluene is added to the residue, and concentrated under reduced pressure (This procedure is repeated). The residue is dissolved in water (about 50 ml) and the solution is chromatographed on a column of MCI Gel CHP-20P (produced by Mitsubishi Chemical Industries, Ltd., Japan, 400 ml). The column is washed with water, and elution is effected with a gradient of water-methanol. The eluate is concentrated under reduced pressure and lyophilized to produce 4,7-O-isopropylidenevalienamine 1,2-carbamate (11.3 g).

(c) 4,7-O-Isopropylidenevalienamine 1,2-carbamate (4.8 g) is dissolved in dimethylformamide (50 ml). The solution is cooled to −40° C. or below, and benzyloxycarbonyl chloride (5.1 ml) and then triethylamine (3.1 ml) are added, followed by stirring at −20° to −10° C. for 2 hours. The reaction mixture is added to a mixture of 2N hydrochloric acid (500 ml) and ethyl acetate (500 ml) under ice-cooling, and the ethyl acetate layer is separated, washed with water, dried over sodium sulfate and concentrated under reduced pressure. The residue is chromatographed on a column of silica gel (250 ml), and elution is performed with toluene-ethyl acetate (1:1). The eluate is concentrated under reduced pressure, and ethyl ether-petroleum ether (1:10) (approximately 300 ml) is added to the residue, which is then allowed to stand overnight in a refrigerator to produce crystalline 3-O-benzyloxycarbonyl-4,7-O-isopropylidenevalienamine 1,2-carbamate (4.3 g).

$[\alpha]_D^{24} +126.8°$ (c=1, $CH_3OH$).

Elemental analysis, for $C_{19}H_{21}NO_7$: Calcd.(%): C, 60.79; H, 5.64; N, 3.37. Found (%): C, 60.68; H, 5.48; N, 3.51.

REFERENCE EXAMPLE 21

(1R)-(1($CH_2OH$),2,4,5/1(OH),3)-5-Amino-1-hydroxymethyl-1,2,3,4-cyclohexanetetrol (the 5-epimer of valiolamine)

A solution of bromine (1.8 g) in acetonitrile (20 ml) is added dropwise to a solution of 3-O-benzyloxycarbonyl-4,7-O-isopropylidenevalienamine 1,2-carbamate (3.7 g) in acetonitrile (60 ml) while stirring under cooling with ice-cold water, followed by stirring for 5.5 hours. The resulting precipitates are recovered by filtration and washed with a small volume each of acetonitrile and ethyl ether. The powder (1.2 g) thus obtained is dissolved in 50% aqueous ethanol (20 ml), to which is added sodium borohydride (500 mg) under cooling with ice-cold water, followed by stirring at room temperature for 4 hours. The reaction mixture is concentrated under reduced pressure and the residue is chromatographed on a column of activated carbon (180 ml), and the column is washed with water, followed by elution with 50% aqueous methanol. The eluate is concentrated under reduced pressure, and barium hydroxide (2.0 g) is added to the resulting aqueous solution (approximately 20 ml), followed by reflux for 2 hours. After the reaction mixture is cooled to room temperature, carbon dioxide gas is introduced into it, and the resulting precipitates are filtered off. The filtrate is chromatographed on a column of Amberlite CG-50 ($NH_4^+$ type, produced by Rohm & Haas Co., U.S.A.) (250 ml), and the column is washed with water, followed by elution with 0.2N aqueous ammonia. The eluate is concentrated under reduced pressure and lyophilized to produce white powdery, the 5-epimer of valiolamine (120 mg).

REFERENCE EXAMPLE 22

6,7,8-Triacetoxy-1-azidomethyl-3-oxo-2-oxa-4-azabicyclo[3.3.1]nonane (a) 6,7,8-Triacetoxy-1-bromomethyl-3-oxo-2-oxa-4-azabicyclo[3.3.1]nonane (as described in Example 1 of the Japanese Patent Application No. 144309/1981, pp. 37) (4.1 g) is dissolved in dimethylformamide (15 ml), and sodium azide (1.0 g) is added to the solution, followed by stirring under heating on a bath of the temperature of 130° to 140° C. for 7 hours. The reaction mixture is concentrated under reduced pressure and further freed of the dimethylformamide azeotropically with toluene, under reduced pressure. 20% Aqueous methanol (100 ml) is added to the residue, which is then allowed to stand overnight in a refrigerator. The resultant crystals are recovered by filtration, washed with 20% aqueous methanol cooled with ice, and dried to produce 6,7,8-triacetoxy-1-azidomethyl-3-oxo-2-oxa-4-azabicyclo[3.3.1]nonane (2.7 g).

$[\alpha]_D^{23} +79.1°$ (c=1, DMF).

$IR\nu_{max}^{KBr}$ $cm^{-1}$: 2130.

Elemental analysis, for $C_{14}H_{18}N_4O_8$: Calcd.(%): C, 45.40; H, 4.90; N, 15.13. Found (%): C, 45.58; H, 4.88; N, 15.31.

(b) 6,7,8-Triacetoxy-1-iodomethyl-3-oxo-2-oxa-4-azabicyclo[3.3.1]nonane (as described in Example 2 of the Japanese Patent Application No. 144309/1981, pp. 39) (4.5 g) is dissolved in dimethylformamide (15 ml), and sodium azide (1.0 g) is added to the solution, followed by stirring under heating on a bath of the temperature of 130° to 140° C. for 2 hours. The reaction mixture is treated in the same manner as described under (a) of Reference Example mentioned above to produce crystalline 6,7,8-triacetoxy-1-azidomethyl-3-oxo-2-oxa-4-azabicyclo[3.3.1]nonane (3.2 g).

REFERENCE EXAMPLE 23

7-Azido-7-deoxyvaliolamine 6,7,8-Triacetoxy-1-azidomethyl-3-oxo-2-oxa-4-azabicyclo[3.3.1]nonane (1.0 g) is suspended in water (100 ml), and barium hydroxide (4.0 g) is added to the suspension, followed by stirring at 70° C. for 5 hours. After the reaction mixture is cooled to room temperature, carbon dioxide gas is introduced into it, and the resulting precipitates are filtered out and washed with water. The filtrate and washings are combined, and chromatographed on a column of Amberlite CG-50 ($NH_4^+$ type, produced by Rohm & Haas Co. U.S.A.) (250 ml), and the column is washed with water, followed by elution with 0.1N aqueous ammonia. The eluate is concentrated under reduced pressure, and the residue is chromatographed on a column of Dowex 1×2 ($OH^-$ type, produced by Dow Chemical Co., U.S.A.) (250 ml), followed by elution with water. The eluate is concentrated under reduced pressure and lyophilized to produce 7-azido-7-deoxyvaliolamine (370 mg).

$[\alpha]_D^{23} +43.1°$ (c=1, $H_2O$).

IR $\nu_{max}^{KBr}$ $cm^{-1}$: 2115.

Elemental analysis, for $C_7H_{14}N_4O_4$: Calcd.(%): C, 38.53; H, 6.47; N, 25.68. Found (%): C, 38.71; H, 6.37; N, 25.45.

NMR ($D_2O$)δ: 1.78 (1H, dd, J=3.8 Hz, 15 Hz), 2.15 (1H, dd, J=3 Hz, 15 Hz), 3.44 (1H, d, J=13.5 Hz), 3.4–3.6 (1H, m), 3.52 (1H, d, J=9.5 Hz), 3.65 (1H, d, J=13.5 Hz), 3.73 (1H, dd, J=4.5 Hz, 9.5 Hz), 3.99 (1H, t, J=9.5 Hz).

TLC: Rf=0.54.

REFERENCE EXAMPLE 24

7-Amino-7-deoxyvaliolamine

7-Azido-7-deoxyvaliolamine (250 mg) is dissolved in 2% aqueous acetic acid (50 ml), and palladium black (200 mg) is added to the solution, followed by stirring under a stream of hydrogen at room temperature for 3 hours. The catalyst is filtered off, and the reaction mixture is concentrated under reduced pressure to dryness. The residue in an aqueous solution is chromatographed on a column of Amberlite CG-50 (NH$_4$+ type, produced by Rohm & Haas Co., U.S.A.) (180 ml), and the column is washed with water and 0.2N aqueous ammonia successively, followed by elution with 0.5N aqueous ammonia. The eluate is concentrated under reduced pressure and then lyophilized to produce 7-amino-7-deoxyvaliolamine (180 g).

$[\alpha]_D^{23} + 20.1°$ (c=1, H$_2$O).

Elemental analysis, for C$_7$H$_{16}$N$_2$O$_4$.H$_2$O: Calcd.(%): C, 39.99; H, 8.63; N, 13.33. Found (%): C, 39.85; H, 8.25; N, 12.76.

NMR (D$_2$O)δ: 1.73 (1H, dd, J=3.5 Hz, 15 Hz), 2.07 (1H, dd, J=3 Hz, 15 Hz), 2.77 (1H, d, J=13.5 Hz), 2.96 (1H, d, J=13.5 Hz), 3.4–3.85 (3H, m), 3.99 (1H, t, J=9.5 Hz).

TLC: Rf=0.14.

REFERENCE EXAMPLE 25

6,7,8-Triacetoxy-1-methyl-3-oxo-2-oxa-4-azabicyclo[3.3.1]nonane 6,7,8-Triacetoxy-1-bromomethyl-3-oxo-2-oxa-4-azabicyclo[3.3.1]nonane (as described in Example 1 of the Japanese Patent Application No. 144309/1981, pp. 37) (800 mg) is dissolved in toluene (50 ml), and tri-n-butyltin hydride (1 ml) and α,α'-azo-bis-isobutyronitrile (100 mg) are added to the solution, followed by reflux with stirring for 1 hour. The reaction mixture is concentrated under reduced pressure, and petroleum ether is added to the residue, which is allowed to stand overnight in a refrigerator. The resulting precipitates are recovered by filtration, dried and chromatographed on a column of silica gel (180 ml), followed by elution with ethyl acetate. The eluate is concentrated under reduced pressure, and ethyl ether-petroleum ether (1:1) is added to the residue, which is allowed to stand overnight in a refrigerator to produce crystalline 6,7,8-triacetoxy-1-methyl-3-oxo-2-oxa-4-azabicyclo[3.3.1]nonane (510 mg).

$[\alpha]_D^{24} + 61.3°$ (c=1, H$_2$O).

Elemental analysis, for C$_{14}$H$_{19}$NO$_8$: Calcd.(%): C, 51.06; H, 5.82; N, 4.25. Found (%): C, 51.03; H, 5.76; N, 4.19.

NMR (DMSO-d$_6$)δ: 1.17 (3H, s), 1.93 (3H, s), 1.98(3H, s), 2.03 (3H, s), 3.4–3.6 (1H, m), 4.8–5.2 (3H, m), 7.77 (1H, d, J=5.5 Hz).

REFERENCE EXAMPLE 26

7-Deoxyvaliolamine 6,7,8-Triacetoxy-1-methyl-3-oxo-2-oxa-4-azabicyclo[3.3.1]nonane (350 mg) is suspended in water (50 ml), and barium hydroxide (2.0 g) is added to the suspension, followed by stirring at 90° to 100° C. for 3 hours. After the reaction mixture is cooled to room temperature, carbon dioxide gas is introduced into it, and the resulting precipitates are filtered out and washed with water. The filtrate and washings are combined and chromatographed on a column of Amberlite CG-50 (NH$_4$+ type, produced by Rohm & Haas Co., U.S.A.) (150 ml), and the column is washed with water, followed by elution with 0.2N aqueous ammonia. The eluate is concentrated under reduced pressure, and the residue is chromatographed on a column of Dowex 1×2 (OH$^-$ type, produced by Dow Chemical Co., U.S.A.) (250 ml), followed by elution with water. The eluate is concentrated under reduced pressure and lyophilized to produce 7-deoxyvaliolamine (140 mg).

$[\alpha]_D^{23} + 12.3°$ (c=1, H$_2$O).

Elemental analysis, for C$_7$H$_{15}$NO$_4$.H$_2$O: Calcd.(%): C, 43.07; H, 8.78; N, 7.18. Found (%): C, 43.31; H, 8.59; N, 7.11.

NMR (D$_2$O)δ: 1.43 (3H, s), 1.90 (1H, dd, J=3.8 Hz, 15.5 Hz), 2.17 (1H, dd, J=2.6 Hz, 15.5 Hz), 3.45 (1H, d, J=9 Hz), 3.45–3.7 (1H, m), 3.85 (1H, dd, J=4 Hz, 9.2 Hz), 4.00 (1H, t, J=9 Hz). IC$_{50}$ (saccharase): 2.4×10$^{-5}$M.

TLC: Rf=0.34.

REFERENCE EXAMPLE 27

6,7,8-Trihydroxy-1-hydroxymethyl-3-oxo-2-oxa-4-azatricyclo[3.3.1.0$^{4,9}$]nonane 9-Bromo-6,7,8-trihydroxy-1-hydroxymethyl-3-oxo-2-oxa-4-azabicyclo[3.3.1]nonane (5.0 g) as obtained in Reference Example 3 is dissolved in methanol (100 ml), and sodium hydrogen carbonate (2.5 g) is added to the solution, followed by reflux with stirring for 2 hours. After the insoluble matter is filtered out and washed with methanol, the filtrate and washings are combined and concentrated under reduced pressure. The residue is chromatographed on a column of MCI Gel CHP 20P (500 ml), and elution is performed with water. The eluate (400 to 600 ml) is concentrated under reduced pressure and lyophilized to produce 6,7,8-trihydroxy-1-hydroxymethyl-3-oxo-4-azatricyclo[3.3.1.0$^{4,9}$]nonane (2.8 g).

$[\alpha]_D^{26} + 74.7°$ (c=1, H$_2$O).

IR $\nu_{max}^{KBr}$ cm$^{-1}$: 1780, 1740.

Elemental analysis, for C$_{18}$H$_{11}$NO$_6$: Calcd.(%): C, 44.24; H, 5.11; N, 6.45. Found (%): C, 44.20; H, 5.02; N, 6.43.

REFERENCE EXAMPLE 28

1-Hydroxymethyl-5,6-epiminocyclohexane-1,2,3,4-tetrol (1,6-epiminovaliolamine)

6,7,8-Trihydroxy-1-hydroxymethyl-3-oxo-2-oxa-4-azabicyclo[3.3.1.0$^{4,9}$]nonane (2.0 g) is dissolved in water (200 ml), and barium hydroxide (8.0 g) is added to the solution, followed by stirring at 60° to 70° C. for 5 hours. After the reaction mixture is cooled to room temperature, carbon dioxide gas is introduced into it, and the resulting precipitates (barium carbonate) are filtered out and washed with water. The filtrate and washings are combined and chromatographed on a column of Amberlite CG-50 (NH$_4$+ type, produced by Rohm & Haas Co., U.S.A.) (250 ml), and the column is washed with water, followed by elution with 0.1N aqueous ammonia. The eluate is concentrated under reduced pressure, and the residue is chromatographed on a column of Dowex 1×2 (OH$^-$ type, produced by Dow Chemical Co., U.S.A.) (500 ml), followed by elution with water. The eluate is concentrated under reduced pressure, and methanol is added to the residue, which is allowed to stand overnight in a refrigerator to produce crystalline 1-hydroxymethyl-5,6-epiminocyclohexane-1,2,3,4-tetrol (1,6-epiminovaliolamine) (385 mg).

$[\alpha]_D^{23} - 4.8°$ (c=1, H$_2$O).

Elemental analysis, for C$_7$H$_{13}$NO$_5$: Calcd.(%): C, 43.97; H, 6.85; N, 7.33. Found (%): C, 43.71; H, 6.90; N, 7.23.

TLC: Rf=0.44.

REFERENCE EXAMPLE 29

N-Benzyloxycarbonyl-7-O-tritylvalidamine

N-Benzyloxycarbonylvalidamine (as described in Reference Example 1 of the Japanese Patent Application No. 144309/1981, pp. 30) (3.1 g) is dissolved in pyridine (20 ml), and trityl chloride (3.5 g) is added to the solution, followed by stirring overnight at room temperature. The reaction mixture is concentrated under reduced pressure, and the residue is extracted with ethyl acetate. The extract is washed with 5% aqueous phosphoric acid and 5% aqueous sodium hydrogen carbonate successively, dried over sodium sulfate and concentrated under reduced pressure. The residue is chromatographed on a column of silica gel (400 ml), and elution is performed with chloroform-methanol (9:1). The eluate is concentrated under reduced pressure, and ethyl ether is added to the residue to give crystalline N-benzyloxycarbonyl-7-O-tritylvalidamine (3.3 g).

IR $\nu_{max}^{KBr}$ cm$^{-1}$: 3400, 1700.

REFERENCE EXAMPLE 30

N-Benzyloxycarbonyl-2,3,4-tri-O-acetyl-7-O-tritylvalidamine

N-Benzyloxycarbonyl-7-O-tritylvalidamine (3.0 g) is dissolved in pyridine (30 ml), and acetic anhydride (15 ml) is added to the solution, followed by stirring overnight at room temperature. After the reaction mixture is concentrated under reduced pressure, the residue is dissolved in ethyl acetate, and the solution is washed with 5% aqueous phosphoric acid and 5% aqueous sodium hydrogen carbonate successively, dried over magnesium sulfate and concentrated under reduced pressure. The residue is chromatographed on a column of silica gel (400 ml), and elution is performed with toluene-ethyl acetate (5:1). The eluate is concentrated under reduced pressure, and ethyl ether-petroleum ether (1:10) is added to the residue to produce N-benzyloxycarbonyl-2,3,4-tri-O-acetyl-7-O-tritylvalidamine (3.5 g).

Elemental analysis, for $C_{40}H_{41}NO_9$: Calcd.(%): C, 70.67; H, 6.08; N, 2.06. Found (%): C, 70.45; H, 6.05; N, 2.34.

IR $\nu_{max}^{KBr}$ cm$^{-1}$: 3340, 1750, 1730.

REFERENCE EXAMPLE 31

N-Benzyloxycarbonyl-2,3,4-tri-O-acetylvaldamine

N-Benzyloxycarbonyl-2,3,4-tri-O-acetyl-7-O-tritylvalidamine (3.0 g) is dissolved in 80% aqueous acetic acid (60 ml) under warming (60° to 80° C.), and the solution is stirred at 80° C. for 1 hour. The reaction mixture is concentrated under reduced pressure to dryness, and the residue is extracted with ethyl acetate. The ethyl acetate extract is washed with 5% aqueous phosphoric acid, 5% aqueous sodium hydrogen carbonate and water successively, dried over sodium sulfate and concentrated to dryness under reduced pressure. Petroleum ether is added to the residue, and the resulting precipitates are recovered by filtration and dried. The resulting powder (2.3 g) is dissolved in chloroform, and chromatographed on a column of silica gel (300 ml), followed by elution with chloroform-methanol (9:1). The eluate is concentrated to dryness under reduced pressure to produce N-benzyloxycarbonyl-2,3,4-tri-O-acetylvalidamine (1.8 g).

IR $\nu_{max}^{KBr}$ cm$^{-1}$: 3440, 3360, 1735.

REFERENCE EXAMPLE 32

N-Benzyloxycarbonyl-2,3,4-tri-O-acetyl-7-deoxy-7-phthalimidovalidamine

N-Benzyloxycarbonyl-2,3,4,-tri-O-acetylvalidamine (2.2 g), phthalimide (1.1 g) and triphenylphosphine (1.6 g) are dissolved in tetrahydrofuran (50 ml), and diethyl azodicarboxylate (1.1 g) is added to the solution under ice-cooling, followed by stirring at the same temperature for 2 hours. The reaction mixture is concentrated under reduced pressure, and the residue is extracted with ethyl acetate. The extract is washed with 5% aqueous sodium hydrogen carbonate and 5% aqueous phosphoric acid successively, dried over sodium sulfate and concentrated to dryness under reduced pressure. The residue is dissolved in toluene and chromatographed on a column of silica gel (400 ml), followed by elution with toluene-acetone (9:1). The eluate is concentrated under reduced pressure, and ethyl ether is added to the residue to produce crystalline N-benzyloxycarbonyl-2,3,4-tri-O-acetyl-7-deoxy-7-phthalimidovalidamine (0.7 g).

IR $\nu_{max}^{KBr}$ cm$^{-1}$: 3380, 1785, 1735, 1710.

REFERENCE EXAMPLE 33

2,3,4-Tri-O-acetyl-7-deoxy-7-phthalimidovalidamine

N-Benzyloxycarbonyl-2,3,4-O-triacetoxy-7-deoxy-7-phthalimidovalidamine (640 mg) is added to a mixture of 70% aqueous ethanol (50 ml), acetic acid (10 ml) and ethyl acetate (10 ml), and palladium black (215 mg) is added to the mixture, followed by stirring under a stream of hydrogen at room temperature for 4 hours. After the catalyst is filtered out and washed with ethanol, the filtrate and washings are combined and concentrated under reduced pressure. Ethyl ether is added to the residue to produce 2,3,4-tri-O-acetyl-7-deoxy-7-phthalimidovalidamine (335 mg).

IR $\nu_{max}^{KBr}$cm$^{-1}$: 1770, 1740, 1715, 1240

REFERENCE EXAMPLE 34

7-Amino-7-deoxyvalidamine 2,3,4-Tri-O-acetyl-7-deoxy-7-phthalimidovalidamine (250 mg) is dissolved in 2% hydrazine hydrate methanol solution (25 ml), and the solution is stirred overnight at room temperature. The reaction mixture is concentrated under reduced pressure, and the residue is chromatographed on a column of Amberlite CG-50 (NH$_4^+$ type, produced by Rohm & Haas Co., U.S.A.) (200 ml), followed by washing with water (800 ml) and elution with 0.4% aqueous ammonia. The eluate is concentrated under reduced pressure and lyophilized to produce 7-amino-7-deoxyvalidamine (64 mg).

$[\alpha]_D^{23}$ +43.3° (c=1, H$_2$O).

Elemental analysis, for $C_7H_{16}N_2O_3.2H_2O$: Calcd.(%): C, 39.61; H, 9.50; N, 13.20. Found (%): C, 39.33; H, 9.75; N, 13.14.

TLC: Rf=0.14

REFERENCE EXAMPLE 35

N-Ethoxycarbonyl-7-O-tritylvalienamine

N-Ethoxycarbonylvalienamine (5.0 g) is dissolved in pyridine (35 ml), and trityl chloride (11.3 g) is added to the solution under ice-cooling, followed by stirring overnight at room temperature. After the reaction mixture is concentrated under reduced pressure, the residue is dissolved in chloroform (300 ml), and the chloroform solution is washed with 2N hydrochloric acid, 5% aqueous sodium hydrogen carbonate and water successively, dried over magnesium sulfate and freed of the solvent under reduced pressure. The residue is dissolved in ethyl ether, and petroleum ether is added to the solution to give crystalline N-ethoxycarbonyl-7-O-tritylvalienamine (4.8 g). The mother liquor is concentrated to dryness under reduced pressure, and the residue is dissolved in chloroform and chromatographed on a column of silica gel (180 ml), followed by elution with a mixture of chloroform-methanol (19:1). The eluate is concentrated to dryness, and the residue is crystallized from ethyl ether-petroleum ether to produce further crystalline N-ethoxycarbonyl-7-O-tritylvalienamine (3.0 g).

IR $\nu_{max}^{KBr}$cm$^{-1}$: 3400, 1705.

REFERENCE EXAMPLE 36

N-Ethoxycarbonyl-2,3,4-tri-O-acetyl-7-O-tritylvalienamine

N-Ethoxycarbonyl-7-O-tritylvalienamine (7.5 g) is dissolved in pyridine (75 ml), and acetic anhydride (37.5 ml) is added to the solution under ice-cooling, followed by stirring overnight at room temperature. The reaction mixture is concentrated to dryness under reduced pressure, and the residue is distributed between ethyl acetate and water. The ethyl acetate layer is separated, washed with 5% aqueous phosphoric acid, 5% aqueous sodium hydrogen carbonate and water successively, dried over sodium sulfate and concentrated to dryness under reduced pressure. The residue is dissolved in ethyl ether, and petroleum ether is added to the solution to produce crystalline N-ethoxycarbonyl-2,3,4-tri-O-acetyl-7-O-tritylvalienamine (9.0 g).

IR $\nu_{max}^{KBr}$cm$^{-1}$: 3330, 1750, 1740, 1700.

REFERENCE EXAMPLE 37

N-Ethoxycarbonyl-2,3,4-tri-O-acetylvalienamine

N-Ethoxycarbonyl-2,3,4-tri-O-acetyl-7-O-tritylvalienamine (8.5 g) is dissolved in ethyl acetate (80 ml), and 80% aqueous acetic acid (160 ml) is added to the solution, followed by stirring at 60° C. for 8 hours. the reaction mixture is concentrated under reduced pressure. The residue is extracted with ethyl acetate, and the ethyl acetate extract is washed with 5% aqueous phosphoric acid, 5% aqueous sodium hydrogen carbonate and water successively, dried over sodium sulfate and concentrated to dryness under reduced pressure. The residue is dissolved in toluene, and chromatographed on a column of silica gel (250 ml), followed by elution with toluene-acetone (3:1). The eluate is concentrated to dryness under reduced pressure, and the residue is dissolved in ethyl ether. Petroleum ether is added to the solution to produce crystalline N-ethoxycarbonyl-2,3,4-tri-O-acetylvalienamine (2.8 g).

IR $\nu_{max}^{KBr}$cm$^{-1}$: 3480, 3300, 1740, 1710.

REFERENCE EXAMPLE 38

N-Ethoxycarbonyl-2,3,4-tri-O-acetyl-7-deoxy-7-phthalimidovalienamine

N-Ethoxycarbonyl-2,3,4-tri-O-acetylvalienamine (2.5 g), phthalimide (1.95 g) and triphenylphosphine (2.65 g) are dissolved in tetrahydrofuran (45 ml), and diethyl azodicarboxylate (1.65 ml) is added to the solution under ice-cooling, foloowed by stirring at the same temperature for 1 hour and further at room temperature for 30 minutes. The reaction mixture is concentrated under reduced pressure, and the residue is distributed between ethyl acetate and water. The ethyl acetate layer is separated, washed with 5% aqueous phosphoric acid, 5% aqueous sodium hydrogen carbonate and water successively, dried over sodium sulfate and freed of the solvent under reduced pressure. The residue is dissolved in toluene and chromatographed on a column of silica gel (270 ml), followed by elution with toluene-acetone (6:1). The eluate is concentrated under reduced pressure, and ethyl ether (130 ml) is added to the residue, which is allowed to stand at a cool place to produce crystalline N-ethoxycarbonyl-2,3,4-tri-O-acetyl-7-deoxy-7-phthalimidovalienamine (2.2 g).

IR $\nu_{max}^{KBr}$cm$^{-1}$: 3350, 1780 (sh), 1730, 1725.

REFERENCE EXAMPLE 39

7-Amino-7-deoxyvalienamine

N-Ethoxycarbonyl-2,3,4-tri-O-acetyl-7-deoxy-7-phthalimidovalienamine (2.0 g) is dissolved in 2% hydrazine hydrate methanol solution (400 ml), and the solution is stirred overnight at room temperature. Water (400 ml) is added to the solution under ice-cooling, and the reaction mixture is adjusted to pH 6 with acetic acid. The methanol is distilled off under reduced pressure, and the insoluble matter is filtered off. The filtrate is chromatographed on a column of Amberlite CG-50 (NH$_4^+$ type, produced by Rohm & Haas Co., U.S.A.) (800 ml), and the column is washed with water (1.6 l), followed by elution with 0.4% aqueous ammonia. The eluate is concentrated under reduced pressure, and lyophilized to give 7-amino-7-deoxyvalienamine (0.3 g).

$[\alpha]_D^{23}$ +70.1° (c=1, H$_2$O).

Elemental analysis, for C$_7$H$_{14}$N$_2$O$_3$.2H$_2$O: Calcd.(%): C, 39.99; H, 8.63; N, 13.33. Found (%): C, 39.68; H, 8.79; N, 13.14.

TLC: Rf=0.22.

REFERENCE EXAMPLE 40

Methyl 4-[(1S,6S)-(4,6/5)-4,5,6-trihydroxy-3-hydroxymethyl-2-cyclohexen-1-yl]amino-4,6-dideoxy-α-D-glucopyranoside and its 6-deoxygalactopyranoside isomer Valienamine (2.0 g) and methyl 2,3-O-cycloexylidene-6-deoxy-α-D-xylo-4-hexopyranoside-4-urose(-methyl 2,3-O-cyclohexylidene-6-deoxy-α-D-xylo-4-hexopyranose uroside) (5.5 g) are dissolved in dimethylformamide (50 ml), and 2N hydrochloric acid (1.5 ml) and sodium cyanoborohydride (2.6 g) are added to the solution, followed by stirring at 60° to 70° C. for 18 hours. The reaction mixture is concentrated under reduced pressure, and the residue is dissolved in water (150 ml). Dowex 50W×8 (H$^+$ type, produced by Dow Chemical Co., U.S.A.) (150 ml) is added to the solution, and the mixture is stirred at room temperature for 2 hours. The mixture is poured onto a column packed with Dowex 50W×8 (H$^+$ type, 30 ml), and the column is washed with water (1 l), followed by elution with 0.5N aqueous ammonia. The eluate (0.7 to 1.6 l) is concentrated under reduced pressure, and the concentrate is chromatographed on a column of Amberlite CG-50 (NH$_4^+$ type, produced by Rohm & Haas Co., U.S.A.) (250 ml), followed by elution with water. The eluate (150 to 270 ml) is concentrated under reduced pressure, and the residue is chromatographed on a column of Dowex 1×2 (OH$^-$ type, produced by Dow Chemical Co., U.S.A.) (1 l), followed by elution with water to give two fractional components. The first fraction (1.10 to 1.71 l) is concentrated under reduced pressure and lyophilized to produce the 6-deoxygalactopyranoside isomer (370 mg). The later fraction (2.24 to 4.56 l) is concentrated under reduced pressure to leave syrupy substance, to which is added ethanol (150 ml), which is then allowed to stand overnight in a refrigerator to produce crystals (1.0 g) of the 6-deoxyglucopyranoside isomer. The mother liquor is concentrated to dryness under reduced pressure to recover the isomer (230 mg).

The first eluted isomer (6-deoxygalactopyranoside isomer): $[\alpha]_D^{22} + 133.6°$ (c=1, H$_2$O).

Elemental analysis, for $C_{14}H_{25}NO_8 \cdot \frac{1}{2}H_2O$: Calcd.(%): C, 48.83; H, 7.61; N, 4.07. Found (%): C, 48.58; H, 7.66; N, 3.86.

NMR (D$_2$O)δ: 1.64 (3H, d, J=6.5 Hz), 3.37 (1H, dd, J=1.5 Hz, 4 Hz), 3.6–4.7 (9H, m), ~5.1 (1H), 6.32 (1H, J=1.5 Hz, 5 Hz).

IC$_{50}$ (saccharase): $6.6 \times 10^{-5}$ M.
TLC: Rf=0.45.

The later eluted isomer (6-deoxyglucopyranoside isomer): $[\alpha]_D^{22} + 131.5°$ (C=1, H$_2$O).

Elemental analysis, for $C_{14}H_{25}NO_8 \cdot \frac{1}{2}H_2O$: Calcd.(%): C, 48.83; H, 7.61; N, 4.07. Found (%): C, 48.59; H, 7.56; N, 3.69.

NMR(D$_2$O)δ: 1.68 (3H, d, J=6.5 Hz), 2.88 (1H, m), 3.7–4.75 (9H, m), 3.74 (3H, s), ~5.05 (1H), 6.25 (1H, dd, J=1.5 Hz, 5Hz).

IC$_{50}$ (maltase): $3.2 \times 10^{-6}$M.
IC$_{50}$ (saccharase): $7.0 \times 10^{-7}$M.
TLC: Rf=0.54.

REFERENCE EXAMPLE 41

N-(2,3,5-Trihydroxy-6-hydroxymethyltetrahydropyran-4-yl)valienamine and
N-[2,3-O-isopropylidene-2,3-dihydroxy-5-(1,2-dihydroxyethyl)tetrahydrofuran-4-yl]valienamine Valienamine (1.0 g) and 1,2:5,6-di-O-isopropylidene-α-D-ribo-hexofuranose-3-urose (2.0 g) are dissolved in dimethylformamide (25 ml), and 2N hydrochloric acid (0.75 ml) and sodium cyanoborohydride (1.3 g) are added to the solution, followed by stirring at room temperature for 40 hours. The reaction mixture is concentrated under reduced pressure, and freed of the dimethylformamide azeotropically with toluene. The residue is dissolved in water (100 ml), and Dowex 50W×8 (H$^+$ type, produced by Dow Chemical Co., U.S.A.) (120 ml) is added to the solution, followed by stirring at room temperature for 1 hour. The mixture is poured onto a column of Dowex 50W×8 (H$^+$ type, 30 ml), and the column is washed with water, followed by elution with 0.5N aqueous ammonia. The eluate is concentrated under reduced pressure and chromatographed on a column of Amberlite CG-50 (NH$_4^+$ type, produced by Rohm & Haas Co., U.S.A.) (250 ml), and elution is performed with water to give two fractional components. The first fraction (210 to 285 ml) is concentrated under reduced pressure and chromatographed on a column of Dowex 1×2 (OH$^-$ type, produced by Dow Chemical Co., U.S.A.) (250 ml), followed by elution with water. The eluate is concentrated under reduced pressure and lyophilized to give white powdery N-[2,3-O-isopropylidene-2,3-dihydroxy-5-(1,2-dihydroxyethyl)-tetrahydrofuran-4-yl]valienamine (500 mg).

The later fraction (290 to 360 ml) is concentrated under reduced pressure and again chromatographed on a column of Amberlite CG-50 (NH$_4^+$ type, 250 ml), followed by elution with water. The eluate is concentrated under reduced pressure and lyophilized to give white powdery N-[2,3,5-trihydroxy-6-hydroxymethyl-tetrahydropyran-4-yl]valienamine (400 mg). The above-mentioned isopropylidene derivative (500 mg) as obtained from the first eluted fraction is dissolved in water (50 ml), and Dowex 50W×8 (H$^+$ type, 30 ml) is added to the solution, followed by stirring at 80° to 90° C. for 1 hour. The mixture is poured onto a column of Dowex 50W×8 (H$^+$ type, 5 ml), and the column is washed with water, followed by elution with 0.5N aqueous ammonia. The e eluate is concentrated under reduced pressure and chromatographed on a column of Amberlite CG-50 (NH$_4^+$ type, 250 ml), and elution is performed with water. The eluate is concentrated under reduced pressure and lyophilized to give white powdery N-(2,3-truhydroxy-6-hydroxymethyl-tetrahydropyran-4-yl)valienamine (350 mg).

N-[2,3-O-isopropylidene-2,3-dihydroxy-5-(1,2-dihydroxyethyl)tetrahydrofuran-4-yl]valienamine:
$[\alpha]_D^{23} + 172.4°$ (c=1, H$_2$O).

Elemental analysis, for $C_{16}H_{27}NO_9 \cdot H_2O$: Calcd. (%): C, 48.48; H, 7.63; N, 3.53. Found (%): C, 48.42; H, 7.47; N, 3.47.

NMR (D$_2$O)δ: 1.55 (3H, s), 1.72 (3H, s), 3.55 (1H, q, J=5 Hz), 3.65–4.5 (10H, m), 5.12 (1H, t, J=4.5 Hz), 6.09 (2H, t, J=4.5 Hz), 6.09 (2H, d, J=4.5 Hz).

TLC: Rf=0.58.

N-(2,3,5-trihydroxy-6-hydroxymethyltetrahydropyran-4-yl)valienamine: $[\alpha]_D^{23} + 129.9°$ (c=1, H$_2$O).

Elemental analysis, for $C_{13}H_{23}NO_9 \cdot H_2O$: Calcd.(%): C. 43.94; H, 7.09; N, 3.94. Found (%): C, 44.00; H, 7.31; N, 3.97.

IC$_{50}$ (maltase): $3.1 \times 10^{-5}$M.
IC$_{50}$ (saccharase): $4.5 \times 10^{-7}$M.
TLC: Rf=0.42.

REFERENCE EXAMPLE 42

Methyl 4-[(1S,6S)-(4,6/5)-4,5,6-trihydroxy-3-hydroxymethyl-2-cyclohexen-1-yl)amino-4-deoxy-α-D-glucopyranoside and its galactopyranoside isomer Valienamine (1.5 g) and methyl 6-O-acetyl-2,3-O-cyclohexylidene-α-D-xylo-hexopyranoside-4-urose (3.8 g) are dissolved in dimethylformamide (35 ml), and 2N hydrochloric acid (1.0 ml) and sodium cyanoborohydride (2.0 g) are added to the solution, followed by stirring at 60° to 70° C. for 15 hours. The reaction mixture is concentrated under reduced pressure, and the residue is dissolved in 50% aqueous methanol (100 ml). Dowex 50W×8 (H$^+$ type, produced by Dow Chemical Co., U.S.A.) (100 ml) is added to the solution, which is stirred at room temperature for 1.5 hours. The mixture is poured onto a column packed with Dowex 50W×8 (H$^+$ type, 50 ml), and the column is washed with water (1 l), followed by elution with 0.5N aqueous ammonia. The eluate (0.61 to 1.25 l) is concentrated under reduced pressure, and the residue is dissolved in 4% aqueous ammonia (200 ml), followed by stirring overnight at room temperature. The reaction mixture is concentrated to dryness under reduced pressure, and the residue is dissolved in water (approximately 10 ml), and chromatographed on a column of Amberlite CG-50 (NH$_4^+$ type, produced by Rohm & Haas Co., U.S.A.) (450 ml), and elution is performed with water. The eluate (210 to 325 ml) is concentrated under reduced pressure, and the residue is chromatographed on a column of Dowex 1×2 (OH⁻ type, produced by Dow Chemical Co., U.S.A.) (850 ml), followed by elution with water to give two fractional components. The first fraction (1.18 to 1.67 l) is concentrated under reduced pressure, and lyophilized to give the galactopyranoside isomer (203 mg), while the later fraction (2.1 to 3.0 l) is concentrated under reduced pressure and lyophilized to produce the glucopyranoside isomer (430 mg).

The first eluted isomer (galactopyranoside isomer): $[\alpha]_D^{22}$: 192.4° (c=1, H$_2$O).

Elemental analysis, for C$_{14}$H$_{25}$NO$_9$: Calcd.(%): C, 47.86; H, 7.17; N, 3.99. Found (%): C, 47.57; H, 7.15; N, 3.53.

NMR (D$_2$O(δ: 3.42 (1H, broad d, J=4 Hz), 3.62 (3H, s), 3.6–4.5 (11H, m), 5.04 (1H, d, J=3.6 Hz), 6.23 (1H).

IC$_{50}$ (maltase): 8.0×10⁻⁵M.
IC$_{50}$ (saccharase): 4.0×10⁻⁶M.
TLC: Rf=0.40.

The later eluted isomer (glucopyranoside isomer): $[\alpha]_D^{22}$+174.7° (c=1, H$_2$O).

Elemental analysis, for C$_{14}$H$_{25}$NO$_9$.½H$_2$O: Calcd.(%): C, 46.66; H, 7.27; N, 3.89. Found (%): C, 46.26; H, 7.23; N, 3.34.

NMR (D$_2$O)δ: 2.77–3.03 (1H, m), 3.62 (3H, s), 3.6–4.5 (11H, m), 5.02 (1H, d, J=3 Hz), 6.11 (1H).

IC$_{50}$ (maltase): 7.2×10⁻⁶M.
IC$_{50}$ (saccharase): 3.2×10⁻⁷M.
TLC: Rf=0.49.

REFERENCE EXAMPLE 43

N-(2,4-Diethoxycarbonylamino-5,6-dihydroxycyclohexyl)-7-azido-7-deoxyvaliolamine 7-Azido-7-deoxyvaliolamine (2.0 g) and a mixture of N,N'-diethoxycarbonyl-4,5-O-isopropylidene-6-oxo-2-deoxystreptamine and N,N'-diethoxycarbonyl-5,6-O-isopropylidene-4-oxo-2-deoxystreptamine (4.0 g) as obtained in Reference Example 18 are dissolved in dimethylformamide (50 ml), and 2N hydrochloric acid (1.5 ml) and sodium cyanoborohydride (2.6 g) are added to the solution, followed by stirring at 60° to 70° C. for 15 hours. The reaction mixture is concentrated under reduced pressure, and toluene is further added to the concentrate to repeat concentration under reduced pressure azeotropically. The residue is dissolved in water (200 ml), and Dowex 50W×8 (H⁺ type, produced by Dow Chemical Co., U.S.A.) (200 ml) is added to the solution, followed by stirring at 60° C. for 1 hour. The mixture is poured onto a column packed with Dowex 50W×8 (H⁺ type, 50 ml), and the column is washed with water, followed by elution with 0.5N aqueous ammonia. The eluate is concentrated under reduced pressure, and the residue is chromatographed on a column of Amberlite CG-50 (NH$_4$⁺ type, produced by Rohm & Haas Co., U.S.A.) (400 ml), followed by elution with water. The eluate is concentrated under reduced pressure and lyophilized to produce N-(2,4-diethoxycarbonylamino-5,6-dihydroxycyclohexyl)-7-azido-7-deoxy-valiolamine (1.6 g).

$[\alpha]_D^{23}$+27.7° (c=1, H$_2$O).
Elemental analysis, for C$_{19}$H$_{34}$N$_6$O$_{10}$.H$_2$O: Calcd.(%): C, 43.51; H, 6.92; N, 16.02. Found (%): C, 43.82; H, 6.61; N, 15.70.

REFERENCE EXAMPLE 44

1-N-(2,4-Diethoxycarbonylamino-5,6-dihydroxycyclohexyl)-7-amino-7-deoxyvaliolamine N-(2,4-Diethoxycarbonylamino-5,6-dihydroxycyclohexyl)-7-azido-7-deoxyvaliolamine (1.4 g) is dissolved in water (50 ml), and acetic acid (1 ml) and palladium black (250 mg) are added to the solution, followed by stirring under a stream of hydrogen at room temperature for 4 hours. The catalyst is filtered out, and washed with water, and the filtrate and washings are combined and concentrated to dryness under reduced pressure. The residue is dried overnight in a desiccator under reduced pressure, then dissolved in water (10 ml) and chromatographed on a column of Amberlite CG-50 (NH$_4$⁺ type, produced by Rohm & Haas Co., U.S.A.) (250 ml). The column is washed with water, and elution is effected with 0.2N aqueous ammonia. The eluate is concentrated under reduced pressure and lyophilized to give white powdery 1-N-(2,4-diethoxycarbonylamino-5,6-dihydroxycyclohexyl)-7-amino-7-deoxy-valiolamine (850 mg).

$[\alpha]_D^{23}$+13.2° (c=1, H$_2$O).

Elemental analysis, for C$_{19}$H$_{36}$N$_4$O$_{10}$.H$_2$O: Calcd.(%): C, 45.77; H, 7.68; N, 11.24. Found (%): C, 45.88; H, 7.85; N, 10.95.

REFERENCE EXAMPLE 45

1-N-(2,4-Diamino-5,6-dihydroxycyclohexyl)-7-amino-7-deoxyvaliolamine

1-N-(2,4-Diethoxycarbonylamino-5,6-dihydroxycyclohexyl)-7-amino-7-deoxyvaliolamine (700 mg) is dissolved in water (25 ml), and barium hydroxide (3.0 g) is added to the solution, followed by stirring at 70° to 80° C. for 10 hours. After the reaction mixture is cooled to room temperature, carbon dioxide gas is introduced into it, and the resulting precipitates are filtered out and washed with water. The filtrate and washings are combined, and chromatographed on a column of Amberlite CG-50 (NH$_4$⁺ type, produced by Rohm & Haas Co., U.S.A.) (100 ml). The column is washed with water, and elution is performed with 0.2N aqueous ammonia and then with 0.5N aqueous ammonia. The eluate is concentrated under reduced pressure and chromatographed on a column of Dowex 1×2 (OH⁻ type, produced by Dow Chemical Co., U.S.A.) (130 ml), and the column is washed with water, followed by elution with 0.5N hydrochloric acid. The eluate is adjusted to pH 6 and chromatographed on a column of Amberlite CG-50 (NH$_4$⁺ type, 100 ml), and the column is washed with water, followed by elution with 1N aqueous ammonia. The eluate is concentrated under reduced pressure and lyophilized to give white powderly 1-N-(2,4-diamino-5,6-dihydroxycyclohexyl)-7-amino-7-deoxyvaliolamine (150 mg).

$[\alpha]_D^{22}$+17.7° (c=1, H$_2$O).

Elemental analysis, for C$_{13}$H$_{28}$N$_4$O$_6$.2H$_2$O: Calcd. (%): C, 41.92; H, 8.66; N, 15.05. Found (%): C, 41.42; H, 8.52; N, 14.84.

REFERENCE EXAMPLE 46

Methyl 2,3-di-O-acetyl-4-[(1S,2S)-(2,4,5(OH)/3,5(CH$_2$OH))-2,3,4-triacetoxy-5-acetoxymethyl-5-hydroxycyclohexyl]amino-4,6-dideoxy-α-D-glucopyranoside Methyl 4-[(1S,2S)-(2,4,5(OH)/3,5(CH$_2$OH))-2,3,4,5-tetrahydroxy-5-hydroxymethylcyclohexyl]amino-4,6-dideoxy-α-D-glucopyranoside (200 mg) is dissolved in pyridine (5 ml), and acetic anhydride (3 ml) is added to the solution, followed by stirring overnight at room temperature. The reaction mixture is concentrated under reduced pressure, and the residue is dried overnight in a desiccator under reduced pressure and treated with ethyl ether-petroleum ether (1:1, approximately 30 ml). The mixture is allowed to stand overnight at room temperature to give crystalline, the hexa-O-acetyl derivative (265 mg).

$[\alpha]_D^{23} + 62.9°$ (c=1, CH$_3$OH).

Elemental analysis, for C$_{26}$H$_{39}$NO$_{15}$: Calcd.(%): C, 51.57; H, 6.49; N, 2.31. Found (%): C, 51.68; H, 6.36; N, 2.09.

NMR (CDCl$_3$)δ: 1.36(3H, d, J=6 Hz), 1.70(1H, dd, J=3.5 Hz, 15 Hz), 1.97(6H, s), 2.02(3H, s), 2.04(6H, s), 2.08(3H, s), 2.10(1H, dd, J=3 Hz, 15 Hz), 2.5–2.85(1H, m, when D$_2$O is added, δ changes to 2.66(t, J=10)), 3.37(3H, s), 3.5–3.85(2H, m), 3.72(1H, d, J=11.5 Hz), 4.03(1H, d, J=11.5 Hz), 4.03(1H, d, J=11.5 Hz), 4.7–4.9(2H), 5.03(1H, d, J=10 Hz), 5.04(1H, dd, J=4.5 Hz, 10.5 Hz), 5.32(1H, t, J=10.5 Hz), 5.58(1H, t, J=10 Hz).

REFERENCE EXAMPLE 47

Methyl 2,3,6-tri-O-acetyl-4-[(1S,2S)-(2,4,5(OH)/3,5(CH$_2$OH))-2,3,4-triacetoxy-5-acetoxymethyl-5-hydroxycyclohexyl]amino-4-deoxy-α-D-glucopyranoside Methyl 4-[(1S,2S)-(2,4,5(OH)/3,5(CH$_2$OH)-2,3,4,5-tetrahydroxy-5-hydroxymethylcyclohexyl]amino-4-deoxy-α-D-glucopyranoside (100 mg) is dissolved in pyridine (4 ml), and acetic anhydride (2 ml) is added to the solution, followed by standing overnight at room temperature. The reaction mixture is concentrated under reduced pressure, and the residue is dried overnight in a desiccator under reduced pressure, treated with ethyl ether-petroleum ether (1:2, ca. 20 ml), and allowed to stand overnight in a refrigerator to produce crystals (150 mg) of the hepta-O-acetyl derivative.

$[\alpha]_D^{23} + 66.0°$ (c=1, CH$_3$OH).

Elemental analysis, for C$_{28}$H$_{41}$NO$_{17}$: Calcd.(%): C, 50.68; H, 6.23; N, 2.11. Found (%): C, 50.64; H, 6.30; N, 2.21.

NMR (CDCl$_3$)δ: 1.73(1H, dd, J=4 Hz, 15.5 Hz), 1.9–2.3(1H), 1.97(3H, s), 2.01(3H, s), 2.04(9H, s), 2.10(3H, s), 2.13(3H, s), 2.75–3.2(1H, m, when D$_2$O is added, δ changes to 2.97(t, J=10 Hz)), 3.39(3H, s), 3.5–3.85(2H, m), 3.67(1H, d, J=11.7 Hz), 3.99(1H, d, J=11.7 Hz), 4.15–4.6(2H, m), 4.65–5.15(4H, m), 5.34(1H), 5.55(1H, t, J=10 Hz).

REFERENCE EXAMPLE 48

(2R)-(2,4/3,5)-2,3,4-Trihydroxy-5-hydroxymethylcyclohexanone

Validamine (1.8 g) and 3,5-di-tert-butyl-1,2-benzoquinone (2.3 g) are dissolved in methanol (100 ml), and the solution is stirred under a stream of nitrogen at room temperature for 24 hours. After water (10 ml) is added, the reaction mixture is adjusted to pH 1 with 3N sulfuric acid and stirred at room temperature for 3 hours. Water (500 ml) is added to the reaction mixture, which is washed five times with chloroform. The resultant water layer is adjusted to pH 5.5 by adding Dowex 1×8 (OH$^-$, type, produced by Dow Chemical Co., U.S.A.). The reaction mixture is filtered, and the filtrate is concentrated under reduced pressure and then lyophilized to produce white powdery (2R)-(2,4/3,5)-2,3,4-trihydroxy-5-hydroxymethylcyclohexanone (1.3 g).

Elemental analysis, for C$_7$H$_{12}$O$_5$·$\frac{3}{4}$H$_2$O: Calcd.(%): C, 44.33 H, 7.17. Found (%): C, 44.33; H, 7.23.

IR $\nu_{max}^{KBr}$ cm$^{-1}$: 1735 (C=O).

NMR (D$_2$O)δ: 4.51 (1H, d, J=10 Hz, 2-CH).

REFERENCE EXAMPLE 49

Octa-O-acetyl derivative of N-[(1R,2S)-(2,4/3,5)-2,3,4-trihydroxy-5-hydroxymethylcyclohexyl]validamine N-[(1R,2S)-(2,4/3,5)-2,3,4-Trihydroxy-5-hydroxymethylcyclohexyl]validamine (50 mg) is dissolved in pyridine (2 ml), and after acetic anhydride (1.0 ml) is added, the solution is allowed to stand overnight at room temperature. The reaction mixture is concentrated under reduced pressure, and the residue is dried overnight in a desiccator under reduced pressure, admixed with ethyl ether-petroleum ether (1:2, about 30 ml) and allowed to stand overnight in a refrigerator. The resulting precipitates are separated by filtration and dried to produce white powder (75 mg) of the subject octa-O-acetyl derivative.

$[\alpha]_D^{25} + 33.8°$ (c=0.5, CH$_3$OH).

Elemental analysis, for C$_{30}$H$_{43}$NO$_{16}$: Calcd. (%): C, 53.49; H, 6.43; N, 2.08. Found (%): C, 53.13; H, 6.50; N, 1.97.

NMR (CDCl$_3$)δ: 1.1–2.5(6H, m), 1.97–2.10(24H, CH$_3$COO-x8), 2.5–2.9(1H, m), 3.43(1H, m), 3.91(2H, dd, J=3.5 Hz, 11 Hz), 4.11(2H, dd, J=4.8 Hz, 11 Hz), 4.73–5.13(5H, m), 5.43(1H, t, J=10 Hz).

REFERENCE EXAMPLE 50

Octa-O-acetyl derivative of N-[(1S,2S)-(2,4/3,5)-2,3,4-trihydroxy-5-hydroxymethylcyclohexyl]validamine By treating N-[(1S,2S)-(2,4/3,5)-2,3,4-trihydroxy-5-hydroxymethylcyclohexyl]validamine (100 mg) in the same manner as in Reference Example 49, there is obtained the subject octa-O-acetyl derivative (115 mg).

$[\alpha]_D^{25} + 101.2°$ (c=0.5, CH$_3$OH).

Elemental analysis, for C$_{30}$H$_{43}$NO$_{16}$: Calcd.(%): C, 53.49; H, 6.43; N, 2.08. Found (%): C, 53.28; H, 6.57; N, 2.13.

NMR (CDCl$_3$)δ: 1.14–2.6(6H, m), 2.00–2.07(24H, CH$_3$COO-x8), 3.23(2H, m), 3.89(2H, dd, J=3.5 Hz, 11.5 Hz), 4.16(2H, dd, J=5.4 Hz, 11.5 Hz), 4.88(2H, dd, J=4.5 Hz, 10.5 Hz), 4.96(2H, dd, J=9 Hz, 10 Hz), 5.36(2H, dd, J=9 Hz, 10.5 Hz).

REFERENCE EXAMPLE 51

Octa-O-acetyl derivative of N-[(1R,2S)-(2,4/3,5)-2,3,4-trihydroxy-5-hydroxymethylcyclohexyl]valiolamine By treating N-[(1R,2S)-(2,4/3,5)-2,3,4-trihydroxy-5-hydroxymethylcyclohexyl]valiolamine (100 mg) in the same manner as in Reference Example 49, there is obtained the subject octa-O-acetyl derivative (124 mg).

$[\alpha]_D^{25} - 3.9°$ (c=1, CH$_3$OH).

Elemental analysis, for C$_{30}$H$_{43}$NO$_{17}$: Calcd.(%): C, 52.25; H, 6.28; N, 2.03. Found (%): C, 51.91; H, 6.36; N, 2.30.

NMR (CDCl$_3$)δ: 1.2–2.5(5H, m), 1.9–2.2(24H, CH$_3$COO-x8), 2.6–3.2(1H, m), 3.3–3.6(1H, m), 3.6–4.2(4H, m), 4.6–5.3(5H, m), 5.57(1H, t, J=10 Hz).

REFERENCE EXAMPLE 52

Octa-O-acetyl derivative of N-[(1S,2S)-(2,4/3,5)-2,3,4-trihydroxy-5-hydroxymethylcyclohexyl]valiolamine By treating N-[(1S,2S)-(2,4/3,5)-2,3,4-trihydroxy-5-hydroxymethylcyclohexyl]valiolamine (200 mg) in the same manner as in Reference Example 49, there is obtained the subject octa-O-acetyl derivative (330 mg).

$[\alpha]_D^{25} + 79.7°$ (c=1, CH$_3$OH).

Elemental analysis, for C$_{30}$H$_{43}$NO$_{17}$: Calcd.(%): C, 52.25; H, 6.28; N, 2.03. Found (%): C, 52.11; H, 6.36; N, 2.22.

NMR (CDCl$_3$)δ: 1.2–2.4(5H, m), 1.9–2.07(24H, CH$_3$COOx8), 3.2–3.46(2H, m), 3.65(1H, d, J=11.5 Hz), 3.84(1H, dd, J=3 Hz, 11.5 Hz), 4.00(1H, d, J=11.5 Hz), 4.12(1H, dd, J=6 Hz, 11.5 Hz), 4.80 (1H, dd, J=4.5 Hz, 10.5 Hz), 4.89(1H, dd, J=9 Hz, 10 Hz), 5.01(1H, dd, J=4.5 Hz, 10 Hz), 5.06(1H, d, J=10 Hz), 5.26 (1H, dd, J=9 Hz, 10.5 Hz), 5.62(1H, t, J=10 Hz).

REFERENCE EXAMPLE 53

4,7-O-Benzylidene-N-benzyloxycarbonylvalidamine

N-Benzyloxycarbonylvalidamine (produced in accordance with the procedure as described in the Japanese Patent Application No. 144309/1981, pp. 30) (55.3 g) is dissolved in dimethylformamide (190 ml), and α,α-dimethoxytoluene (27.7 g) and p-toluenesulfonic acid (177 mg) are added to the solution, followed by stirring under reduced pressure (60 to 65 mmHg) at 60° to 65° C. for 1 hour. The reaction mixture is concentrated under reduced pressure, and the residue is dissolved in ethyl acetate (600 ml). The ethyl acetate extract is washed with water and saturated aqueous sodium hydrogen carbonate, dried over anhydrous sodium sulfate, and concentrated under reduced pressure. Toluene is added to the residue, and the mixture is again concentrated under reduced pressure, and addition of ethyl ether (200 ml) and petroleum ether (2 l) to the residue produces white powdery 4,7-O-benzylidene-N-benzyloxycarbonylvalidamine (67.7 g).

$[\alpha]_D^{24} + 54.1°$ (c=1, CH$_3$OH).

Elemental analysis, for C$_{22}$H$_{25}$NO$_6$: Calcd.(%): C, 66.15; H, 6.31; N, 3.51. Found (%): C, 66.07; H, 6.43; N, 3.39.

NMR (DMSO-d$_6$)δ: 0.8–2.2(3H, m), 3.1–4.2(6H, m), 4.70(1H, d, J=5 Hz), 4.78(1H, d, J=4.5 Hz), 5.02(2H, s), 5.47(1H, s), 6.98(1H, d, J=7.5 Hz), 7.2–7.6(10H, m).

REFERENCE EXAMPLE 54

4-O-Benzoyl-N-benzyloxycarbonyl-7-bromo-7-deoxyvalidamine 4,7-O-Benzylidene-N-benzyloxycarbonylvalidamine (42.5 g) is dissolved in a mixture of carbon tetrachloride (500 ml) and 1,1,2,2-tetrachloroethane (100 ml), and N-bromosuccinimide (21.5 g) and barium carbonate (35 g) are added to the solution, followed by reflux with stirring for 1 hour. The reaction mixture is filtered when hot, and the insoluble matter is washed with carbon tetrachloride. The filtrate and washings are combined and concentrated under reduced pressure. The residue is dissolved in ethyl acetate, and the solution is washed with 2N hydrochloric acid and saturated aqueous sodium hydrogen carbonate, dried over anhydrous sodium sulfate and freed of the solvent under reduced pressure. The residue is chromatographed on a column of silica gel (600 ml), and after the column is washed with toluene-ethyl acetate (4:1), elution is performed with toluene-ethyl acetate (1:1). The eluate is concentrated under reduced pressure, and ethyl ether-petroleum ether (1:5, about 800 ml) is added to the residue, which is then left standing overnight in a refrigerator. By this procedure, there is obtained white precipitate (29.8 g) of 4-O-benzoyl-N-benzyloxycarbonyl-7-bromo-7-deoxyvalidamine.

Elemental analysis, for C$_{22}$H$_{24}$NO$_6$Br: Calcd.(%): C, 55.24; H, 5.06; N, 2.93; Br, 16.70. Found (%): C, 55.14; H, 5.02; N, 2.62; Br, 16.65.

NMR (DMSO-d$_6$)δ: 1.3–1.75(1H, m), 1.8–2,6(2H, m), 2.9–4.2(m), 4.87(1H, t, J=9 Hz), 5.07(2H, s), 7.08(1H, d, J=8 Hz), 7.40(5H, s), 7.25–7.75(3H, m), 7.95–8.15(2H, m).

REFERENCE EXAMPLE 55

4-O-Benzoyl-N-benzyloxycarbonyl-2,3-O-cyclohexylidene-7-bromo-7-deoxyvalidamine

4-O-Benzoyl-N-benzyloxycarbonyl-7-bromo-7-deoxyvalidamine (20 g) is dissolved in dimethylformamide (50 ml), and 1,1-dimethoxycyclohexane (20 ml) and p-toluenesulfonic acid (0.5 g) are added to the solution, followed by stirring under reduced pressure (45 to 50 mmHg) at 55° C. for 2 hours. The reaction mixture is dissolved in ethyl acetate, which is washed with saturated aqueous sodium hydrogen carbonate, dried over anhydrous sodium sulfate and concentrated under reduced pressure. The residue is chromatographed on a column of silica gel (550 ml), and the column is washed with toluene, followed by elution with toluene-ethyl acetate (19:1). The eluate is concentrated under reduced pressure, and the residue is dried in a desiccator under reduced pressure to give syrupy 4-O-benzoyl-N-benzyloxycarbonyl-2,3-O-cyclohexlidene-7-bromo-7-deoxyvalidamine (25.5 g).

Elemental analysis, for C$_{28}$H$_{32}$NO$_6$Br: Calcd.(%): C, 60.21; H, 5.78; N, 2.51; Br, 14.31. Found (%): C, 60.69; H, 5.71; N, 2.49; Br, 14.61.

NMR (CDCl$_3$)δ: 1.2–1.8(10H, m), 3.42(2H, d, J=5 Hz), 3.66(1H, dd, J=4 Hz, 10 Hz), 3.88(1H, t, J=10 Hz), 4.27(1H, m), 4.97(1H, d, J=5 Hz), 5.13(2H, s), 5.33(1H, t, J=10 Hz), 7.1–7.7(3H, m), 7.38(5H, s), 8.0–8.2(2H, m).

REFERENCE EXAMPLE 56

4-O-Benzoyl-N-benzyloxycarbonyl-2,3-O-cyclohexylidene-7-deoxyvalidamine

4-O-Benzoyl-N-benzyloxycarbonyl-2,3-O-cyclohexylidene-7-bromo-7-deoxyvalidamine (25 g) is dissolved in toluene (300 ml), and tri-n-butyltin hydride (20 ml) and α,α'-azobisiso-butyronitrile (0.1 g) are added to the solution, followed by reflux for 1 hour. The reaction mixture is cooled to room temperature, washed with 1N hydrochloric acid and saturated aqueous sodium hydrogen carbonate, dried over anhydrous sodium sulfate and concentrated under reduced pressure. The residue is chromatographed on a column of silica gel (600 ml), and the column is washed with toluene, followed by elution with toluene-ethyl acetate (9:1). The eluate is concentrated under reduced pressure, and the residue is dried in a desiccator under reduced pressure to produce syrupy 4-O-benzoyl-N-benzyloxycarbonyl-2,3-O-cyclohexylidene-7-deoxyvalidamine (21 g).

Elemental analysis, for C$_{28}$H$_{33}$NO$_6$: Calcd.(%): C, 70.12; H, 6.94; N, 2.92. Found (%): C, 70.58; H, 6.95; N, 2.71.

NMR (CDCl$_3$)δ: 0.96(3H, d, J=6.5 Hz), 1.15-2.2(12H, m), 2.2-2.6 (1H, m), 3.63(1H, dd, J=4 Hz, 10 Hz), 3.83(1H, t, J=10 Hz), 4.22(1H, m) 4.9-5.25(2H, m), 5.13(2H, s), 7.15-7.7(3H, m), 7.38(5H, s), 8.0-8.2(2H, m)

REFERENCE EXAMPLE 57

N-Benzyloxycarbonyl-2,3-O-cyclohexylidene-7-deoxyvalidamine

4-O-Benzoyl-N-benzyloxycarbonyl-2,3-O-cyclohexylidene-7-deoxyvalidamine (20 g) is dissolved in acetone-ethanol (3:2, 500 ml), and 1N sodium hydroxide (100 ml) is added to the solution, followed by stirring at room temperature for 1 hour. The reaction mixture is adjusted under ice-cooling by iced-cooled water to pH 4.5 with 2N hydrochloric acid and then adjusted to pH 7.5 with 25 to 28% aqueous ammonia. Water (about 500 ml) is added to the solution, and the organic solvent is distilled off under reduced pressure. The oily resultant material is extracted with ethyl acetate, and the extract is washed with saturated aqueous sodium hydrogen carbonate, dried over anhydrous sodium sulfate and freed of the solvent under reduced pressure. The residue is chromatographed on a column of silica gel (550 ml), and elution is performed with toluene-ethyl acetate (3:1). The eluate is concentrated under reduced pressure, and to the residue is added ethyl ether-petroleum ether (1:4, 500 ml), which is left on standing overnight in a refrigerator to give crystalline N-benzyloxycarbonyl-2,3-O-cyclohexylidene-7-deoxyvalidamine (13.9 g).

Elemental analysis, for C$_{21}$H$_{29}$NO$_5$: Calcd.(%): C, 67.18; H, 7.79; N, 3.73. Found (%): C, 67.02; H, 7.70; N, 3.55.

NMR (CDCl$_3$)δ: 1.03(3H, d, J=7 Hz), 1.1-1.9(12H, m), 2.1-2.4(1H, m), 2.45(1H, d, J=4 Hz), 3.15-3.6(3H, m), 4.17(1H, m), 4.89(1H, d, J=6 Hz), 5.10(2H, s), 7.37(5H, s).

REFERENCE EXAMPLE 58

(2R)-(2,6/3,4)-2,3-O-Cyclohexylidene-4-benzyloxycarbonylamino-2,3-dihydroxy-6-methylcyclohexanone A solution of anhydrous trifluoroacetic acid (13.5 ml) in dichloromethane (50 ml) is added dropwise to a solution of dimethylsulfoxide (9 ml) in dichloromethane (50 ml) under cooling to not more than −65° C., and the solution is stirred at the same temperature for 20 minutes. Then, N-benzyloxycarbonyl-2,3-O-cyclohexylidene-7-deoxyvanlidamine (12 g) is added to the solution under cooling to not more than −70' C., followed by stirring at the same temperature for 1 hour. After a solution of triethylamine (26.7 ml) in dichloromethane (50 ml) is added dropwise to the reaction mixture under cooling to not more than −65° C., the cooling bath is removed, and the reaction mixture is stirred until its temperature rises to 20° C., and poured into ice-cooled water (about 300 ml), followed by stirring for 1 hour. The dichloromethane layer is separated, and the water layer is extracted again with dichloromethane. The dichloromethane extracts are combined, washed with 2N hydrochloric acid and saturated aqueous sodium hydrogen carbonate, dried over anhydrous sodium sulfate and concentrated under reduced pressure. The residue is chromatographed on a column of silica gel (400 ml), and elution is performed with toluene-ethyl acetate (5:1). The eluate is concentrated under reduced pressure, and the residue is dried in a desiccator under reduced pressure to produce (2R)-(2,6/3,4)-2,3-O-cyclohexylidene-4-benzyloxycarbonylamino-2,3-dihydroxy-6-methylcyclohexanone (9.8 g) as a syrupy material.

Elemental analysis, for C$_{21}$H$_{27}$NO$_5$: Calcd.(%): C, 67.54; H, 7.29; N, 3.75. Found (%): C, 67.49; H, 7.41; N, 3.67.

NMR (CDCl$_3$)δ: 1.06(3H, d, J=6 Hz), 1.2-1.9(11H, m), 2.3-2.85(2H, m), 3.74(1H, dd, J=4 Hz, 10.5 Hz), 4.2-4.45(1H, m), 4.43(1H, d, J=10.5 Hz), 5.14(2H, s), 5.15-5.4(1H, m), 7.40(5H, s).

REFERENCE EXAMPLE 59

2,3-Di-O-benzyl-1,6-anhydro-4-O-(2,3-di-O-benzyl-6-deoxy-α-D-xylo-4-hexopyranoseurosyl)-β-D-glucopyranose Dimethylsulfoxide (19.5 ml) is dissolved in dichloromethane (19.5 ml), to which is added dropwise a solution of trifluoroacetic anhydride (29 ml) in dichloromethane (130 ml) at −65° C. or below, followed by stirring at the same temperature for 15 minutes. Then, to the mixture is then added 2,3-di-O-benzyl-1,6-anhydro-4-O-(2,3-di-O-benzyl-6-deoxy-α-D-glucopyransoyl)-β-D-glucopyranose [2,3,2',3'-tetra-O-benzyl-1,6-anhydro-6'-deoxymaltose] (45.3 g) under cooling to −70° C. or below, and the mixture is stirred at the same temperature for 2 hours. After a solution of triethylamine (54.5 ml) in dichloromethane (160 ml) is added dropwise to the reaction mixture under cooling to −65° C. or below, the cooling bath is removed, and stirring is continued until the reaction temperature rises to room temperature. After the reaction mixture is poured into ice-cold water (1.3 l) and the mixture is stirred, the dichloromethane layer is separated, and the water layer is extracted twice with dichloromethane (200 ml). The dichloromethane extracts are combined, washed with 0.5N hydrochloric acid, saturated aqueous sodium hydrogen carbonate and water successively, dried over anhydrous sodium sulfate and concentrated under reduced pressure. The residue is chromatographed on a column of silica gel (1 l), and the column is washed with toluene (1.5 l), followed by elution with toluene-ethyl acetate (9:1) and toluene-ethyl acetate (4:1). The eluate is concentrated under reduced pressure and then dried further in a desiccator under reduced pressure to give syrupy, 2,3-di-O-benzyl-1,6-anhydro-4-O-(2,3-di-O-benzyl-6-deoxy-α-D-xylo-4-hexopyranoseurosyl)-β-D-glycopyranose (40.7 g). [α]$_D^{25}$+55.7° (c=1, CH$_3$OH).

Elemental analysis, for C$_{40}$H$_{42}$O$_9$: Calcd.(%): C, 72.05; H, 6.35. Found (%): C, 72.29; H, 6.43.

IR $\nu_{max}^{Nujol}$ cm$^{-1}$: 1745.

NMR (CDCl$_3$)δ: 1.26(3H, d, J=7 Hz), 3.30-3.85 (6H, m), 4.02(1H, d, J=9 Hz), 4.30-4.95(10H, m), 5.02(1H, d, J=3 Hz), 5.38(1H, s), 7.2-7.5(20H, m).

EXAMPLE 1

Methyl 4-[(1S,2S)-(2,4/3,5)-2,3,4-trihydroxy-5-hydroxymethylcyclohexyl]amino-4,6-dideoxy-α-D-glucopyranoside and its 6-deoxygalactopyranoside isomer Validamine (2.0 g) and methyl 2,3-O-cyclohexylidene-6-deoxy-α-D-xylo-hexopyranoside-4-urose (methyl 2,3-O-cyclohexylidene-6-deoxy-α-D-xylo-4-hexopyraneuroside) (5.5 g) are dissolved in dimethylformamide (50 ml), and 2N hydrochloric acid (1.5 ml) and sodium cyanoborohydride (2.6 g) are added to the solution, followed by stirring at 60° to 70° C. for 20 hours. The reaction mixture is concentrated under reduced pressure, and toluene is further added to the concentrate to distill off the dimethylformamide under reduced pressure azeotropically. The residue is dissolved in water (150 ml), and Dowex 50W×8 (H+ type, produced by Dow Chemical Co., U.S.A.) (150 ml) is added to the solution, followed by stirring at room temperature for 2 hours. The mixture is poured onto a column packed with Dowex 50W×8 (H+ type, 30 ml), and the column is washed with water (1 l), followed by elution with 0.5N aqueous ammonia. The eluate (0.7 to 1.1 l) is concentrated under reduced pressure, and the concentrate (ca. 15 ml) is chromatographed on a column of Amberlite CG-50 (NH$_4$+ type, produced by Rohm & Haas Co., U.S.A.) (250 ml), followed by elution with water. The eluate (170 to 250 ml) is concentrated under reduced pressure, and the concentrate (ca. 10 ml) is chromatographed on a column of Dowex 1×2 (OH− type, produced by Dow Chemical Co., U.S.A.) (1 l) followed by elution with water to give two fractional components. The first fraction (0.68 to 1.24 l) and the subsequent one (1.25 to 2.74 l) are concentrated under reduced pressure, respectively. The concentrate of the first fraction (ca. 20 ml) is again chromatographed on a column of Dowex 1×2 (OH− type, 850 ml), and after elution with water, the eluate (590 to 1045 ml) is concentrated under reduced pressure and lyophilized to give the 6-deoxygalactopyranoside isomer (160 mg). The concentrate of the later fraction (ca. 20 ml) is again chromatographed likewise on a column of Dowex 1×2 (OH− type, 1 l), and after elution with water, the eluate (1.33 to 2.75 l) is concentrated under reduced pressure and lyophilized to produce the 6-deoxyglycopyranoside isomer (415 mg).

The first eluted isomer (6-deoxygalactopyranoside isomer): $[\alpha]_D^{22} +162.0°$ (c=1, H$_2$O).

Elemental analysis, for C$_{14}$H$_{27}$NO$_8$.H$_2$O: Calcd.(%): C, 47.31; H, 8.23; N, 3.94. Found (%): C, 47.30; H, 8.35; N, 3.94.

NMR (D$_2$O)δ: 1.2–2.4 (3H, m), 1.53(3H, d, J=6.5 Hz), 3.08(1H), 3.2–4.5(9H, m), 3.61(3H, s), ~5.0(1H).

IC$_{50}$ (saccharase): 5.6×10$^{-6}$M.

TLC: Rf=0.36.

The later eluted isomer (6-deoxyglucopyranoside isomer): $[\alpha]_D^{22} +1.45.9°$ (c=1, H$_2$O).

Elemental analysis, for C$_{14}$H$_{27}$NO$_8$.H$_2$O: Calcd.(%): C, 47.31; H, 8.23; N, 3.94. Found (%): C, 47.37; H, 8.06; N, 4.04.

NMR (D$_2$O)δ: 1.3–2.3(3H, m), 1.52(3H, d, J=6.5 Hz), 2.61(1H, t, J=10 Hz), 3.3–4.15(9H, m), 3.62(3H, s), ~4.95(1H).

IC$_{50}$ (maltase): 1.8×10$^{-6}$M.

IC$_{50}$ (saccharase): 7.4×10$^{-7}$M.

TLC: Rf=0.48.

EXAMPLE 2

Methyl 4-[(1S,2S)-(2,4,5(OH)/3,5(CH$_2$OH))-2,3,4,5-tetrahydroxy-5-hydroxymethylcyclohexyl]amino-4,6-dideoxy-α-D-glucopyranoside and its 6-deoxygalactopyranoside isomer Valiolamine (2.0 g) and methyl 2,3-O-cyclohexylidene-6-deoxy-α-D-xylo-hexopyranoside-4-urose (5.3 g) are dissolved in dimethylformamide (50 ml), and 2N hydrochloric acid (1.5 ml) and sodium cyanoborohydride (2.6 g) are added to the solution, followed by stirring at 65° C. for 15 hours. The reaction mixture is concentrated under reduced pressure, and toluene is further added to the concentrate to distill off the dimethylformamide under reduced pressure azeotropically. The residue is dissolved in water (150 ml), and Dowex 50W×8 (H+ type, produced by Dow Chemical Co., U.S.A.) (150 ml) is added to the solution, which is stirred at room temperature for 2 hours. The mixture is poured onto a column packed with Dowex 50W×8 (H+ type, 30 ml), and the column is washed with water, followed by elution with 0.5N aqueous ammonia. The eluate (0.65 to 1.33 l) is concentrated under reduced pressure, and the concentrate (ca. 20 ml) is chromatographed on a column of Amberlite CG-50 (NH$_4$+ type, produced by Rohm & Haas Co., U.S.A.) (250 ml), followed by elution with water. The eluate (150 to 230 ml) is concentrated under reduced pressure, and the residue is chromatographed on a column of Dowex 1×2 (OH− type, produced by Dow Chemical Co., U.S.A.) (1.5 l), followed by elution with water to allow the separation into two components. The first eluted fraction is concentrated under reduced pressure and lyophilized to produce the 6-deoxygalactopyranoside isomer (0.25 g), while the later eluted fraction is concentrated under reduced pressure and lyophilized to produce the 6-deoxyglucopyranoside isomer (1.47 g).

The first eluted isomer (6-deoxygalactopyranoside isomer): $[\alpha]_D^{22} +130.7°$ (c=1, H$_2$O).

Elemental analysis, for C$_{14}$H$_{27}$NO$_9$.½H$_2$O: Calcd.(%): C, 46.40; H, 7.79; N, 3.87. Found (%): C, 46.34; H, 8.09; N, 3.51.

NMR (D$_2$O)δ: 1.53 (3H, d, J=6.5 Hz), 1.70(1H, dd, J=3 Hz, 15.5 Hz), 2.33 (1H, dd, J=3 Hz, 15.5 Hz), 3.17(1H, dd, J=5 Hz, 4 Hz), 3.45–4.55(9H, m), 3.61(3H, s), 5.0(1H, d, J=4 Hz).

IC$_{50}$ (maltase): 6.5×10$^{-7}$M.

IC$_{50}$ (saccharase): 2.5×10$^{-7}$M.

TLC: Rf=0.32.

The later eluted isomer (6-deoxyglucopyranoside isomer): $[\alpha]_D^{22} +105.6°$ (c=1, H$_2$O).

Elemental analysis, for C$_{14}$H$_{27}$NO$_9$.½H$_2$O: Calcd.(%): C, 46.40; H, 7.79; N, 3.87. Found (%): C, 46.64; H, 8.52; N, 3.46.

NMR (D$_2$O)δ: 1.48(3H, d, J=6 Hz), 1.71(1H, dd, J=3 Hz, 15.5 Hz), 2.21 (1H, dd, J=3 Hz, 15.5 Hz), 2.60(1H, t, J=9 Hz), 3.37–4.35(9H, m), 3.55(3H, s), ~4.8(1H).

IC$_{50}$ (maltase): 4.9×10$^{-9}$M.

IC$_{50}$ (saccharase): 1.0×10$^{-8}$M.

TLC: Rf=0.44.

EXAMPLE 3

Methyl 4-[(1S,2S)-(2,4/3,5)-2,3,4-trihydroxy-5-hydroxymethyl-cyclohexyl]amino-4-deoxy-α-D-glucopyranoside and its galactopyranoside isomer Validamine (2.0 g) and methyl 6-O-acetyl-2,3-O-cyclohexylidene-α-D-xylo-hexopyranoside-4-urose (methyl 6-O-acetyl-2,3-O-cyclohexylidene-α-D-xylo-4-hexopyranoseuroside) (4.7 g) are dissolved in dimethylformamide (35 ml), and 2N hydrochloric acid (1.5 ml) and sodium cyanoborohydride (2.6 g) are added to the solution, followed by stirring at 60° to 70° C. for 18 hours. The reaction mixture is concentrated under reduced pressure, and the residue is dissolved in 50% aqueous methanol (150 ml). Dowex 50W×8 (H+ type, produced by Dow Chemical Co., U.S.A.) (150 ml) is added to the solution, which is then stirred at room temperature for 1.5 hours. The mixture is poured onto a column packed with Dowex 50W×8 (H+ type, 30 ml), and the column is washed with water (700 ml), followed by elution with 0.5N aqueous ammonia. The eluate (0.7 to 1.5 l) is concentrated to dryness under reduced pressure, and the residue is dissolved in 4% aqueous ammonia (200 ml), followed by leaving at room temperature for 18 hours. The reaction mixture is concentrated to dryness under reduced pressure, and the residue is dissolved in water (ca. 10 ml) and chromatographed on a column of Amberlite CG-50 ($NH_4^+$ type, produced by Rohm & Haas Co., U.S.A.) (450 ml), followed by elution with water. The eluate (210 to 305 ml) is concentrated under reduced pressure, and the concentrate (ca. 10 ml) is chromatographed on a column of Dowex 1×2 ($OH^-$ type, produced by Dow Chemical Co., U.S.A.) (850 ml), followed by elution with water to divide into three fractions as eluted in 0.57 to 0.95 l, 0.96 to 1.33 l and 1.34 to 2.09 l, respectively. The fraction eluted in 1.34 to 2.09 l is concentrated under reduced pressure and lyophilized to give white powder (190 mg) of the glucopyranoside isomer. The fraction eluted in 0.96 to 1.33 l is concentrated under reduced pressure, and the concentrate (ca. 10 ml) is again chromatographed on a column of Dowex 1×2 ($OH^-$ type, 270 ml), followed by elution with water. The fraction eluted in 210 to 360 ml in this chromatographic method is combined with the fraction eluted in 0.57 to 0.95 l in the first chromatographic method, followed by concentration under reduced pressure. The concentrate (ca. 10 ml) is chromatographed on a column of Amberlite CG-50 ($NH_4^+$ type, 250 ml), and elution is performed with water. The eluate (150 to 180 ml) is concentrated under reduced pressure and lyophilized to give white powder galactopyranoside isomer (60 mg).

Glucopyranoside isomer: $[\alpha]_D^{23} + 142.0°$ (c=1, $H_2O$).

Elemental analysis, for $C_{14}H_{27}NO_9 \cdot H_2O$: Calcd. (%): C, 45.28; H, 7.87; N, 3.77. Found (%): C, 44.99; H, 8.45; N, 3.87.

NMR ($D_2O$)δ: 1.3-2.3 (3H, m), 2.87 (1H, t, J=10 Hz), 3.35-4.25 (11H, m), 3.66 (3H, S), 5.03 (1H, d, J=3.5 Hz).

$IC_{50}$ (maltase): $4.4 \times 10^{-6}$M.
$IC_{50}$ (saccharase): $5.8 \times 10^{-7}$M.
TLC: Rf=0.43.

Galactopyranoside isomer: $[\alpha]_D^{23} + 144.1°$ (c=1, $H_2O$).

Elemental analysis, for $C_{14}H_{27}NO_9$: Calcd. (%): C, 47.58; H, 7.70; N, 3.96. Found (%): C, 47.53; H, 8.21; N, 4.14.

$IC_{50}$ (saccharase): $1.0 \times 10^{-6}$M.
TLC: Rf=0.36.

EXAMPLE 4

Methyl 4-[(1S,2S)-(2,4,5(OH)/3,5($CH_2OH$))-2,3,4,5-tetrahydroxy-5-hydroxymethylcyclohexyl]amino-4-deoxy-α-D-glucopyranoside and its galactopyranoside isomer Valiolamine (2.0 g) and methyl 6-O-acetyl-2,3-O-cyclohexylidene-α-D-xylo-hexopyranoside-4-urose (5.5 g) are dissolved in dimethylformamide (35 ml), and 2N hydrochloric acid (1.5 ml) and sodium cyanoborohydride (2.6 g) are added to the solution, followed by stirring at 60° to 70° C. for 18 hours. The reaction mixture is concentrated under reduced pressure, and the residue is dissolved in 50% aqueous methanol (150 ml). Dowex 50W×8 ($H^+$ type, produced by Dow Chemical Co., U.S.A.) (150 ml) is added to the solution, which is then stirred at room temperature for 1.5 hours. The mixture is poured onto a column of Dowex 50W×8 ($H^+$ type, 30 ml), and the column is washed with water (700 ml), followed by elution with 0.5N aqueous ammonia. The eluate (0.7 to 1.5 l) is concentrated under reduced pressure to dryness, and the residue is dissolved in 4% aqueous ammonia (200 ml), followed by leaving on standing at room temperature for 15 hours. The reaction mixture is concentrated under reduced pressure, and the residue is dissolved in water (ca. 10 ml) and chromatographed on a column of Amberlite CG-50 ($NH_4^+$ type, produced by Rohm & Haas Co., U.S.A.) (450 ml), followed by elution with water. The eluate (250 to 340 ml) is concentrated under reduced pressure, and the concentrate (ca. 10 ml) is chromatographed on a column of Dowex 1×2 ($OH^-$ type, produced by Dow Chemical Co., U.S.A.) (850 ml), followed by elution with water to divide into three fractions as eluted in 0.57 to 1.14 l, 1.15 to 1.71 l and 1.72 to 2.85 l, respectively. The fraction eluted in 1.77 to 2.85 l is concentrated under reduced pressure and lyophilized to give white powder (375 mg) of the glucopyranoside isomer. The fraction eluted in 1.15 to 1.71 l is concentrated under reduced pressure, and the concentrate (ca. 10 ml) is again chromatographed on a column of Dowex 1×2 ($OH^-$ type, 270 ml), followed by elution with water. The fraction eluted in 250 to 550 ml in this chhromatographic method and the fraction eluted in 0.57 to 1.14 l in the first chromatographic method with Dowex 1×2 are combined and concentrated under reduced pressure, and then concentrate (ca. 10 ml) is chromatographed on a column of Amberlite CG-50 ($NH_4^+$ type, 250 ml), followed by elution with water. The eluate (160 to 200 ml) is concentrated under reduced pressure and lyophilized to give white powder (160 mg) of the galactopyranoside isomer.

Glucopyranoside isomer: $[\alpha]_D^{23} + 102.1°$ (c=1, $H_2O$).

Elemental analysis, for $C_{14}H_{27}NO_{10} \cdot \frac{1}{2}H_2O$: Calcd. (%): C, 44.44; H, 7.46; N, 3.70. Found (%): C, 44.85; H, 7.85; N, 3.82.

NMR ($D_2O$)δ: 1.78 (1H, dd, J=3.3 Hz, 15 Hz), 2.25 (1H, dd, J=3 Hz, 15 Hz), 2.92 (1H, t, J=10 Hz), 3.55-4.2 (11H, m), 3.62 (3H, s), 5.03 (1H, d, J=3.8 Hz).

$IC_{50}$ (maltase): $7.2 \times 10^{-8}$M.
$IC_{50}$ (saccharase): $8.0 \times 10^{-8}$M.
TLC: Rf=0.35.

Galactopyranoside isomer: $[\alpha]_D^{23} + 105.4°$ (c=1, $H_2O$).

Elemental analysis, for $C_{14}H_{27}NO_{10} \cdot H_2O$: Calcd. (%): C, 43.41; H, 7.55; N, 3.62. Found (%): C, 43.36; H, 8.08; N, 4.01.

$IC_{50}$ (maltase): $3.2 \times 10^{-7}$M.
$IC_{50}$ (saccharase): $6.2 \times 10^{-7}$M.
TLC: Rf=0.33.

EXAMPLE 5

[(1S,2S)-(2,4/3,5)-2,3,4-Trihydroxy-5-hydroxymethylcyclohexyl][(2S)-(2,6/3,4)-4-benzyloxycarbonylamino-2,3-dihydroxy-6-hydroxy-methylcyclohexyl]amine Validamine (1.5 g) and (2R)-(2,6/3,4)-1,3-diacetoxy-4-benzyloxycarbonylamino-6-trityloxymethylcyclohexanone (5.4 g) are dissolved in dimethylformamide (35 ml), and 2N hydrochloric acid (1.15 ml) and sodium cyanoborohydride (2.0 g) are added to the solution, followed by stirring at 60° to 70° for 15 hours. The reaction mixture is concentrated under reduced pressure, and the residue is added to a mixture of water and ethyl acetate. The ethyl acetate layer is separated and the water layer is extracted with ethyl acetate. The ethyl acetate extracts are collected, washed with water, dried over sodium sulfate and concentrated under reduced pressure. Ethyl ether is added to the residue, and the resulting syrup is dissolved in a mixture (300 ml) of 10% aqueous ammoniaethanol (1:2), followed by stirring overnight at room temperature. The reaction mixture is concentrated under reduced pressure, and the residue is dissolved in 80% aqueous acetic acid (200 ml), followed by stirring at 80° C. for 2 hours. The reaction mixture is concentrated under reduced pressure, and the residue is added to a mixture of water and ethyl acetate. The water layer is separated and chromatographed on a column of Dowex 50W×8 (H+ type, produced by Dow Chemical Co., U.S.A.) (150 ml), and the column is washed with water, followed by elution with 0.5N aqueous ammonia. The eluate is concentrated under reduced pressure, and the concentrate (20 ml) is chromatographed on a column of Amberlite CG-50 ($NH_4^+$ type, produced by Rohm & Haas Co., U.S.A.) (250 ml), followed by elution with water. The eluate is concentrated under reduced pressure and lyophilized to give [(1S,2S)-(2,4/3,5)-2,3,4-trihydroxy-5-hydroxymethylcyclohexyl][(2S)-(2,6/3,4)-4-benzyloxycarbonylamine-2,3-dihydroxy-6-hydroxymethylcyclohexyl]amine (980 mg).

$[\alpha]_D^{23} +37.4°$ (c=0.5, $H_2O$).

Elemental analysis, for $C_{22}H_{34}N_2O_9 \cdot \frac{1}{2}H_2O$: Calcd. (%): C, 55.10; H, 7.36; N, 5.84. Found (%): C, 55.15; H, 7.35; N, 5.71.

$IC_{50}$ (saccharase): $7.0 \times 10^{-7}$M.

TLC: Rf=0.65.

EXAMPLE 6

[(1S,2S)-(2,4/3,5)-2,3,4-Trihydroxy-5-hydroxymethylcyclohexyl][(1S,2S)-(2,6/3,4)-4-amino-2,3-dihydroxy-6-hydroxymethyl]amine and
[(1S,2S)-(2,4/3,5)-2,3,4-trihydroxy-5-hydroxymethylcyclohexyl][(1R,2S)-(2,6/3,4)-4-amino-2,3-dihydroxy-6-hydroxymethyl]amine

[(1S,2S)-(2,4/3,5)-2,3,4-Trihydroxy-5-hydroxymethylcyclohexyl][(2S)-(2,6/3,4)-4-benzyloxycarbonylamino-2,3-dihydroxy-6-hydroxymethylcyclohexyl]amine (880 mg) is dissolved in water (150 ml), and acetic acid (1 ml) and palladium black (300 mg) are added to the solution, followed by stirring in a stream of hydrogen at room temperature for 4 hours. After the conclusion of the reaction, the catalyst is filtered out and washed with water. The filtrate and washings are combined and concentrated to dryness under reduced pressure, The residue is dissolved in water (ca. 20 ml) and chromatographed on a column of Amberlite CG-50 ($NH_4^+$ type, produced by Rohm & Haas Co., U.S.A.) (250 ml), and the column is washed with water, followed by elution with 0.1N aqueous ammonia to give two fractional components.

The first fraction (as eluted in 1.45 to 1.90 l) is concentrated under reduced pressure and lyophilized to produce white powder (80 mg), while the later fraction (as eluted in 2.0 l to 2.9 l) is concentrated under reduced pressure and lyophilized to give white powder (370 mg).

The first eluted isomer: $[\alpha]_D^{22} +66.4°$ (c=0.5, $H_2O$).

Elemental analysis, for $C_{14}H_{28}N_2O_7 \cdot H_2O$: Calcd. (%): C, 47.44; H, 8.53; N, 7.91. Found (%): C, 47.38; H, 8.11; N, 7.68.

$IC_{50}$ (maltase): $2.9 \times 10^{-6}$M.
$IC_{50}$ (saccharase): $1.6 \times 10^{-6}$M.

The later eluted isomer: $[\alpha]_D^{22} +24.5°$ (c=1.0, $H_2O$).
Elemental analysis, for $C_{14}H_{28}N_2O_7 \cdot H_2O$: Calcd. (%): C, 47.44; H, 8.53; N, 7.91. Found (%): C, 47.52; H, 8.38; N, 7.61.

$IC_{50}$ (saccharase): $7.8 \times 10^{-5}$M.

EXAMPLE 7

[(1S,2S)-(2,4,5(OH)/3,5($CH_2OH$))-2,3,4,5-Tetrahydroxy-5-hydroxymethylcyclohexyl][(1S,2S)-(2,6/3,4)-4-benzyloxycarbonylamino-2,3-dihydroxy-6-hydroxymethylcyclohexyl]amine and
[(1S,2S)-(2,4,5(OH)/3,5($CH_2OH$))-2,3,4,5-tetrahydroxy-5-hydroxymethylcyclohexyl][(1R,2S)-(2,6/3,4)-4-benzyloxycarbonylamino-2,3-dihydroxy-6-hydroxymethylcyclohexyl]amine Valiolamine (2.0 g) and (2R)-(2,6/3,4)-1,3-diacetoxy-4-benzyloxycarbonylamino-6-trityloxymethylcyclohexanone (7.3 g) are dissolved in dimethylformamide (50 ml), and 2N hydrochloric acid (1.5 ml) and sodium cyanoborohydride (2.6 g) are added to the solution, followed by stirring at 60° to 70° C. for 17 hours. The reaction mixture is concentrated under reduced pressure, and the residue is added to a mixture of water and ethyl acetate to allow the distribution. The ethyl acetate layer is separated, and the water layer is extracted with ethyl acetate. The ethyl acetate extracts are combined, washed with water, dried over sodium sulfate and concentrated under reduced pressure. The residue is dissolved in a mixture (300 ml) of 10% aqueous ammonia-ethanol (1:2), and the solution is stirred overnight at room temperature. The reaction mixture is concentrated to dryness under reduced pressure, and the residue is dissolved in 80% aqueous acetic acid (200 ml), followed by stirring at 80° C. for 2 hours. The reaction mixture is concentrated under reduced pressure, and the residue is added to a mixture of water and ethyl acetate to cause distribution of the component to the respective solvents. The water layer is separated and chromatographed on a column of Dowex 50W×8 (H+ type, produced by Dow Chemical Co., U.S.A.) (150 ml), and the column is washed with water, followed by elution with 0.5N aqueous ammonia. The eluate is concentrated under reduced pressure, and the concentrate (ca. 15 ml) is chromatographed on a column of Amberlite CG-50 ($NH_4^+$ type, produced by Rohm & Haas Co., U.S.A.) (250 ml), followed by elution with water to give two fractional components. The eluates are each concentrated under reduced pressure and lyophilized to produce white powder (980 mg) from the first eluted fraction (90 to 290 ml) and white powder (305 mg) from the later eluted one (300 to 780 ml), respectively.

The first eluted isomer: $[\alpha]_D^{23} -3.4°$ (c=0.5, $H_2O$).

Elemental analysis, for $C_{22}H_{34}N_2O_{10} \cdot H_2O$: Calcd. (%): C, 52.37; H, 7.19; N, 5.55. Found (%): C, 52.34; H, 6.98; N, 5.73.

TLC: Rf=0.62.

The later eluted isomer: $[\alpha]_D^{23} =8.2°$ (c=0.5, $H_2O$).

Elemental analysis, for $C_{23}H_{34}N_2O_{10} \cdot H_2O$: Calcd. (%): C, 52.37; H, 7.19; N, 5.55. Found (%): C, 52.49; H, 7.00; N, 5.52.

TLC: Rf=0.64.

EXAMPLE 8

[(1S,2S)-(2,4,5(OH)/3,5(CH$_2$OH))-2,3,4,5-Tetrahydroxy-5-hydroxymethylcyclohexyl][(1S,2S)-(2,6/3,4)-4-amino-2,3-dihydroxy-6-hydroxymethylcyclohexyl]amine and

[(1S,2S)-(2,4,5(OH)/3,5(CH$_2$OH))-2,3,4,5-tetrahydroxy-5-hydroxymethylcyclohexyl][(1R,2S)-(2,6/3,4)-4-amino-2,3-dihydroxy-6-hydroxymethylcyclohexyl]amine Among the 4-benzyloxycarbonylamino derivatives as obtained in Example 7, the first eluted component (980 mg) in the chromatography by use of Amberlite CG-50 is dissolved in water (150 ml) and acetic acid (0.4 ml) and palladium black (350 mg) are added to the solution, followed by stirring in a stream of hydrogen at room temperature for 4 hours. After the conclution of the reaction, the catalyst is filtered out and washed with water, and the filtrate and washings are combined and concentrated under reduced pressure. The residue is dissolved in water (ca. 10 ml), and chromatographed on a column of Amberlite CG-50 (NH$_4$+ type, produced by Rohm & Haas Co., U.S.A.) (250 ml), and the column is washed with water, followed by elution with 0.1N aqueous ammonia. The eluate is concentrated under reduced pressure and the residue is chromatographed on a column of Dowex 1×2 (OH$^-$ type, produced by Dow Chemical Co., U.S.A.) (250 ml), followed by elution with water. The eluate is concentrated under reduced pressure and lyophilized to give white powdery, the corresponding 4-amino derivative (340 mg).

$[\alpha]_4^{22}$ −9.4° (c=1, H$_2$O).

Elemental analysis, for C$_{14}$H$_{28}$N$_2$O$_8$.3/2H$_2$O: Calcd. (%): C, 44.32; H, 8.24; N, 7.38. Found (%): C, 44.25; H, 8.45; N, 7.18.

IC$_{50}$ (maltase): 3.3×10$^{-6}$M.

IC$_{50}$ (saccharase): 2.5×10$^{-7}$M.

Another 4-benzyloxycarbonylamino derivative as obtained in Example 7 (the later eluted component in the column chromatography by use of Amberlite CG-50) (110 mg) is dissolved in water (50 ml), and acetic acid (0.1 ml) and palladium black (35 mg) are added to the solution, followed by stirring in a stream of hydrogen at room temperature for 4 hours. After the conclusion of the reaction, the catalyst is filtered out and washed with water, and the filtrate and washings are combined and concentrated under reduced pressure. The residue is dissolved in water (ca. 10 ml), and chromatographed on a column of Amberlite CG-50 (NH$_4$+ type, produced by Rohm & Haas Co., U.S.A.) (130 ml), and the column is washed with water, followed by elution with 0.1N aqueous ammonia. The eluate is concentrated under reduced pressure and lyophilized to produce white powdery the corresponding 4-amino derivative (54 mg).

$[\alpha]_D^{22}$ +22.4° (c=0.5, H$_2$O).

Elemental analysis, for C$_{14}$H$_{28}$N$_2$O$_8$.2H$_2$O: Calcd. (%): C, 43.29; H, 8.30; N, 7.21. Found (%): C, 43.48; H, 8.35; N, 6.81.

IC$_{50}$ (maltase): 2.8×10$^{-6}$M.

IC$_{50}$ (saccharase): 2.3×10$^{-7}$M.

EXAMPLE 9

N-(2,3,5-Trihydroxy-6-hydroxymethyltetrahydropyran-4-yl)valiolamine and

N-(2,3-O-isopropylidene-2,3-dihydroxy-5-(1,2-dihydroxyethyl)tetrahydrofuran-4-yl)valiolamine Valiolamine (4.0 g) and 1,2:5,6-O-isopropylidene-α-D-ribo-hexofuranose-3-urose (8.0 g) are dissolved in dimethylformamide (100 ml), and 2N hydrochloric acid (3 ml) and sodium cyanoborohydride (5.2 g) are added to the solution, followed by strring at 60° to 70° C. for 15 hours. The reaction mixture is concentrated under reduced pressure, and further freed of the dimethylformamide azeotropically with toluene under reduced pressure. The residue is dissolved in water (1 l), and Dowex 50W×8 (H+ type, produced by Dow Chemical Co., U.S.A.) (400 ml) is added to the solution, followed by stirring at room temperature for 1 hour. The mixture is poured onto a column packed with Dowex 50W×8 (H+ type, 100 ml), and the column is washed with water, followed by elution with 0.5N aqueous ammonia. The eluate is concentrated under reduced pressure, and the residue is chromatographed on a column of Amberlite CG-50 (NH$_4$+ type, produced by Rohm & Haas Co., U.S.A.) (1.1 l), followed by elution with water to allow the separation into two components. The first eluted fraction (440 to 720 ml) is concentrated under reduced pressure, and the residue is chromatographed on a column of Dowex 1×2 (OH$^-$ type, produced by Dow Chemical Co., U.S.A.) (550 ml), followed by elution with water. The eluate is concentrated under reduced pressure and lyophilized to produce white powdery N-[2,3-O-isopropylidene-2,3-dihydroxy-5-(1,2-dihydroxyethyl)tetrahydrofuran-4-yl)valiolamine (28 g). The later eluted fraction (780 to 1050 ml) is concentrated under reduced pressure, and the residue is again chromatographed on a column of Amberlite CG-50 (NH$_4$+ type, 500 ml), followed by elution with water. The eluate is concentrated under reduced pressure and lyophilized to produce white powdery N-(2,3,5-trihydroxy-6-hydroxymethyltetrahydropyran-4-yl)valiolamine (1.05 g). The above mentioned isopropylidene derivative (450 mg) as obtained from the first eluted fraction is dissolved in water (50 ml), and Dowex 50W×8 (H+ type, 30 ml) is added to the solution, followed by stirring at 80° to 90° C. for 1 hour. The mixture is poured onto a column packed with Dowex 50W×8 (H+ type, 5 ml), and the column is washed with water, followed by elution with 0.5N aqueous ammonia. The eluate is concentrated under reduced pressure, and the residue is chromatographed on a column of Amberlite CG-50 (NH$_4$+ type, 250 ml), followed by elution with water. The eluate is concentrated under reduced pressure and lyophilized to produce white powdery N-(2,3,5-trihydroxy-6-hydroxymethyltetrahydropyran-4-yl)valiolamine (350 mg).

N-[2,3-O-isopropylidene-2,3-dihydroxy-5-(1,2-dihydroxyethyl)tetrahydrofuran-4-yl]valiolamine:

$[\alpha]_D^{23}$ +72.4° (c=1, H$_2$O).

Elemental analysis, for C$_{16}$H$_{29}$NO$_{10}$.H$_2$O: Calcd. (%): C, 46.48; H, 7.56; N, 3.39. Found (%): C, 46.71; H, 7.22; N, 3.47.

NMR (D$_2$O)δ: 1.51 (3H, s), 1.67 (1H, dd, J=3.5 Hz, 15 Hz), 2.27 (1H, dd, J=3 Hz, 15 Hz), 3.35–4.2 (11H, m), 5.06 (1H, t, J=4 Hz), 6.04 (1H, d, J=4 Hz).

IC$_{50}$ (saccharase): 3.7×10$^{-5}$M.

TLC: Rf=0.44.

N-(2,3,5-trihydroxy-6-hydroxymethyltetrahydropyran-4-yl)valiolamine: $[\alpha]_D^{23} +31.3°$ (c=1, $H_2O$).

Elemental analysis, for $C_{13}H_{25}NO_{10}\cdot\frac{1}{2}H_2O$: Calcd. (%): C, 42.85; H, 7.19; N, 3.84. Found (%): C, 42.56; H, 7.11; N, 3.84.

$IC_{50}$ (maltase): $1.1\times10^{-7}$M.
$IC_{50}$ (saccharase): $9.0\times10^{-8}$M.
TLC: Rf=0.31.

EXAMPLE 10

N-(2,3,5-Trihydroxy-6-hydroxymethyltetrahydropyran-4-yl)validamine and
N-(2,3-O-isopropylidene-2,3-dihydroxy-5-(1,2-dihydroxyethyl)-tetrahydrofuran-4-yl]validamine Validamine (2.0 g) and 1,2:5,6-di-O-isopropylidene-α-D-ribo-hexofuranose-3-urose (4.0 g) are dissolved in dimethylformamide (50 ml), and 2N hydrochloric acid (1.5 ml) and sodium cyanoborohydride (2.6 g) are added to the solution, followed by stirring at room temperature for 60 hours. The reaction mixture is concentrated under reduced pressure, and freed of the dimethylformamide azeotropically with toluene under reduced pressure. The residue is dissolved in water (200 ml), and Dowex 50W×8 (H+ type, produced by Dow Chemical Co., U.S.A.) (200 ml) is added to the solution, followed by stirring at room temperature for 1 hour. The mixture is poured onto a column with Dowex 50W×8 (H+ type, 100 ml), and the column is washed with water, followed by elution with 0.5N aqueous ammonia. The eluate is concentrated under reduced pressure, and the residue is chromatographed on a column of Amberlite CG-50 (NH4+ type, produced by Rohm & Haas Co., U.S.A.) (400 ml), followed by elution wiith water to give two fractional components.

The first fraction (210 to 285 ml) is concentrated under reduced pressure, and the residue is chromatographed on a column of Dowex 1×2 (OH− type, produced by Dow Chemical Co., U.S.A.) (450 ml), followed by elution with water. The eluate is concentrated under reduced pressure and lyophilized to produce white powdery N-[2,3-O-isopropylidene-2,3-dihydroxy-5-(1,2-dihydroxyethyl)-tetrahydrofuran-4-yl]validamine (850 mg).

The later fraction (290 to 440 ml) is concentrated under reduced pressure, and the residue is again chromatographed on a column of Amberlite CG-50 (NH4+ type, 400 ml), followed by elution with water. The eluate is concentrated under reduced pressure and lyophilized to produce white powdery N-(2,3,5-trihydroxy-6-hydroxymethyltetrahydropyran-4-yl)validamine (500 mg).

N-[2,3-O-isopropylidene-2,3-dihydroxy-5-(1,2-dihydroxyethyl)tetrahydrofuran-4-yl]validamine:
$[\alpha]_D^{23} +120.8°$ (c=1, $H_2O$).

Elemental analysis, for $C_{16}H_{29}NO_9\cdot\frac{1}{2}H_2O$: Calcd. (%): C, 49.47; H, 7.79; N, 3.61. Found (%): C, 49.52; H, 7.72; N, 3.71.

NMR ($D_2O$)δ: 1.2-2.35 (3H, m), 1.53 (3H, s), 1.70 (3H, s), 3.25-4.3 (11H, m), 5.06 (1H, t, J=4 Hz), 6.05 (1H, d, J=4 Hz).
TLC: Rf=0.55.

N-(2,3,5-trihydroxy-6-hydroxymethyltetrahydropyran-4-yl)validamine; $[\alpha]_D^{23} +32.1°$ (c=1, $H_2O$).

Elemental analysis, for $C_{13}H_{25}NO_9\cdot\frac{1}{2}H_2O$: Calcd. (%): C, 44.82; H, 7.52; N, 4.02. Found (%): C, 44.92; H, 7.89; N, 4.13.

$IC_{50}$ (maltase): $1.9\times10^{-6}$M.
$IC_{50}$ (saccharase): $1.7\times10^{-7}$M.
TLC: Rf=0.36.

EXAMPLE 11

N-(2,4-Diethoxycarbonylamino-5,6-dihydroxycyclohexyl)valiolamine

Valiolamine (2.0 g) and a mixture (4.0 g) of N,N'-diethoxycarbonyl-4,5-O-isopropylidene-6-oxo-2-deoxystreptamine and N,N'-diethoxycarbonyl-5,6-O-isopropylidene-4-oxo-2-deoxystreptamine as obtained in Reference Example 18 are dissolved in dimethylformamide (50 ml), and 2N hydrochloric acid (1.2 ml) and sodium cyanoborohydride (2.6 g) are added to the solution, followed by stirring at 60° to 70° C. for 15 hours. The reaction mixture is concentrated under reduced pressure, and freed of the dimethylformamide azeotropically with toluene under reduced pressure. The residue is dissolved in water (200 ml), and Dowex 50W×8 (H+ type, produced by Dow Chemical Co., U.S.A.) (200 ml) is added to the solution, followed by stirring at 60° C. for 1 hour. The mixture is poured onto a column packed with Dowex 50W×8 (H+ type, 50 ml), and the column is washed with water, followed by elution with 0.5N aqueous ammonia. The eluate is concentrated under reduced pressure, and the residue is chromatographed on a column of Amberlite CG-50 (NH4+ type, produced by Rohm & Haas Co., U.S.A.) (400 ml), followed by elution with water. The eluate is concentrated under reduced pressure and lyophilized to produce white powdery N-(2,4-diethoxycarbonylamino-5,6-dihydroxycyclohexyl)valiolamine (1.75 g).

$[\alpha]_D^{22} +14.7°$ (c=1, $H_2O$).
Elemental analysis, for $C_{19}H_{35}N_3O_{11}\cdot H_2O$: Calcd. (%): C, 45.68; H, 7.47; N, 8.41. Found (%): C, 45.59; H, 7.41; N, 8.29.

$IC_{50}$ (maltase): $9.0\times10^{-6}$M.
$IC_{50}$ (saccharase): $4.9\times10^{-6}$M.

EXAMPLE 12

N-(2,4-Diamino-5,6-dihydroxycyclohexyl)valiolamine

N-(2,4-Diethoxycarbonylamino-5,6-dihydroxycyclohexyl)valiolamine (1.5 g) is dissolved in water (50 ml), and barium hydroxide (6 g) is added to the solution, followed by stirring at 70° to 80° C. for 4 hours. After the reaction mixture is cooled to room temperature, carbon dioxide gas is introduced into it, and the resulting precipitates are filtered out and washed with water. The filtrate and washings are combined and chromatographed on a column of Amberlite CG-50 (NH4+ type, produced by Rohm & Haas Co., U.S.A.) (250 ml), and the column is washed with water, followed by elution with 0.5N aqueous ammonia. The eluate is concentrated under reduced pressure, and the residue is chromatographed on a column of Amberlite CG-50 (NH4+ type, 100 ml). The column is washed with water, and elution is performed with 0.1N aqueous ammonia to give three fractional components. The first fraction is concentrated under reduced pressure and lyophilized to produce white powder (43 mg) (referred to briefly as "isomer A"). The subsequently eluted fraction is concentrated under reduced pressure and lyophilized likewise to give white powder (100 mg) (referred to briefly as "isomer B"). The finally eluted fraction is concentrated under reduced pressure, and the residue is chromatographed on a column of Dowex 1×2 (OH− type, produced by Dow Chemical Co., U.S.A.) (180 ml), followed by elution with water. The eluate is concentrated under reduced pressure and lyophilized to produce white powder (40 mg) (referred to briefly as "isomer C"). Further, elution is effected with 0.5N hydrochloric acid, and the eluate is adjusted to pH 6 and chromatographed on a column of Amberlite CG-50 ($NH_4^+$ type, 100 ml). The column is washed with water, and elution is effected with 0.3N aqueous ammonia. The eluate is concentrated under reduced pressure and lyophilized to produce white powder (160 mg) (referred to briefly as "isomer D").

Isomer D: $[\alpha]_D^{22} + 26.6°$ (c=1, $H_2O$).

Elemental analysis, for $C_{13}H_{27}N_3O_7 \cdot 3/2H_2O$: Calcd. (%): C, 42.85; H, 8.30; N, 11.53. Found (%): C, 42.83; H, 8.48; N, 11.24.

$IC_{50}$ (maltase): $1.0 \times 10^{-6}$M.

$IC_{50}$ (saccharase): $8.8 \times 10^{-8}$M.

EXAMPLE 13

N-(2,4-Diethoxydiacarbonylamino-5,6-dihydroxycyclohexyl)validamine

Validamine (2.0 g) and a mixture (4.0 g) of N,N'-diethoxycarbonyl-4,5-O-isopropylidene-6-oxo-2-deoxystreptamine and N,N'-diethoxycarbonyl-5,6-O-isopropylidene-4-oxo-2-deoxystreptamine as obtained in Reference Example 18 are dissolved in dimethylformamide (50 ml), and 2N hydrochloric acid (1.5 ml) and sodium cyanoborohydride (2.6 g) are added to the solution, followed by stirring at 60° to 70° C. for 22 hours. The reaction mixture is concentrated under reduced pressure and further freed of the dimethylformamide azeotropically with toluene under reduced pressure. The residue is dissolved in water (200 ml), and Dowex 50W×8 ($H^+$ type, produced by Dow Chemical Co., U.S.A.) (200 ml) is added to the solution, followed by stirring at 60° C. for 1 hour. The mixture is poured onto a column packed with Dowex 50W×8 ($H^+$ type, 50 ml), and the column is washed with water, followed by elution with 0.5N aqueous ammonia. The eluate is concentrated under reduced pressure, and the residue is chromatographed on a column of Amberlite CG-50 ($NH_4^+$ type, produced by Rohm & Haas Co., U.S.A.) (400 ml), followed by elution with water. The eluate is concentrated under reduced pressure and lyophilized to produce white powdery N-(2,4-diethoxycarbonylamino-5,6-dihydroxycyclohexyl)validamine (1.1 g).

$[\alpha]_D^{23} + 39.9°$ (c=1, $H_2O$).

Elemental analysis, for $C_{19}H_{35}N_3O_{10} \cdot H_2O$: Calcd.(%): C, 47.19; H, 7.71; N, 8.69. Found (%): C, 46.64; H, 7.38; N, 8.60.

EXAMPLE 14

N-(2,4-Diamino-5,6-dihydroxycyclohexyl)validamine

N-(2,4-Diethoxycarbonylamino-5,6-dihydroxycyclohexyl)validamine (900 mg) is dissolved in water (35 ml), and barium hydroxide (4.0 g) is added to the solution, followed by stirring at 70° to 80° C. for 7.5 hours. The reaction mixture is cooled to room temperature, into which carbon dioxide gas is introduced, and the resulting precipitates are filtered out and washed with water. The filtrate and washings are combined and chromatographed on a column of Amberlite CG-50 ($NH_4^+$ type, produced by Rohm & Haas Co., U.S.A.) (150 ml), and the column is washed with water, followed by elution with 0.1N aqueous ammonia. The eluate is concentrated under reduced pressure and the residue is chromatographed on a column of Dowex 1×2 ($OH^-$ type produced by Dow Chemical Co., U.S.A.) (120 ml), and the column is washed with water, followed by elution with 0.5N hydrochloric acid. The eluate is adjusted to pH 6 and chromatographed on a column of Amberlite CG-50 ($NH_4^+$ type, 100 ml), and the column is washed with water, followed by elution with 0.3N aqueous ammonia. The eluate is concentrated under reduced pressure and lyophilized to produce white powdery N-(2,4-diamino-5,6-dihydroxycyclohexyl)validamine (100 mg).

$[\alpha]_D^{22} + 52.4°$ (c=0.5, $H_2O$).

Elemental analysis, for $C_{13}H_{27}N_3O_6 \cdot 2H_2O$: Calcd.(%): C, 43.68; H, 8.74; N, 11.76. Found (%): C, 43.58; H, 8.81; N, 11.90.

$IC_{50}$ (saccharase): $8.8 \times 10^{-7}$M.

EXAMPLE 15

To 200 ml of beverage admixed with fruit juice is added 100 mg of N-[(1R,2S)-(2,4/3,5)-trihydroxy-5-hydroxymethylcyclohexyl]validamine, and the mixture is stirred to make a uniform solution. In this manner, there is obtained beverage admixed with fruit juice containing an α-glucosidase inhibitor.

EXAMPLE 16

N-[(1R,2S)-(2,4/3,5)-2,3,4-trihydroxy-5-hydroxymethylcyclohexyl]valiolamine sulfate: 20 parts by weight Lactose: 80 parts by weight Crystalline cellulose: 20 parts by weight The above three ingredients are mixed, kneaded with water, dried and prepared in a powder or granular form to make powders.

EXAMPLE 17

N-[(1R,2S)-(2,4/3,5)-2,3,4-Trihydroxy-5-hydroxymethylcyclohexyl]validamine and
N-[(1S,2S)-(2,4/3,5)-2,3,4-trihydroxy-5-hydroxymethylcyclohexyl]validamine Validamine (1.0 g) and (2R)-(2,4/3,5)-2,3,4-trihydroxy-5-hydroxymethylcyclohexanone (1.0 g) are dissolved in dimethylformamide (25 ml), and after 2N hydrochloric acid (0.8 ml) and sodium cyanoborohydride (1.3 g) is added, the solution is stirred at room temperature for 19 hours. The reaction mixture is concentrated under reduced pressure and treated further with toluene, followed by distilling off the dimethylformamide azeotropically under reduced pressure. The residue is dissolved in water (100 ml), and after Dowex 50W×8 ($H^+$ type, produced by Dow Chemical Co., U.S.A., 100 ml) is added to the solution, the mixture is stirred at room temperature for 1 hour. The mixture is poured onto a column packed with Dowex 50W×8 ($H^+$ type, 50 ml), and the column is washed with water, followed by elution with 0.5N aqueous ammonia. The eluate is concentrated under reduced pressure, the residue is chromatographed on a column of Amberlite CG-50 ($NH_4^+$ type, produced by Rohm and Haas Co., U.S.A., 550 ml), followed by elution with water to give two fractions components. The first fraction (270 to 360 ml) is concentrated under reduced pressure and lyophilized to produce white powder (1.0 g) of the (1S,2S) isomer. The later fraction (430 to 580 ml) is concentrated under reduced pressure and lyophilized to produce white powder (320 mg) of the (1R,2S) isomer.

N-[(1S,2S)-(2,4/3,5)-2,3,4-trihydroxy-5-hydroxymethylcyclohexyl]validamine (the isomer obtained from the first eluted fraction): $[\alpha]_D^{25}+115.5°$ (c=1,H$_2$O).

Elemental analysis, for C$_{14}$H$_{27}$NO$_8$.H$_2$O: Calcd.(%): C, 47.31; H, 8.23; N, 3.94. Found (%): C, 47.32; H, 8.26; N, 4.06.

NMR (D$_2$O)δ: 1.2–1.75 (2H, m), 1.75–2.4 (4H, m), 3.2–4.15 (12H, m).

TLC: Rf=0.24.

N-[(1R,2S)-(2,4/3,5)-2,3,4-trihydroxy-5-hydroxymethylcyclohexyl]validamine (the isomer obtained from the later eluted fraction): $[\alpha]_D^{25}+35.5°$ (c=1, H$_2$O).

Elemental analysis, for C$_{14}$H$_{27}$NO$_8$.H$_2$O: Calcd.(%): C, 47.31; H, 8.23; N, 3.94. Found (%): C, 47.28; H, 8.01; N, 3.86.

NMR (D$_2$O)δ: 1.34 (1H, q, J=12 Hz), 1.5–2.5 (5H, m), 2.82 (1H, m), 3.25–4.15 (11H, m).

IC$_{50}$ (saccharase): 2.7×10$^{-7}$M.
IC$_{50}$ (maltase): 2.2×10$^{-6}$M.
TLC: Rf=0.25.

EXAMPLE 18

N-[(1R,2S)-(2,4/3,5)-2,3,4-Trihydroxy-5-hydroxymethylcyclohexyl]valiolamine and N-[(1S 2S)-(2,4/3,5)-2,3,4-trihydroxy-5-hydroxymethylcyclohexyl]valiolamine Valiolamine (2.1 g) and (2R)-(2,4/3,5)-2,3,4-trihydroxy-5-hydroxymethylcyclohexanone (1.9 g) are dissolved in dimethylformamide (50 ml), and after 2N-hydrochloric acid (1.5 ml) and sodium cyanoborohydride (2.6 g) are added, the solution is stirred at room temperature for 19 hours. The reaction mixture is concentrated under reduced pressure and treated further with toluene, followed by distilling off the dimethylformamide azeotropically under reduced pressure. The residue is dissolved in water (200 ml), and after Dowex 50W×8 (H$^+$ type, produced by Dow Chemical Co., U.S.A., 250 ml) is added, the mixture is stirred at room temperature for 1 hour. The mixture is poured onto a column packed with Dowex 50W×8 (H$^+$ type, 100 ml), and the column is washed with water, followed by elution with 0.5N aqueous ammonia. The eluate is concentrated under reduced pressure, and the residue is chromatographed on a column of Amberlite CG-50 (NH$_4^+$ type, produced by Rohm and Haas Co., U.S.A., 450 ml), followed by elution with water to give two fractional components. The first fraction (400 to 580 ml) is concentrated under reduced pressure, and the residue is chromatographed on a column of Dowex 1×2 (OH$^-$ type, produced by Dow Chemical Co., U.S.A., 270 ml), followed by elution with water. The eluate (200 to 550 ml) is concentrated under reduced pressure and lyophilized to produce white powder (1.53 g) of the (1S,2S) isomer. The later fraction (0.63 to 1.00 l) is concentrated under reduced pressure and lyophilized to produce white powder (570 mg) of the (1R,2S) isomer.

N-[(1S,2S)-(2,4/3,5)-2,3,4-trihydroxy-5-hydroxymethylcyclohexyl]valiolamine (the isomer obtained from the first fraction): $[\alpha]_D^{25}+48.5°$ (c=1, H$_2$O).

Elemental analysis, for C$_{14}$H$_{27}$NO$_9$.½H$_2$O: Calcd.(%): C, 46.40; H, 7.79; N, 3.87. Found (%): C, 46.29; H, 7.94; N, 3.73.

NMR (D$_2$O)δ: 1.43 (1H, dt, J=3.3 Hz, 13.5 Hz, 13.5 Hz), 1.67 (1H, dd, J=3.5 Hz, 15.5 Hz), 1.7–2.7 (2H, m), 2.32 (1H, dd, J=3 Hz, 15.5 Hz), 3.35–4.25 (12H, m).

IC$_{50}$ (saccharase): 5.6×10$^{-6}$M.
TLC: Rf=0.21.

N-[(1R,2S)-(2,4/3,5)-2,3,4-trihydroxy-5-hydroxymethylcyclohexyl]valiolamine (the isomer obtained from the later eluted fraction): $[\alpha]_D^{25}+5.2°$ (c=1,H$_2$O).

Elemental analysis, for C$_{14}$H$_{27}$NO$_9$.H$_2$O: Calcd.(%): C, 45.27; H, 7.87; N, 3.77. Found (%): C, 45.04; H, 7.97; N, 3.59.

NMR (D$_2$O)δ: 1.1–2.55 (5H, m), 2.65–3.3 (1H, m), 3.4–4.45 (11H, m).

IC$_{50}$ (maltase): 4.4×10$^{-8}$M.
IC$_{50}$ (saccharase): 4.8×10$^{-8}$M.
TLC: Rf=0.23.

EXAMPLE 19

N-[(1R,2S)-(2,4/3,5)-2,3,4-Trihydroxy-5-hydroxymethylcyclohexyl]valiolamine sulfate N-[(1R,2S)-(2,4/3,5)-2,3,4-Trihydroxy-5-hydroxymethylcyclohexyl]valiolamine (500 mg) is dissolved in water (20 ml), and the solution is adjusted to pH 3 by adding dropwise 1N sulfuric acid and then concentrated to about 5 ml under reduced pressure. The concentrate is chromatographed on a column (100 ml) of activated carbon, and elution is performed with water. The eluate is concentrated under reduced pressure and lyophilized to produce N-[(1R,2S)-(2,4/3,5)-2,3,4-trihydroxy-5-hydroxymethylcyclohexyl]valiolamine sulfate.

EXAMPLE 20

N-[(1R,2S)-(2,6/3,4)-4-Amino-2,3-dihydroxy-6-methylcyclohexyl]valiolamine and
N-[(1S,2S)-(2,6/3,4)-4-amino-2,3-dihydroxy-6-methylcyclohexyl]valiolamine Valiolamine (4.0 g) and (2R)-(2,6/3,4)-2,3-O-cyclohexylidene-4-benzyloxycarbonylamino-2,3-dihydroxy-6-methylcyclohexanone (9.2 g) are dissolved in dimethylformamide (120 ml), and 2N hydrochloric acid (3 ml) and sodium cyanoborohydride (5.6 g) are added to the solution, followed by stirring at 50° to 60° C. for 18 hours. The reaction mixture is concentrated under reduced pressure, and toluene is further added to the residue. The mixture is freed of dimethylformamide azeotropically, and the resultant residue is added to a mixture of ethyl acetate and water to allow the distribution between them. The ethyl acetate layer is separated, washed with water, dried over anhydrous sodium sulfate and freed of the solvent under reduced pressure. Ethyl ether (500 ml) is added to the residue, which is left on standing overnight in a refrigerator. The resultant precipitates are recovered by filtration, washed with ethyl ether and dried in a desiccator under reduced pressure. The powder (3.0 g) thus obtained is dissolved in 80% aqueous acetic acid (100 ml), and the solution is stirred at 50° to 60° C. for 1 hour. The reaction mixture is concentrated under reduced pressure, and the residue is added to a mixture of ethyl acetate and water to allow the distribution between them. The water layer is separated, washed with ethyl acetate and freed of the solvent under reduced pressure. The residue is dissolved in water-methanol-acetic acid (50:30:2, 100 ml), and palladium black (600 mg) is added to the solution, which is stirred in the stream of hydrogen at room temperature for 8 hours. The catalyst is filtered out and washed with water, and the filtrate and washings are combined and concentrated under reduced pressure. The residue is chromatographed on a column of Amberlite CG-50 (NH$_4^+$ type, 250 ml) (produced by Rohm & Haas Co., U.S.A.), and the column is washed with water, followed by elution with 0.1N aqueous ammonia to per-form the elution into two fractional components, the first fraction (0.8 to 1.0 l) and the later eluted fraction (1.3 to 1.7 l). The first fraction is concentrated under reduced pressure, and the residue is chromatographed again on a column of Amberlite CG-50 ($NH_4^+$ type, 400 ml), followed by elution with 0.1N aqueous ammonia. The eluate is concentrated under reduced pressure and lyophilized to produce N-[(1R,2S)-(2,6/3,4)-4-amino-2,3-dihydroxy-6-methylcyclohexyl]valiolamine (505 mg) as white powder. The later eluted fraction is concentrated under reduced pressure, and the resultant residue is chromatographed on a column of Dowex 1×2 ($OH^-$ type, 150 ml) (produced by Dow Chemical Co., U.S.A.), followed by elution with water. The eluate is concentrated under reduced pressure and lyophilized to produce N-[(1S, 2S)-(2,6/3,4)-4-amino-2,3-dihydroxy-6-methylcyclohexyl]valiolamine (490 mg).

N-[(1R,2S)-(2,6/3,4)-4-amino-2,3-dihydroxy-6-methylcyclohexyl]valiolamine (the first eluted isomer, referred to briefly as "isomer (a)").

Elemental analysis, for $C_{14}H_{28}N_2O_7 \cdot H_2O$: Calcd.(%): C, 47.45; H, 8.53; N, 7.90. Found (%): C, 47.59; H, 8.30; N, 8.03.

$[\alpha]_D^{26} + 42.6°$ (c=1, $H_2O$).

NMR ($D_2O$)δ: 1.25 (3H, d, J=6 Hz), 1.4–2.7 (6H, m), 3.4–4.2 (9H, m).

$IC_{50}$ (maltase): $2.8 \times 10^{-8}$M.

$IC_{50}$ (saccharase): $7.5 \times 10^{-9}$M.

N-[(1S,2S)-(2,6/3,4)-4-amino-2,3-dihydroxy-6-methylcyclohexyl]valiolamine (the later eluted isomer, referred to briefly as "isomer (b)").

Elemental analysis, for $C_{14}H_{28}N_2O_7 \cdot H_2O$: Calcd.(%): C, 47.45; H, 8.53; N, 7.90. Found (%): C, 47.50; H, 8.87; N, 7.98.

$[\alpha]_D^{26} + 2.0°$ (c=1, $H_2O$).

NMR ($D_2O$)δ: 1.24 (3H, d, J=6.5 Hz), 1.5–2.7 (5H, m), 3.1–3.3 (1H, m), 3.3–4.3 (9H, m).

$IC_{50}$ (maltase): $1.5 \times 10^{-6}$M.

$IC_{50}$ (saccharase): $5.3 \times 10^{-8}$M.

EXAMPLE 21

N-[(1R,2S)-(2,6/3,4)-2,3,4-Trihydroxy-6-methylcyclohexyl]valiolamine and
N-[(1R,2S)-(2,4,6/3)-2,3,4-trihydroxy-6-methylcyclohexyl]valiolamine N-[(1R,2S)-(2,6/3,4)-4-Amino-2,3-dihydroxy-6-methylcyclohexyl]valiolamine (200 mg) is dissolved in methanol (5 ml), and 3,5-di-tert-butyl-1,2-benzoquinone (180 mg) is added to the solution, followed by stirring at room temperature for 15 hours. The reaction mixture is adjusted to pH 1 to 2 with 1N sulfuric acid and stirred at room temperature for 3 hours, followed by addition of water (100 ml) and chloroform (50 ml). The water layer is separated, washed with chloroform and concentrated under reduced pressure to about 50 ml. Sodium borohydride (200 mg) is added to the concentrate under cooling in ice-water bath, and the mixture is stirred at the same temperature for 2 hours and then at room temperature for 1 hour. The reaction mixture is adjusted to pH 5 with acetic acid and chromatographed on a column of Dowex 50W×8 ($H^+$ type, 160 ml) (produced by Dow Chemical Co., U.S.A.), and the column is washed with water, followed by elution with 0.5N aqueous ammonia. The eluate is concentrated under reduced pressure, and the residue is chromatographed on a column of Amberlite CG-50 ($NH_4^+$ type, 180 ml) (produced by Rohm & Haas Co., U.S.A.), followed by elution with water to give two fractional components, the first fraction (320 to 480 ml); and the later eluted fraction (510 to 900 ml). Each eluate is concentrated under reduced pressure and lyophilized to give white powder (57 mg) showing $[\alpha]_D^{26} + 18.9°$ (c=1, $H_2O$) from the first eluted fraction and white powder (31 mg) showing $[\alpha]_D^{26} + 31.1°$ (c=1, $H_2O$) from the later eluted fractions, respectively.

The first eluted isomer (referred to briefly as "isomer (a)").

Elemental analysis, for $C_{14}H_{27}NO_8 \cdot \frac{1}{2}H_2O$: Calcd.(%): C, 48.55; H, 8.15; N, 4.04. Found (%): C, 48.45; H, 8.69; N, 3.92.

NMR ($D_2O$): 1.28 (3H, d, J=6 Hz), 1.3–2.4 (5H, m), 2.50 (1H, t, J=10 Hz), 3.3–4.2 (9H, m).

TLC Rf=0.29.

$IC_{50}$ (maltase): $7.0 \times 10^{-8}$M.

$IC_{50}$ (saccharase): $3.5 \times 10^{-8}$M.

The later eluted isomer (referred to briefly as "isomer (b)").

Elemental analysis, for $C_{14}H_{27}NO_8 \cdot \frac{1}{2}H_2O$: Calcd.(%): C, 48.55; H, 8.15; N, 4.04. Found (%): C, 48.23; H, 8.45; N, 3.92.

NMR ($D_2O$)δ: 1.26 (3H, d, J=6 Hz), 1.5–2.4 (5H, m), 2.45 (1H, t, J=10 Hz), 3.5–4.35 (9H, m).

TLC Rf=0.30.

$IC_{50}$ (maltase): $6.8 \times 10^{-8}$M.

$IC_{50}$ (saccharase): $3.6 \times 10^{-8}$M.

EXAMPLE 22

N-[(1S,2S)-(2,6/3)-2,3,4-Trihydroxy-6-methylcyclohexyl]valiolamine

N-[(1S,2S)-(2,6/3,4)-4-Amino-2,3-dihydroxy-6-methylcyclohexyl]valiolamine (300 mg) is dissolved in methanol (5 ml), and 3,5-di-tert-butyl-1,2-benzoquinone (300 mg) is added to the solution, followed by stirring at room temperature for 18 hours. The reaction mixture is adjusted to pH 1 to 2 with 1N sulfuric acid, and stirred at room temperature for 3 hours. Water (100 ml) and chloroform (100 ml) are added to the reaction mixture, and the water layer is separated, washed with chloroform and concentrated under reduced pressure to about 50 ml. Sodium borohydride (400 mg) is added to the concentrate under cooling in ice-water bath, and the mixture is stirred at the same temperature for 2 hours and then at room temperature for 2 hours. The reaction mixture is adjusted to pH 4.5 with acetic acid and chromatographed on a column of Dowex 50W×8 ($H^+$ type, 150 ml) (produced by Dow Chemical Co., U.S.A.). The column is washed with water, and elution is performed with 0.5N aqueous ammonia. The eluate is concentrated under reduced pressure, and the residue is chromatographed on a column of Amberlite CG-50 ($NH_4^+$ type, 150 ml) (produced by Rohm & Haas Co., U.S.A.). The column is washed with water, and elution is performed with 0.1N aqueous ammonia. The eluate is concentrated under reduced pressure, and the residue is chromatographed on a column of Amberlite CG-50 ($NH_4^+$ type, 75 ml), followed by elution with 0.025N aqueous ammonia. The eluate (150 to 270 ml) is concentrated under reduced pressure and lyophilized to produce white powdery N-[(1S,2S)-(2,6/3)-2,3,4-trihydroxy-6-methylcyclohexyl]valiolamine (30 mg) (provided, however, that the configuration of the hydroxyl group at the 4-position in the 2,3,4-trihydroxy-6-methylcyclohexyl moiety is not determined).

Elemental analysis, for $C_{14}H_{27}NO_8 \cdot \frac{1}{2}H_2O$: Calcd.(%): C, 48.55; H, 8.15; N, 4.04. Found (%): C, 48,16; H, 8.34; N, 3.95.

$[\alpha]_D^{26} + 25.9°$ (c=1, $H_2O$).

NMR ($D_2O$)δ: 1.28 (3H, d, J=6.5 Hz), 1.5-2.25 (4H, m), 2.43 (1H, dd, J=3 Hz, 15 Hz), 3.13 (1H, t, J=3.5 Hz), 3.37 (1H, q, J=3.5 Hz), 3.5-4.25 (8H, m).

TLC: Rf=0.28.

EXAMPLE 23

To 200 ml of beverage containing 10% of orange juice is added 10 mg of the isomer (a) of Example 20, and the mixture is stirred to a uniform solution. In this manner, there is obtained beverage admixed with fruit juice containing an α-glucosidase inhibitor.

EXAMPLE 24

The isomer (a) of Example 21: 20 parts by weight
Lactose: 80 parts by weight
Crystalline cellulose: 20 parts by weight The above three ingredients are mixed uniformly, kneaded with water, dried and prepared in a powder or granular form to make powders according to the procedure per se known.

EXAMPLE 25

1,6-Anhydro-4-O-α-[4-[(1S)-(1,2,4,5(OH)/3,5(CH$_2$O-H))-(2,3,4,5-tetrahydroxy-5-(hydroxymethyl)cyclohexyl)amino-4,6-dideoxy-D-glucopyranosyl]-β-D-glucose and 1,6-Anhydro-4-O-α-[4-[(1S)-(1,2,4,5(OH)/3,5(CH$_2$OH)-(2,3,4,5-tetrahydroxy-5-(hydroxymethyl)cyclohexyl)amino]-4,6-dideoxy-D-galactopyranosyl]-β-D-glucopyranose 2,3-Di-O-benzyl-1,6-anhydro-4-O-(2,3-di-O-benzyl-6-deoxy-α-D-xylo-4-hexopyranoseurosyl)-β-D-glucopyranose (40.5 g) and valiolamine (12.0 g) are dissolved in dimethylformamide (300 ml). To the solution are added 2N hydrochloric acid (9 ml) and sodium cyanoborohydride (15.6 g), followed by stirring at 60° to 65° C. for 13 hours. The reaction mixture is concentrated under reduced pressure, and further freed of the dimethylformamide azeotropically with toluene. After the residue is added to a mixture of water (300 ml) and ethyl acetate (300 ml) to allow the distribution, the ethyl acetate layer is separated, and the water layer is extracted twice with ethyl acetate (200 ml). The ethyl acetate extracts are combined, washed with water, dried over sodium sulfate and concentrated under reduced pressure, followed by addition of ethyl ether (1 l) to give a syrupy material. The syrupy material is chromatographed on a column of silica gel (550 ml), and the column is washed with chloroform, followed by elution with chloroform-methanol (9:1). The eluate is concentrated under reduced pressure, and the residue is further dried in a desiccator under reduced pressure. The resultant white powder (5.8 g) is suspended in liquid ammonia (about 200 ml) in a dry ice-acetone bath, and sodium is added to the suspension until the blue color of the solution does not disappear, followed by stirring at the same temperature for further 1 hour. Ethanol (30 ml) and sodium (1.0 g) are added to the reaction mixture, which is stirred at the same temperature for 2 hours. Ammonium acetate is added to the reaction mixture until the blue color of the reaction mixture disappears, and after the cooling bath is removed, the reaction mixture is freed of the ammonia while stirring and concentrated under reduced pressure. A mixture of ethyl acetate (350 ml) and water (350 ml) is added to the residue to allow the distribution, and the water layer is separated, adjusted to pH 7 with 2N hydrochloric acid and admixed with Dowex 50W×8 ($H^+$ type, 350 ml), followed by stirring at room temperature for 1 hour. The Dowex 50W×8 is added onto a column packed with another Dowex 50W×8 ($H^+$ type, 100 ml), and the column is washed with water (3 l), followed by elution with 0.5N aqueous ammonia. The eluate (1.3 to 2.4 l) is concentrated under reduced pressure, and the residue is chromatographed on a column of Amberlite CG-50 ($NH_4^+$ type, 450 ml), followed by elution with water. The eluate (235 to 350 ml) is concentrated under reduced pressure, and the residue is chromatographed on a column of Dowex 1×2 ($OH^-$ type, 270 ml), followed by elution with water to allow the separation into the first eluted fraction (310 to 665 ml) and later eluted fraction (680 to 1640 ml). The eluates are each concentrated under reduced pressure, and the concentrates are chromatographed again on a column of Dowex 1×2 ($OH^-$ type, 160 ml), respectively, followed by elution with water Concentration of the eluates under reduced pressure followed by lyophilization yields white powdery 1,6-anhydro-4-O-α-[4-(1S)-(1,2,4,5(OH)/3,5(C-H$_2$OH)-(2,3,4,5-tetrahydroxy-5-(hydroxymethyl)cyclohexyl)amino]-4,6-dioxy-D-galactopyranosyl]-β-D-glucopyranose (520 mg) from the first eluted fraction and white powdery 1,6-anhydro-4-O-α-[4-O-α-[4-[(1S)-(1,2,4,5(OH)/3,5(CH$_2$OH)-(2,3,4,5-tetrahydroxy-5-(hydroxymethyl)cyclohexyl)amino]-4,6-dideoxy-D-glucopyranosyl]-β-D-glucopyranose (1.25 g) from the later eluted fraction.

Compound obtained from the first eluted fraction [isomer (a)]: $[\alpha_D^{25} + 86.5°$ (c=1, $H_2O$).

Elemental analysis, for $C_{19}H_{33}NO_{13} \cdot H_2O$: Calcd.(%): C, 45.51; H, 7.03; N, 2.79. Found (%): C, 45.22; H, 7.00; N, 2.79.

NMR ($D_2O$)δ: 1.53 (3H, d, J=6.5 Hz, 6'—$CH_3$), 1.71 (1H, dd, J=3 Hz, 15.5 Hz, 6—$\overline{CH}$), 2.33 (1H, $\overline{dd}$, J=3 Hz, 15.5 Hz, 6—$\overline{CH}$), 3.22 (1H, $\overline{dd}$, J=~1 Hz, 3 Hz, 4'—$\overline{CH}$), 3.45-4.65 (15H, m), 5.32 (1H, d, J=4.5 Hz, 1'—$\overline{CH}$), 5.70 (1H, s, 1"—$\overline{CH}$).

TLC: Rf=0.24.

Compound obtained from the later eluted fraction [isomer (b)]: $[\alpha]_D^{26} + 65.2°$ (c=1, $H_2O$).

Elemental analysis, for $C_{19}H_{33}NO_{13} \cdot H_2O$: Calcd.(%): C, 45.51; H, 7.03; N, 2.79. Found (%): C, 45.48; H, 7.07; N, 2.86.

NMR ($D_2O$)δ: 1.54 (3H, d, J=6.5 Hz, 6'—$CH_3$), 1.78 (1H, dd, J=3 Hz, 15.5 Hz, 6—$\overline{CH}$), 2.30 (1H, $\overline{dd}$, J=3 Hz, 15.5 Hz, 6—$\overline{CH}$), 2.71 (1H, $\overline{t}$, J=10 Hz, 4'—$\overline{CH}$), 3.5-4.6 (15H, m), 5.28 (1H, d, J=3.8 Hz, 1'—$\overline{CH}$), 5.69 (1H, s, 1"—$\overline{CH}$).

TLC: Rf=0.33.

IC$_{50}$ (saccharase): $2.5 \times 10^{-8}$M.

IC$_{50}$ (maltase): $1.3 \times 10^{-7}$M.

EXAMPLE 26

Octa-O-acetyl-[1,6-anhydro-4-O-α-[4-[(1S)-(1,2,4,5(OH)/3,5(CH$_2$OH))-(2,3,4,5-tetrahydroxy-5-(hydroxymethyl)cyclohexyl)amino]-4,6-dideoxy-D-glucopyranosyl]-β-D-glucopyranose]

1,6-Anhydro-4-O-α-[4-[(1S)-(1,2,4,5(OH)/3,5(CH$_2$OH)(2,3,4,5-tetrahydroxy-5-(hydroxymethyl)cyclohexyl)amino]-4,6-dideoxy-D-glucopyranosyl]-β-D-glucopyranose (1.0 g) is dissolved in pyridine (25 ml), and acetic anhydride (12.5 ml) is added to the solution, followed by stirring at room temperature for 15 hours. The reaction mixture is concentrated to dryness under reduced pressure, followed by drying overnight in a desiccator under reduced pressure, and to the resultant residue is added ethyl ether-petroleum ether (1:10, about 100 ml). The mixture is allowed to stand overnight in a refrigerator to give white crystalline powder (1.67 g) of the subject octa-O-acetyl-1,6-anhydro derivative.

$[\alpha]_D^{25} +22.3°$ (c=1, $CH_3OH$).

Elemental analysis, for $C_{35}H_{49}NO_{21}$: Calcd.(%): C, 51.28; H, 6.02; N, 1.71. Found (%): C, 51.37; H, 6.20; N, 1.68.

NMR ($CDCl_3$): 1.35 (3H, d, J=6 Hz, 6'—C$\underline{H}$), 1.5-2.4 (2H, m, 6—C$\underline{H}_2$), 1.97-2.28 (24H, C$\underline{H}_3$—COO—x8), 2.5-2.73 (1$\underline{H}$, m, 4'—C$\underline{H}$, which, in the case of addition of $D_2O$, changes to t, $\overline{J}$=10 Hz), 3.33-3.47 (1H, m, 1—C$\underline{H}$), 3.63-4.2 (6H, m), 4.5-5.7 (12H, m).

EXAMPLE 27

Deca-O-acetyl-[4-O-α-[4-[(1S)-1,2,4,5(OH)/3,5(CH$_2$OH)-(2,3,4,5-tetrahydroxy-5-(hydroxymethyl)cyclohexyl)amino]-4,6-dideoxy-D-glucopyranosyl]-D-glucopyranose]

Octa-O-acetyl-[1,6-anhydro-4-O-α-[4-((1S)-(1,2,4,5(OH)/3,5(CH$_2$OH))-(2,3,4,5-tetrahydroxy-5-(hydroxymethyl)cyclohexyl)amino]-4,6-dideoxy-D-glucopyranosyl]-β-D-glucopyranose] (1.57 g) is dissolved in a mixture of acetic acid (40 ml), acetic anhydride (40 ml) and sulfuric acid (1 ml), and the solution is stirred at room temperature for 2 hours. The reaction mixture is poured into ice-water (1 l), and sodium hydrogen carbonate (10 g) is added to the mixture while stirring under ice-cooling, followed by stirring at the same temperature for 2 hours. The reaction mixture is extracted with chloroform, and the chloroform extract is washed with saturated aqueous sodium hydrogen carbonate and water successively, dried over sodium sulfate and concentrated under reduced pressure. The residue is chromatographed on a column of silica gel (250 ml), and elution is performed with chloroform-methanol (30:1). The eluate (340 to 640 g) is concentrated to dryness under reduced pressure to give white powdery deca-O-acetyl-[4-O-α-[4-(1S)-(1,2,4,5(OH)/3,5(CH$_2$OH))-(2,3,4,5-tetrahydroxy-5-(hydroxymethyl)cyclohexyl)amino]-4,6-dideoxy-D-glucopyranosyl]-D-glucopyranose] (1.58 g).

$[\alpha]_D^{25} +70.4°$ (c=1, $CH_3OH$).

Elemental analysis, for $C_{39}H_{55}NO_{24}$: Calcd.(%): C, 50.81; H, 6.01; N, 1.52. Found (%): C, 50.78; H, 5.62; N, 1.58.

EXAMPLE 28

4-O-α-[4-[(1S)-(1,2,4,5(OH)/3,5(CH$_2$OH))-(2,3,4,5-Tetrahydroxy-5-(hydroxymethyl)cyclohexyl)amino]-4,6-dideoxy-D-glucopyranosyl]-D-glucopyranose Deca-O-acetyl-[4-O-α-[4-(1S)-(1,2,4,5(OH)/3,5(CH$_2$OH))-(2,3,4,5-tetrahydroxy-5-(hydroxymethyl)cyclohexyl)amino]-4,6-dideoxy-D-glucopyranosyl]-D-glucopyranose] (985 mg) is dissolved in methanol (50 ml), and 28% aqueous ammonia (10 ml) is added to the solution, followed by stirring at room temperature for 20 hours. The reaction mixture is concentrated to dryness under reduced pressure, and the residue is chromatographed on a column of Dowex 50W×8 (H$^+$ type, 50 ml). After the column is washed with water, elution is performed with 0.5N aqueous ammonia. The eluate (155 to 485 ml) is concentrated under reduced pressure, and the concentrate is chromatographed on a column of Amberlite CG-50 (NH$_4^+$ type, 360 ml), followed by elution with water. The eluate (215 to 290 ml) is concentrated under reduced pressure and lyophilized to give 4-O-α-[4-[(1S)-(1,2,4,5(OH)/3,5(CH$_2$OH))-(2,3,4,5-tetrahydroxy-5-(hydroxymethyl)cyclohexyl)amino]-4,6-dideoxy-D-glucopyranosyl]-D-glucopyranose (400 mg).

$[\alpha]_D^{25} +97.7°$ c=1, $H_2O$).

Elemental analysis, for $C_{19}H_{35}NO_{14}.2H_2O$: Calcd.(%): C, 42.46; H, 7.31; N, 2.61. Found (%): C, 42.65; H, 7.23; N, 2,87.

NMR ($D_2O$)δ: 1.54 (3H, d, J=6 Hz, 6'—CH$_3$), 1.78 (1H, dd, J=3.5 Hz, 15 Hz, 6—C$\underline{H}$), 2.28 (1H, $\overline{dd}$, J=3 Hz, 15 Hz, 6—C$\underline{H}$), 2.70 (1H, t, $\overline{J}$=9.5 Hz, 4'—C$\underline{H}$), 3.3-4.5 (15H, m), ~4.85(1"—CHβ, which overlaps with HOD), 5.45 (d, J=3.5 Hz, 1"—C$\underline{H}$α), 5.52 (1H, d, J=3.5 Hz, 1'—C$\underline{H}$).

TLC: Rf=0.27.

IC$_{50}$ (saccharase): 8.0×10$^{-8}$M.

IC$_{50}$ (maltase): 1.2×10$^{-7}$M.

EXAMPLE 29

Octa-O-acetyl-[1,6-anhydro-4-O-α-[4-[(1S)-(1,2,4,5(OH)/3,5(CH$_2$OH)-(2,3,4,5-tetrahydroxy-5-(hydroxymethyl)cyclohexyl)amino]-4,6-dideoxy-D-galactopyranosyl]-β-D-glucopyranose]

1,6-Anhydro-4-O-α-[4-[(1S)-(1,2,4,5(OH)/3,5(CH$_2$OH)-(2,3,4,5-tetrahydroxy-5-(hydroxymethyl)cyclohexyl)amino]-4,6-dideoxy-D-galactopyranosyl]-β-D-glucopyranose (320 mg) is dissolved in pyridine (10 ml), to which is added acetic anhydride (5 ml), followed by stirring at room temperature for 15 hours. The reaction mixture is concentrated to dryness under reduced pressure, followed by drying further overnight in a desiccator under reduced pressure, and the residue is added ethyl ether-petroleum ether (1:10, about 50 ml). The mixture is allowed to stand overnight in a refrigerator to give white powder (430 mg) of the subject octa-O-acetyl-1,6-anhydro derivative.

$[\alpha]_D^{25} +62.0°$ (c=0.5, $CH_3OH$).

Elemental analysis, for $C_{35}H_{49}NO_{21}$: Calcd.(%): C, 51.28; H, 6.02; N, 1.71. Found (%): C, 51.22; H, 5.88; N, 1.69.

NMR ($CDCl_3$)δ: 1.12 (3H, d, J=6.5 Hz, 6'—CH$_3$), 1.45-2.2 (2H, m, 6-CH$_2$), 1.98-2.17 (24H, CH$_3$COO- x 8), 3.06-3.27 (1H, m, $\overline{4'}$-C$\underline{H}$, which in the case of addition of D$_2$O, changes to dd, J=~1 Hz, 4.5 Hz), 3.33-4.17 (7H, m), 4.3-5.5 (11H, m), 5.69 (1H, t, J=10 Hz, 3-C$\underline{H}$).

EXAMPLE 30

Deca-O-acetyl-[4-O-α-[4-[(1S)-(1,2,4,5(OH)/3,5(CH$_2$OH))-(2,3,4,5-tetrahydroxy-5-(hydroxymethyl)cyclohexyl)amino]-4,6-dideoxy-D-galactopyranosyl]-D-glucopyranose]

Octa-O-acetyl-[1,6-anhydro-4-O-α-[4-[(1S)-(1,2,4,5(OH)/3,5(CH$_2$OH))-(2,3,4,5-tetrahydroxy-5-(hydroxymethyl)cyclohexyl)amino]--dideoxy-D-galactopyranosyl]-β-D-glucopyranose] (450 mg) is dissolved in a mixture of acetic acid (10 ml), acetic anhydride (10 ml) and sulfuric acid (0.25 ml), and the solution is stirred at room temperature for 2 hours. The reaction mixture is poured into ice-water (250 ml), and sodium hydrogen carbonate (2.5 g) is added to the mixture with stirring under ice-cooling, followed by stirring further at the same temperature for 2 hours. The reaction mixture is extracted with chloroform, and the chloroform extract is washed with saturated aqueous sodium hydrogen carbonate and water successively, dried over anhydrous sodium sulfate, and concentrated under reduced pressure. The residue is chromatographed on a column of silica gel (150 ml), and elution is performed with chloroform-methanol (30:1). The eluate (200 to 480 g) is concentrated to dryness under reduced pressure to give white powdery deca-O-acetyl-[4-O-α-[4-[(1S)-(1,2,4,5(OH)/3,5(CH₂OH)-(2,3,4,5-tetrahydroxy-5-(hydroxymethyl)cyclohexyl)amino]-4,6-dideoxy-D-galactopyranosyl]-D-glucopyranose] (550 mg).

$[\alpha]_D^{25} + 98.9°$ (c=1, CH₃OH).

Elemental analysis, for C₃₉H₅₅NO₂₄: Calcd.(%): C, 50.81; H 6.01; N, 1.52. Found (%): C, 50.55; H, 5.88; N, 1.56.

EXAMPLE 31

4-O-α-8
4-[(1S)-(1,2,4,5(OH)/3,5(CH₂OH)-(2,3,4,5-Tetrahydroxy-5-(hydroxymethyl)cyclohexyl)amino]-4,6-dideoxy-D-galactopyranosyl]-D-glucopyranose Deca-O-acetyl[4-O-α-[4-[(1S)-(1,2,4,5(OH)/3,5(CH₂OH))-(2,3,4,5-tetrahydroxy-5-(hydroxymethyl)cyclohexyl)amino]-4,6-dideoxy-D-galactopyranosyl]-D-glucopyranose] (450 mg) is dissolved in methanol (25 ml), to which is added 28% aqueous ammonia (5 ml), followed by stirring at room temperature for 15 hours. The reaction mixture is concentrated to dryness under reduced pressure, and the residue is chromatographed on a column of Dowex 50W×8 (H⁺ type, 25 ml). The column is washed with water, and elution is performed with 0.5N aqueous ammonia. The eluate (97 to 255 ml) is concentrated under reduced pressure, and the concentrate is chromatographed on a column of Amberlite CG-50 (NH₄⁺ type, 180 ml), followed by elution with water. The eluate (120 to 150 ml) is concentrated under reduced pressure and lyophilized to produce 4-O-α-[4-[(1S)-(1,2,4,5(OH)/3,5(CH₂OH)-(2,3,4,5-tetrahydroxy-5-hydroxymethyl)cyclohexyl)amino]-4,6-dideoxy-D-galactopyranosyl]-D-glucopyranose (170 mg).

$[\alpha]_D^{25} + 119.6°$ (c=1, H₂O).

Elemental analysis, for C₁₉H₃₅NO₁₄·2H₂O: Calcd.(%): C, 42.46; H, 7.31; N, 2.61. Found (%): C, 42.54; H, 7.20; N, 2.89.

NMR (D₂O)δ: 1.54 (3H, d, J=6.5 Hz, 6'-CH₃), 1.71 (1H, dd, J=3.5 Hz, 15 Hz, 6-CH), 2.33 (1H, dd, J=3 Hz, 15 Hz, 6-CH), 3.22 (1H, dd, J=~1 Hz, 4 Hz, 4'-CH), 3.33–4.67 (15H, m), ~4.85 (1''-CHβ, which overlaps with HOD), 5.47 (d, J=3.5 Hz, 1''-CHα), 5.55 (1H, d, J=3.5 Hz, 1'-CH).

TLC: Rf=0.23.

EXAMPLE 32

To 200 ml of beverage admixed with 20% of orange juice is added 10 mg of the isomer (b) in Example 25, followed by stirring to make a uniform solution. Thus the beverage admixed with fruit juice containing α-glucosidase inhibitor is obtained.

EXAMPLE 33

4-O-α-[4-[(1S)-(1,2,4,5(OH)/3,5(CH₂OH)-(2,3,4,5-tetrahydroxy-5-(hydroxymethyl)cyclohexyl)amino]-4,6-dideoxy-D-glucopyranosyl]-D-glucopyranose: 20 parts by weight Lactose: 80 parts by weight
Crystalline cellulose: 20 parts by weight The above ingredients are uniformly mixed, kneaded with water, and dried. By a conventional method, the mixture is processed into powder or granule form to make a powder preparation.

What is claimed is:

1. A compound of the general formula:

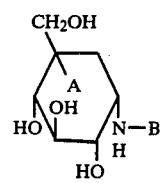

wherein
A is hydrogen or a hydroxyl group;
B is (1) a group of the formula:

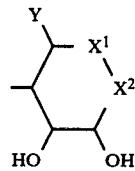

wherein
X¹ and X² both are represented by

or wherein one of X¹ and X² is oxygen while the other is

or wherein X¹ and X² combine to form —O—; Y is ① a C¹⁻⁴-alkyl or C¹⁻⁴ hydroxyalkyl group, ② a hydroxyl group, or ③ an amino group; and Z is hydrogen, a hydroxyl group, a hydroxymethyl group or an amino group; or B is (2) a group of the formula:

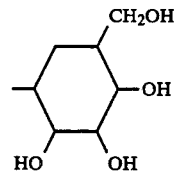

or B is (3) a group of the formula:

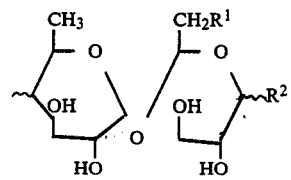

wherein
R¹ and R² are each a hydroxyl group or combine to form —O—; the chemical bond designates the R- or S-configuration; wherein the amino group is unsubstituted or protected
by a C¹⁻⁵-alkanoyl group which is unsubstituted or substituted by halogen,
or by a benzoyl, chlorobenzoyl, nitrobenzoyl, methoxybenzoyl, phthaloyl group or
by a C²⁻⁶-alkoxycarbonyl group or
by a benzyloxycarbonyl group which is unsubstituted or substituted by nitro, methoxy or halo, or
by a nitro-substituted phenyl group:
and wherein the hydroxyl groups are unsubstituted or protected
by a C¹⁻⁵-alkanoyl group which is unsubstituted or substituted by halogen, or
by a C¹⁻⁴-alkoxy, phenoxyl or halophenoxyl group or
by a benzoyl group which is unsubstituted or substituted by nitro or phenyl or
by a C²⁻⁶-alkoxycarbonyl group which is unsubstituted or substituted by halogen, or
by a C³⁻⁵-alkenyloxycarbonyl group, or
by a benzyloxycarbonyl group which is unsubstituted or substituted by nitro or C¹⁻⁴ alkoxy, or
by a nitro substituted phenoxycarbonyl group, or
by a C¹⁻⁵ alkyl group which is unsubstituted or substituted by halogen, C¹⁻⁴-alkoxy, benzyloxy or phenyl, or
by a C²⁻⁴-alkenyl group, or
by a trisubstituted silyl group having as the substituents C¹⁻⁵-alkyl, phenyl or benzyl, or
by a benzyl group which is unsubstituted or substituted by C¹⁻⁴-alkoxy or nitro, or
by a tetrahydropyranyl or tetrahydrofuranyl group either of which is unsubstituted or substituted by a C¹⁻⁴-alkoxy or halogen,
or wherein the hydroxy group is protected by a C¹⁻¹⁰ acetal, ketal or orthoester group,
or a pharmaceutically acceptable salt thereof.

2. A compound as claimed in claim 1, wherein B is a group of the formula:

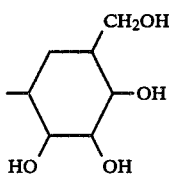

3. A compound as claimed in claim 1, wherein A is a hydroxyl group; and B is a group of the formula;

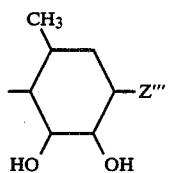

where Z''' is a hydroxyl group or an amino group.

4. A compound as claimed in claim 1, wherein A is a hydroxyl group; and B is a group of the formula;

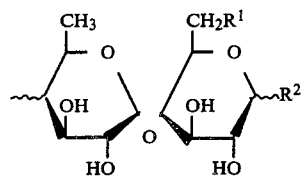

where R¹ and R² are each a hydroxyl group or combine to be oxygen; the chemical bond ∼∼∼∼ designates either the R- or S-configurations.

5. A compound as claimed in claim 1, wherein B is (1) a group of the formula;

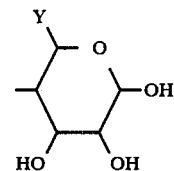

where Y is a lower alkyl group of 1 to 4 carbon atoms or C¹⁻⁴-hydroxyalkyl group or (2) a group of the formula;

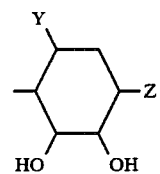

where Y is a lower alkyl group of 1 to 4 carbon atoms and Z is a hydroxyl group or an amino group.

6. A compound as claimed in claim 5, wherein B is selected from the group consisting of 2-methoxy-3,4-dihydroxy-6-hydroxymethyltetrahydropyran-5-yl, 2-methoxy-3,4-dihydroxy-6-methyltetrahydropyran-5-yl, 4-amino-2,3-dihydroxy-6-methylcyclohexan-1-yl and 2,3,4-trihydroxy-6-methylcyclohexan-1-yl.

7. A compound as claimed in claim 1, which is methyl 4-[(1S,2S)-(2,4,5(OH)/3,5(CH₂OH))-2,3,4,5-tetrahydroxy-5-hydroxymethylcyclohexyl]amino-4,6-dideoxy-α-D-glucopyranoside.

8. A compound as claimed in claim 1, which is N-[(1R,2S)-(2,4/3,5)-2,3,4-trihydroxy-5-hydroxymethylcyclohexyl]valiolamine.

9. A compound as claimed in claim 1, which is N-[(1R,2S)-(2,6/3,4)-4-amino-2,3-dihydroxy-6-methylcyclohexyl]valiolamine.

10. A compound as claimed in claim 1, which is N-[(1S,2S)-(2,6/3,4)-4-amino-2,3-dihydroxy-6-methylcyclohexyl]valiolamine.

11. A compound as claimed in claim 1, which is N-[(1R,2S)-(2,6/3,4)-2,3,4-trihydroxy-6-methylcyclohexyl]valiolamine.

12. A compound as claimed in claim 1, which is methyl 4-[(1S,2S)-(2,4,5(OH)/3,5(CH₂OH)-2,3,4,5-tetrahydroxy-5-hydroxymethylcyclohexyl]amino-4-deoxy-α-D-gluropyranoside.

13. (2) A compound as claimed in claim 1, wherein B is a group of the formula:

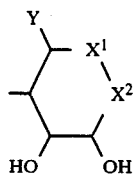

wherein $X^1$ and $X^2$ both are represented by

or wherein one of $X^1$ and $X^2$ is oxygen while the othere is

or wherein $X^1$ and $X^2$ combine to form —O— Y is ① a lower alkyl group of 1 to 4 carbon atoms which may have a hydroxyl substituent, ② a hydroxyl group, or ③ an amino group; and Z is hydrogen, a hydroxyl group, a hydroxymethyl group or an amino group.

14. An α-glucosidase inhibitor composition which contains an effective α-glucosidase inhibiting amount of a compound of the formula:

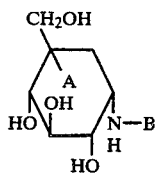

wherein
A is hydrogen or a hydroxyl group;
B is (1) a group of the formula:

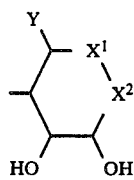

wherein
$X^1$ and $X^2$ both are represented by

or wherein one of $X^1$ and $X^2$ is oxygen while the other is

or wherein $X^1$ and $X^2$ combine to form —O—; Y is ① a $C^{1-4}$-alkyl or $C^{1-4}$-hydroxyalkyl group, ② a hydroxyl group, or ③ an amino group; and Z is hydrogen, a hydroxyl group, a hydroxymethyl group or an amino group;

or B is (2) a group of the formula:

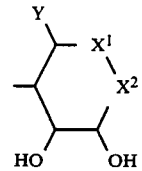

or B is (3) a group of the formula:

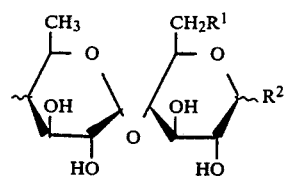

wherein $R^1$ and $R^2$ are each a hydroxyl group or combine to form —O—; the chemical bond ∼∼∼ designates the R- or S-configuration; or pharmaceutically acceptable salt thereof, and a non-toxic carrier.

15. An α-glucosidase inhibitor composition according to claim 14, wherein B is a group of the formula;

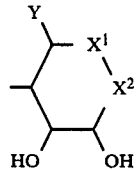

where $X^1$ and $X^2$ are each a group represented by

either of $X^1$ and $X^2$ is oxygen while the other is a group represented by

or $X^1$ and $X^2$ combine to be oxygen; Y is ① a lower alkyl group of 1 to 4 carbon atoms or $C^{1-4}$-hydroxyalkyl group, ② a hydroxyl group, or ③ an amino group; and Z is hydrogen, a hydroxyl group, a hydroxymethyl group, or an amino group.

16. An α-glucosidase composition according to claim 14, wherein B is a group of the formula;

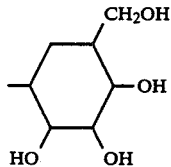

17. An α-glucosidase composition according to claim 14, wherein A is a hydroxyl group; and B is a group of the formula;

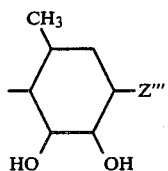

where Z''' is a hydroxyl group or an amino group.

18. An α-glucosidase composition according to claim 14, wherein A is a hydroxyl group; B is a group of the formula;

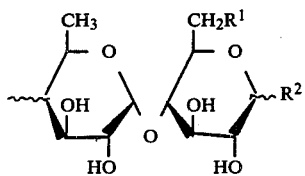

where $R^1$ and $R^2$ are each a hydroxyl group or combine to be oxygen; and the chemical bond ⁓⁓⁓⁓ designates either the R- or S-configurations.

19. An α-glucosidase composition as claimed in claim 14, wherein B is (1) a group of the formula

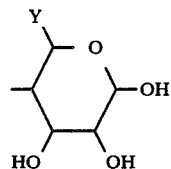

where Y is a lower alkyl group of 1 to 4 carbon atoms $C^{1-4}$-hydroxyalkyl group or (2) a group of the formula where Y is a lower alkyl group; and Z is a hydroxyl group or an amino group.

20. An α-glucosidase composition as claimed in claim 14, wherein B is selected from the group consisting of 2-methoxy-3,4-dihydroxy-6-hydroxymethyltetrahydropyran-5-yl, 2-methoxy-3,4-dihydroxy-6-methyltetrahydropyran-5-yl, 4-amino-2,3-dihydroxy-6-methylcyclohexan-1-yl and 2,3,4-trihydroxy-6-methylcyclohexan-1-yl.

21. An α-glucosidase composition as claimed in claim 14, which contains methyl 4-[(1S,2S)-(2,4,5(OH)/3,5(CH$_2$OH))-2,3,4,5-tetrahydroxy-5-hydroxymethylcyclohexyl]amino-4,6-dideoxy-α-D-glucopyranoside.

22. An α-glucosidase composition as claimed in claim 14, which contains N-[(1R,2S)-(2,4/3,5)-2,3,4-trihydroxy-5-hydroxymethylcyclohexyl]valiolamine.

23. An α-glucosidase composition as claimed in claim 14, which contains N-[(1R,2S)-(2,6/3,4)-4-amino-2,3-dihydroxy-6-methylcyclohexyl]valiolamine.

24. An α-glucosidase composition as claimed in claim 14, which contains N-[(1S,2S)-(2,6/3,4)-4-amino-2,3-dihydroxy-6-methylcyclohexyl]valiolamine.

* * * * *